(12) United States Patent
Young et al.

(10) Patent No.: US 7,026,324 B2
(45) Date of Patent: Apr. 11, 2006

(54) THROMBIN INHIBITORS

(75) Inventors: Mary Beth Young, Lansdale, PA (US); Philippe G. Nantermet, Lansdale, PA (US); Harold G. Selnick, Ambler, PA (US); Peter D. Williams, Harleysville, PA (US)

(73) Assignee: Merck & Co., Inc., Rahway, NJ (US)

( * ) Notice: Subject to any disclaimer, the term of this patent is extended or adjusted under 35 U.S.C. 154(b) by 360 days.

(21) Appl. No.: 10/470,936

(22) PCT Filed: Feb. 5, 2002

(86) PCT No.: PCT/US02/03296

§ 371 (c)(1),
(2), (4) Date: Aug. 1, 2003

(87) PCT Pub. No.: WO02/064140

PCT Pub. Date: Aug. 22, 2002

(65) Prior Publication Data

US 2004/0097730 A1 May 20, 2004

Related U.S. Application Data

(60) Provisional application No. 60/267,787, filed on Feb. 9, 2001.

(51) Int. Cl.
| | |
|---|---|
| A61K 31/4965 | (2006.01) |
| C07D 401/00 | (2006.01) |
| C07D 403/00 | (2006.01) |
| C07D 405/00 | (2006.01) |
| C07D 409/00 | (2006.01) |

(52) U.S. Cl. .............. 514/255.05; 544/405; 546/268.4; 514/338; 514/339

(58) Field of Classification Search ........... 514/255.05, 514/338, 339; 544/405; 546/268.4
See application file for complete search history.

(56) References Cited

U.S. PATENT DOCUMENTS 6,521,625 B1 * 2/2003 Cowden et al. ........ 514/255.05
6,867,217 B1 * 3/2005 South et al. ................. 514/307
2002/0037875 A1 * 3/2002 Semple et al. ................ 514/19

FOREIGN PATENT DOCUMENTS

WO    WO 99/11267    * 3/1999

* cited by examiner

Primary Examiner—James O. Wilson
Assistant Examiner—Zachary C. Tucker
(74) Attorney, Agent, or Firm—Richard S. Parr; Valerie J. Camara

(57) ABSTRACT

Compounds of the invention are useful in inhibiting thrombin and associated thrombotic occlusions having the following structure: or a pharmaceutically acceptable salt thereof, wherein R2 is R3 is selected from the group consisting of 1) hydrogen, 2) halogen, 3) C1–4 alkyl, 4) C3–7 cycloalkyl, 5) CF3, 6) OCF3, 7) C1–4 alkoxy, and 8) cyano; and R12 is a 5-membered heteroaryl ring having 2, 3, or 4 heteroatoms, provided that at least 1 heteroatom is N, and at most 1 of the heteroatoms is S, said ring being unsubstituted or substituted, at any one ring atom, with CH3

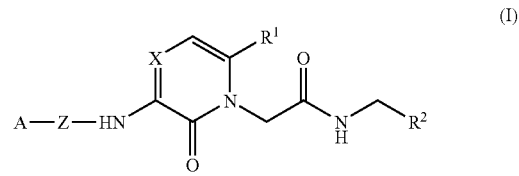

(I)

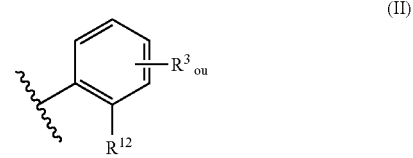

(II)

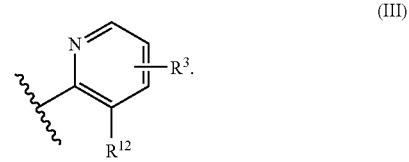

(III)

12 Claims, No Drawings

THROMBIN INHIBITORS

This application claims the benefit of provisional application 60/267,787 filed Feb. 9, 2001.

This application was filed under 35 U.S.C. 371 and is the U.S. National Stage of PCT/US02/03296, filed 5 Feb. 2002.

BACKGROUND OF THE INVENTION

Thrombin is a serine protease present in blood plasma in the form of a precursor, prothrombin. Thrombin plays a central role in the mechanism of blood coagulation by converting the solution plasma protein, fibrinogen, into insoluble fibrin.

Edwards et al., J. Amer. Chem. Soc., (1992) vol. 114, pp. 1854–63, describes peptidyl a-ketobenzoxazoles which are reversible inhibitors of the serine proteases human leukocyte elastase and porcine pancreatic elastase.

European Publication 363 284 describes analogs of peptidase substrates in which the nitrogen atom of the scissile amide group of the substrate peptide has been replaced by hydrogen or a substituted carbonyl moiety.

Australian Publication 86245677 also describes peptidase inhibitors having an activated electrophilic ketone moiety such as fluoromethylene ketone or aketo carboxyl derivatives.

R. J. Brown et al., J. Med. Chem., Vol. 37, pages 1259–1261 (1994) describes orally active, non-peptidic inhibitors of human leukocyte elastase which contain trifluoromethylketone and pyridinone moieties.

H. Mack et al., J. Enzyme Inhibition, Vol. 9, pages 73–86 (1995) describes rigid amidino-phenylalanine thrombin inhibitors which contain a pyridinone moiety as a central core structure.

The present invention concerns pyridinone- and pyrazinone-based compounds having heterobiaryl substitutents.

SUMMARY OF THE INVENTION

The invention includes compounds for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compounds may optionally include anticoagulants, antiplatelet agents, and thrombolytic agents. The compounds can be added to blood, blood products, or mammalian organs in order to effect the desired inhibitions.

The invention also includes a compound for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compounds may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

DETAILED DESCRIPTION OF THE INVENTION AND PREFERRED EMBODIMENTS

Compounds of the invention are useful as thrombin inhibitors and have therapeutic value in for example, preventing coronary artery disease. The invention includes compounds having the following structure:

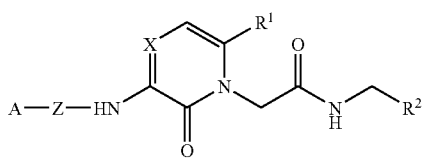

and pharmaceutically acceptable salts thereof, wherein
A is
1) a 6-membered non-heterocyclic unsaturated ring system, unsubstituted, monosubstituted, disubstituted, or trisubstituted, same or different, with $C_{1-4}$ alkyl,
2) a 6-membered heterocyclic unsaturated or saturated ring system wherein 1 ring atom is selected from the group of heteroatoms consisting of N, O and S, wherein the ring carbons are unsubstituted, monosubstituted, disubstituted, or trisubstituted, same or different, with $C_{1-4}$ alkyl,

3)

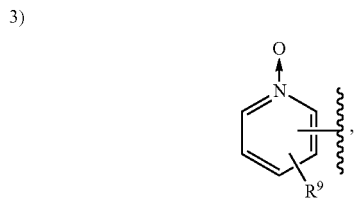

where $R^9$ is hydrogen or $C_{1-8}$alkyl, or
4) $-C_{3-8}$ cycloalkyl;
Z is $-(CH_2)_{2-4}-$, $-CF_2(CH_2)_{1-3}-$, $-(CH_2)_{1-3}SO_2-$, $-(CH_2)_{1-2}NH(CH_2)_{1-4}-$, or $-CH_2CH(R^4)-$, where $R^4$ is $-(CH_2)_{1-2}N(R^5R^6)$, and $R^5$ and $R^6$, same or different, are selected from the group consisting of hydrogen and $C_{1-4}$alkyl;
X is CH or N;
$R^1$ is hydrogen, halogen, or $C_{1-4}$alkyl;
$R^2$ is

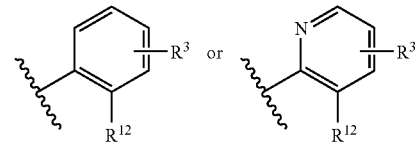

$R^3$ is selected from the group consisting of
1) hydrogen,
2) halogen,
3) $C_{1-4}$ alkyl,
4) $C_{3-7}$ cycloalkyl,
5) $CF_3$,
6) $OCF_3$, 7) C$_{1-4}$ alkoxy, and 8) cyano;

R$^{12}$ is a 5-membered heteroaryl ring having 2, 3, or 4 heteroatoms, provided that at least 1 heteroatom is N, and at most 1 of the heteroatoms is S, said ring being unsubstituted or substituted, at any one ring atom, with CH$_3$.

In a class of compounds and pharmaceutically acceptable salts thereof, R$^1$ is hydrogen, Cl, or CH$_3$.

In a group of this class of compounds and pharmaceutically acceptable salts thereof, A is selected from the group consisting of

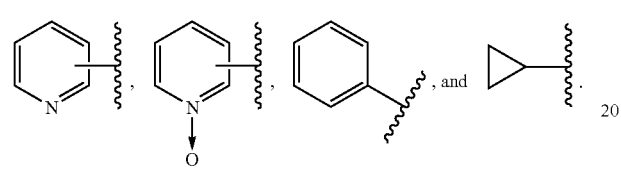

In a subgroup of this group of compounds and pharmaceutically acceptable salts thereof, A is selected from the group consisting of

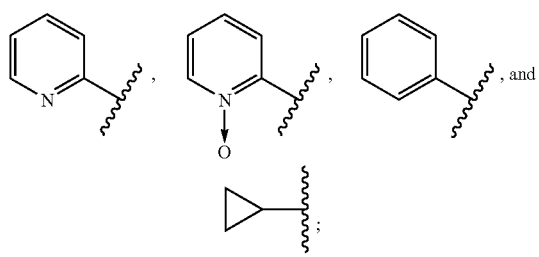

Z is selected from the group consisting of —CF$_2$CH$_2$—, —CH$_2$CH(CH$_2$N(CH$_3$)$_2$)—, —CH$_2$SO$_2$—, and —CH$_2$NH(CH$_2$)$_3$—;

X is N or CH;

R$^1$ is hydrogen, Cl, or CH$_3$; and

R$^2$ is selected from the group consisting of

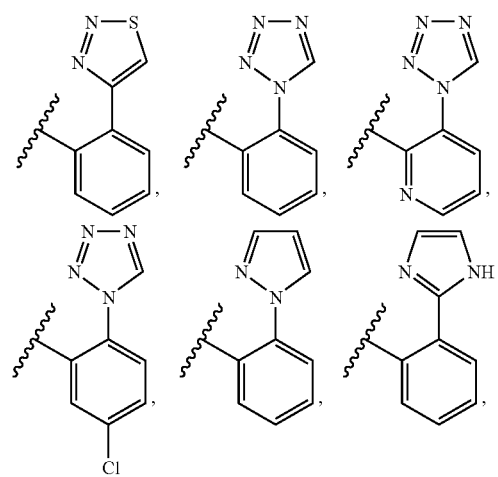

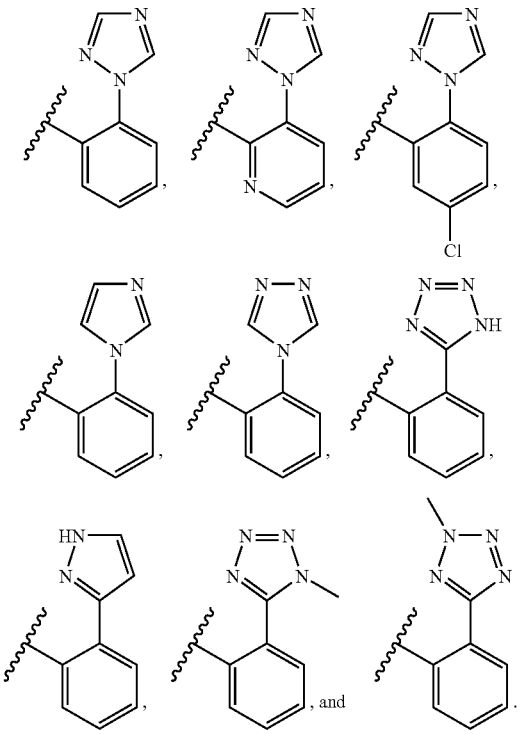

Examples of this subgroup include

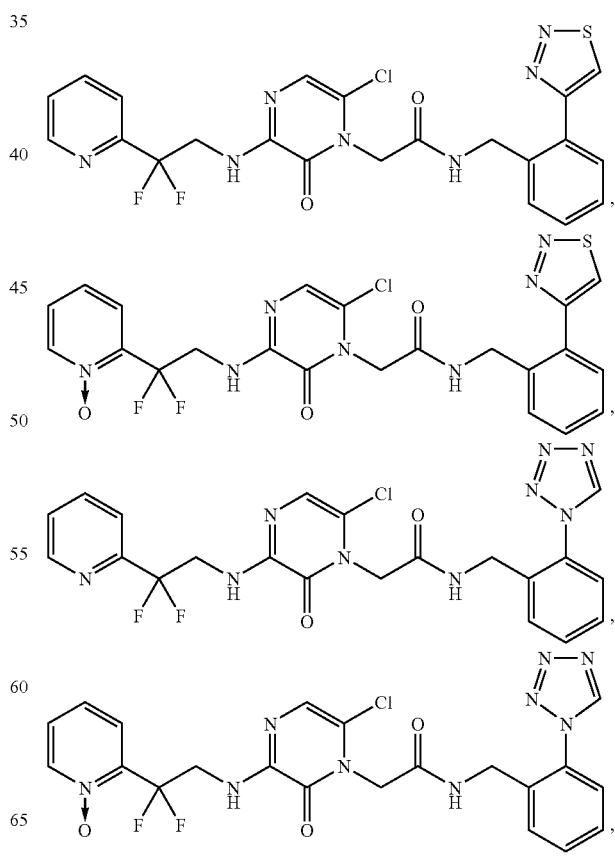

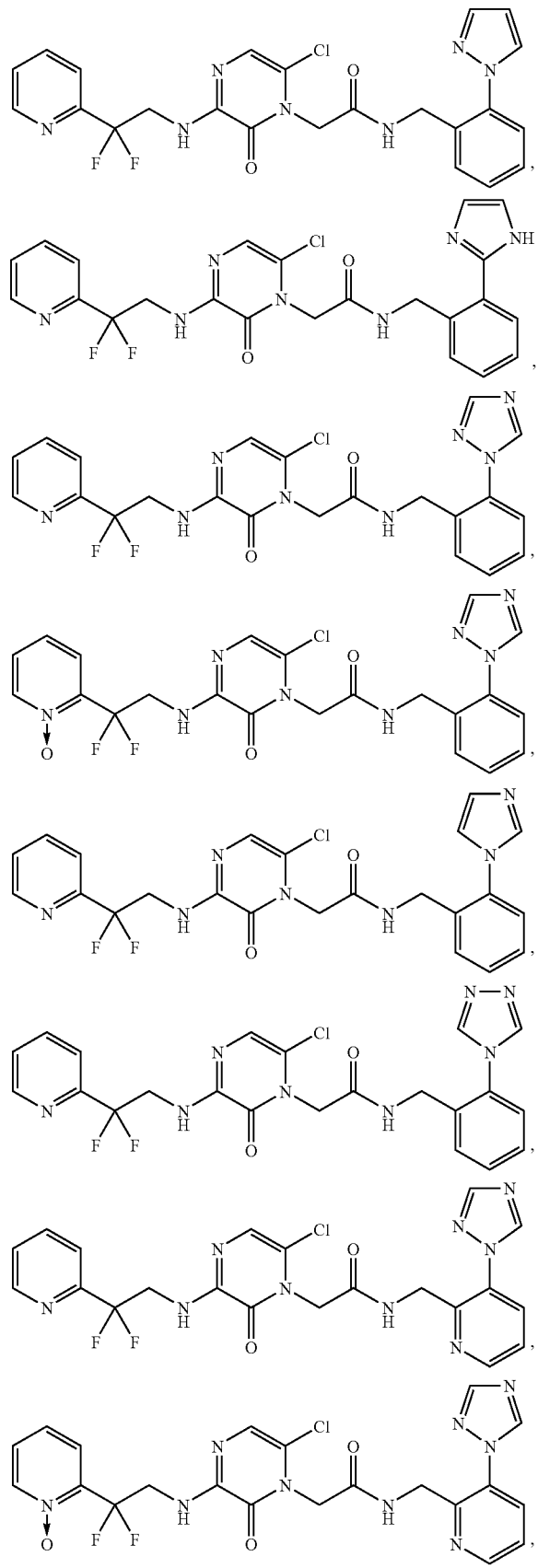
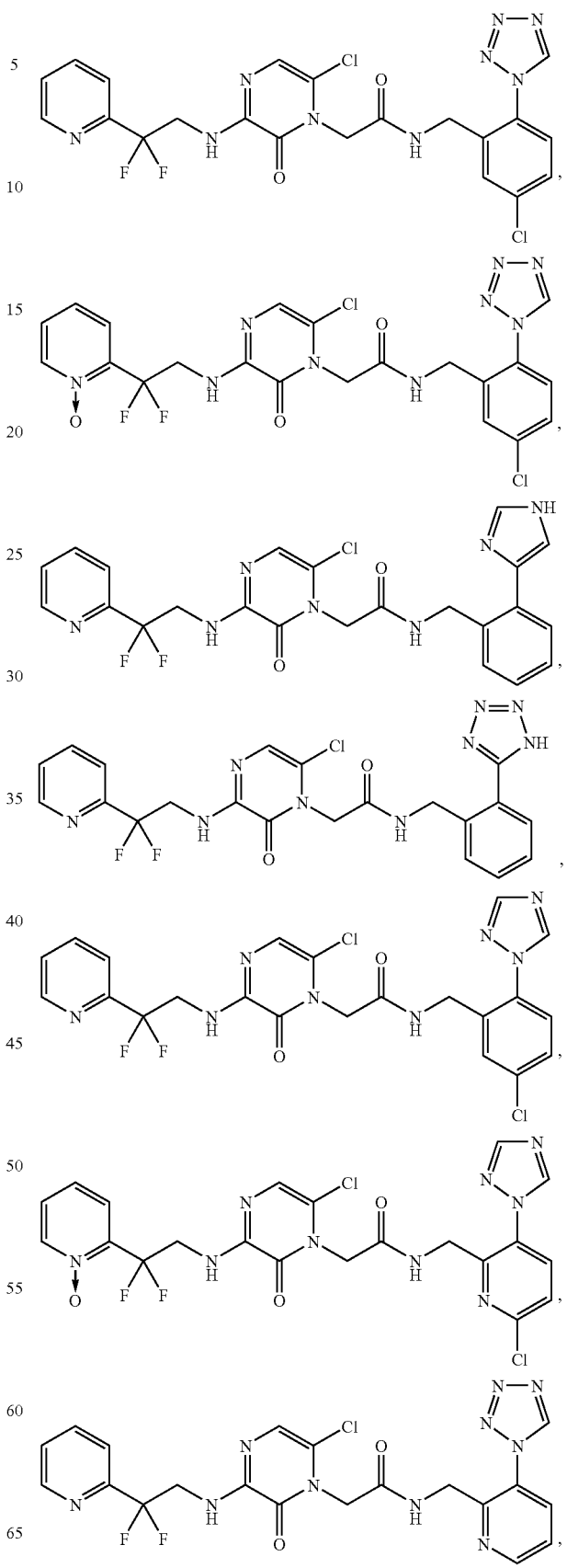

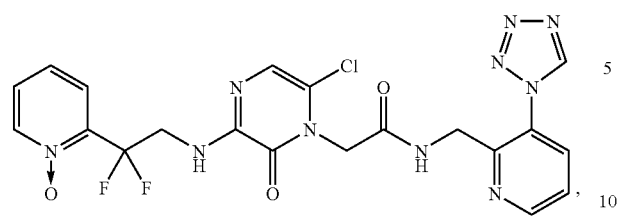
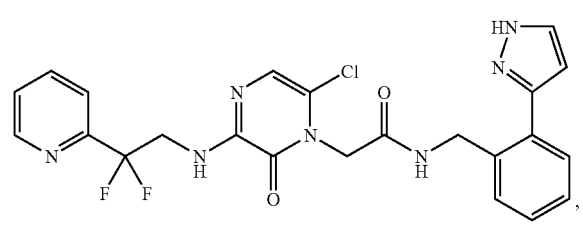
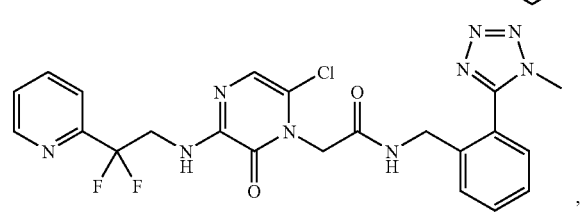
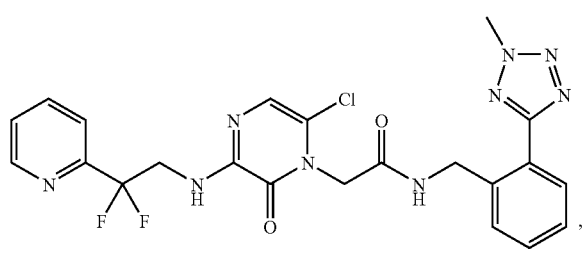
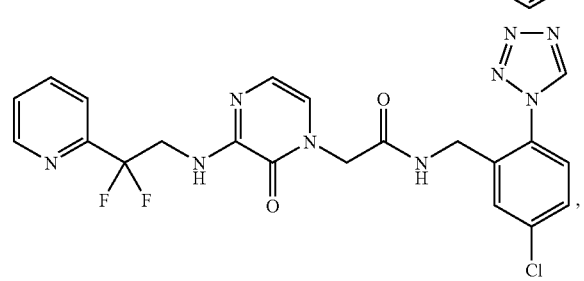
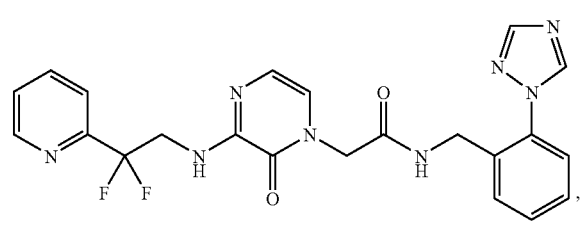
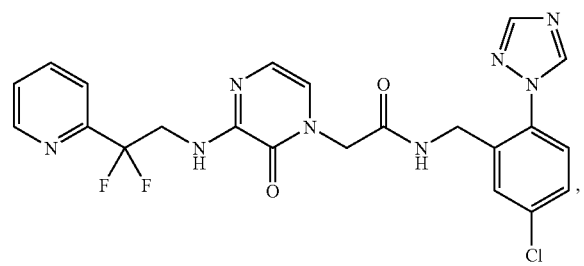
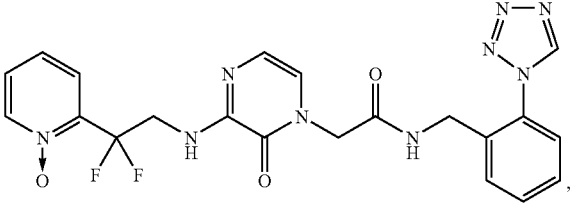
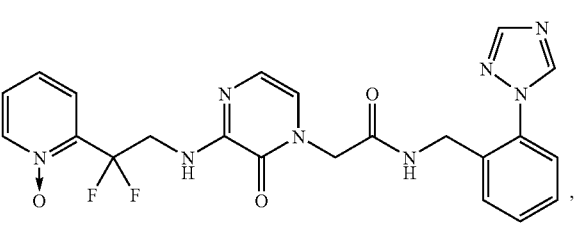
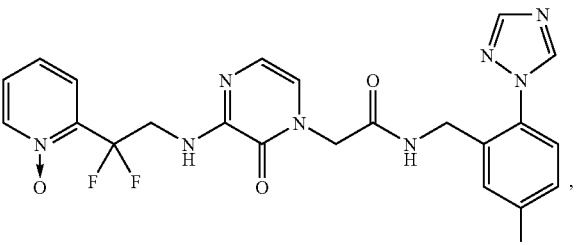
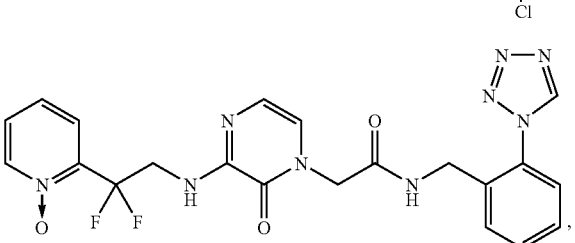
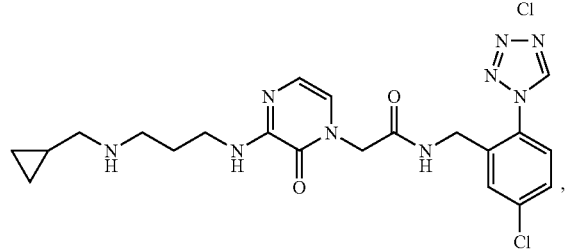
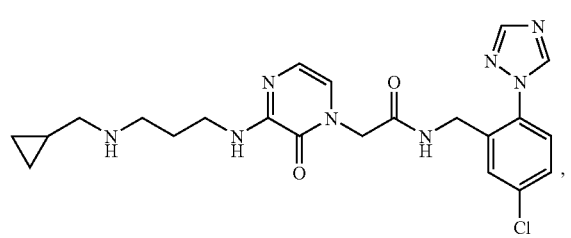

-continued

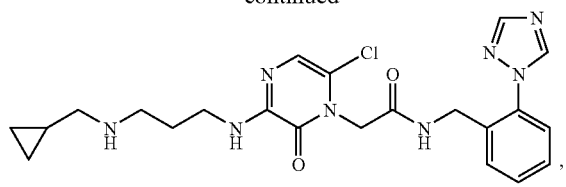

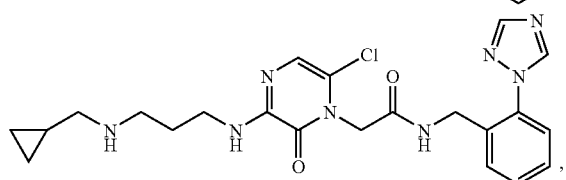

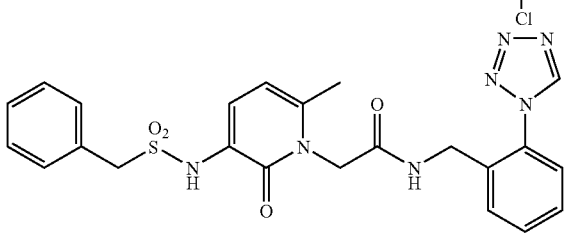

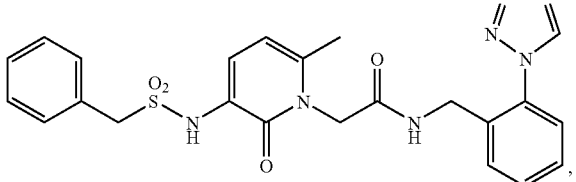

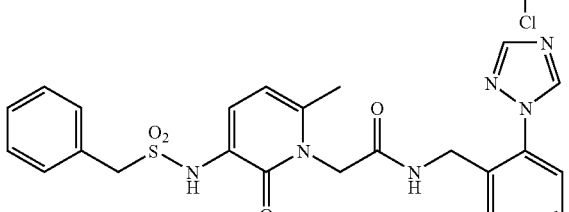

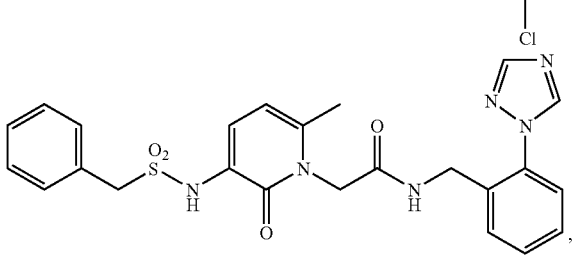

and

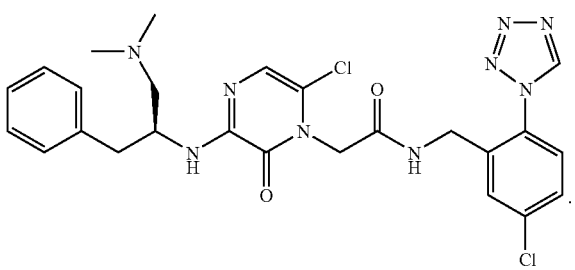

and pharmaceutically acceptable salts thereof.

The compounds of the present invention, may have chiral centers and occur as racemates, racemic mixtures and as individual diastereomers, or enantiomers with all isomeric forms being included in the present invention. The compounds of the present invention may also have polymorphic crystalline forms, with all polymorphic crystalline forms being included in the present invention.

When any variable occurs more than one time in any constituent or in formula I, its definition on each occurrence is independent of its definition at every other occurrence. Also, combinations of substituents and/or variables are permissible only if such combinations result in stable compounds.

Some abbreviations that may appear in this application are as follows:

Abbreviations

| Designation | |
|---|---|
| AcOH | acetic acid |
| AIBN | 2,2'-azobisisobutyronitrile |
| (Boc)$_2$O | di-t-butyl dicarbonate |
| B(OMe)3 | trimethyl borate |
| B(O-iPr)3 | triisopropyl borate |
| BuLi | butyl lithium |
| CHCl$_3$ | chloroform |
| CH$_2$Cl$_2$ | dichloromethane |
| CH(OMe)$_3$ | trimethylorthoformate |
| Cs$_2$CO$_3$ | cesium carbonate |
| DAST | diethylaminosulfurtrifluoride |
| DBU | 1,8-diazabicyclo[5.4.0]undec-7-ene |
| DCE | 1,2-dichloroethane |
| DIEA | diisopropylethylamine |
| DMAP | dimethylaminopyridine |
| DMF | dimethylformamide |
| DPPA | diphenylphosphoryl azide |
| EDC | 1-ethyl-3-(3-dimethylaminopropyl)carbodiimide hydrochloride |
| EtOAc | ethyl acetate |
| EtOH | ethanol |
| Et$_2$O | diethyl ether |
| Et$_3$N | triethylamine |
| HCl | hydrochloric acid |
| HOAc | acetic acid |
| HOAT | 1-hydroxy-7-azabenzotriazole |
| H$_2$SO$_4$ | sulfuric acid |
| IPrOH | 2-propanol |
| KOH | potassium hydroxide |
| K$_2$CO$_3$ | potassium carbonate |
| LAH | lithium aluminum hydride |
| LiCl | lithium chloride |
| LiOH | lithium hydroxide |
| MCPBA | m-chloroperoxybenzoic acid |
| MeI | iodomethane |
| MeOH | methanol |
| MgSO$_4$ | magnesium sulfate |
| n-BuLi | n-butyllithium |
| N$_3$PO(Ph)$_2$ | diphenyl phosphoryl azide |
| NaBH$_4$ | sodium borohydride |
| NaHCO$_3$ | sodium hydrogen carbonate |
| NaN$_3$ | sodium azide |
| NaOH | sodium hydroxide |
| Na$_2$CO$_3$ | sodium carbonate |
| Na$_2$SO$_4$ | sodium sulfate |
| Na$_2$S$_2$O$_3$ | sodium thiosulfate |
| NBS | N-bromosuccinimide |
| NCS | N-chlorosuccinimide |
| NH$_4$Cl | ammonium chloride |
| NH$_4$OH | ammonium hydroxide |
| P(Ph)$_3$ | triphenyl phosphine |
| Pd-C | palladium on activated carbon catalyst |
| Pd(PPh)$_3$ | tetrakis triphenylphosphine palladium |
| PhCH$_3$ | toluene |

-continued

| Designation | |
|---|---|
| POBr₃ | phosphorous oxybromide |
| TEA | triethylamine |
| Tf₂O | trifluoromethane sulfonic anhydride |
| THF | tetrahydrofuran |
| SiO₂ | silicon oxide |
| SOCl₃ | thionyl chloride |
| SnCl₂ | tin chloride |
| Zn(CN)₂ | zinc cyanide |

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl); "alkoxy" represents a linear or branched alkyl group of indicated number of carbon atoms attached through an oxygen bridge; "halogen", as used herein, means fluoro, chloro, bromo and iodo; and "counterion" is used to represent a small, single negatively-charged species, such as chloride, bromide, hydroxide, acetate, trifluoroacetate, perchlorate, nitrate, benzoate, maleate, sulfate, tartrate, hemitartrate, benzene sulfonate, and the like.

The term "cycloC$_{3\text{-}7}$alkyl" is intended to include cyclopropyl, cyclobutyl, cyclopentyl, cyclohexyl and cycloheptyl, and the like.

The term "aryl" as used herein except where noted, represents a stable 6- to 10-membered mono- or bicyclic ring system such as phenyl, or naphthyl. The aryl ring can be unsubstituted or substituted with one or more of C$_{1\text{-}4}$ lower alkyl; hydroxy; alkoxy; halogen; amino.

The pyridyl N-oxide portion of the compounds of the invention are structurally depicted using conventional representations

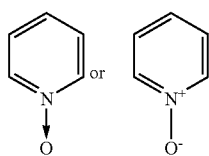

which have equivalent meanings.

In this specification methyl substituents may be represented by

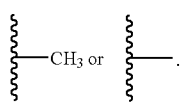

For example, the structures

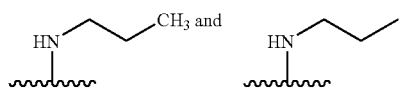

have equivalent meanings.

The pharmaceutically-acceptable salts of the compounds of Formula I (in the form of water- or oil-soluble or dispersible products) include the conventional non-toxic salts such as those derived from inorganic acids, e.g. hydrochloric, hydrobromoic, sulfuric, sulfamic, phosphoric, nitric and the like, or the quaternary ammonium salts which are formed, e.g., from inorganic or organic acids or bases. Examples of acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

Thrombin Inhibitors—Therapeutic Uses—Method of Using

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Thrombin inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the thrombin inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention are useful for treating or preventing venous thromboembolism (e.g. obstruction or occlusion of a vein by a detached thrombus; obstruction or occlusion of a lung artery by a detached thrombus), cardiogenic thromboembolism (e.g. obstruction or occlusion of the heart by a detached thrombus), arterial thrombosis (e.g. formation of a thrombus within an artery that may cause infarction of tissue supplied by the artery), atherosclerosis (e.g. arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention are useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention are useful for maintaining patency in arteriovenous cannulas.

Examples of atherosclerosis include arteriosclerosis.

Examples of devices that come into contact with blood include vascular grafts, stents, orthopedic prosthesis, cardiac prosthesis, and extracorporeal circulation systems The thrombin inhibitors of the invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but nontoxic amount of the compound desired can be employed as an anti-aggregation agent. For treating ocular build up of fibrin, the compounds may be administered intraocularly or topically as well as orally or parenterally.

The thrombin inhibitors can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The thrombin inhibitors can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The thrombin inhibitors may also be delivered by the use of monoclonal antibodies as individual carriers to which the compound molecules are coupled. The thrombin inhibitors may also be coupled with soluble polymers as targetable drug carriers. Such polymers can include polyvinlypyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the thrombin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The dosage regimen utilizing the thrombin inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the thrombin inhibitors, when used for the indicated effects, will range between about 0.01 mg per kg of body weight per day (mg/kg/day) to about 30 mg/kg/day, preferably 0.025–7.5 mg/kg/day, more preferably 0.1–2.5 mg/kg/day, and most preferably 0.1–0.5 mg/kg/day (unless specificed otherwise, amounts of active ingredients are on free base basis). For example, an 80 kg patient would receive between about 0.8 mg/day and 2.4 g/day, preferably 2–600 mg/day, more preferably 8–200 mg/day, and most preferably 8–40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the thrombin inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025–7.5 mg/kg/day, preferably 0.1–2.5 mg/kg/day, and more preferably 0.1–0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01–1.0 mg/ml, e.g. 0.1 mg/ml, 0.3 mg/ml, and 0.6 mg/ml, and administered in amounts per day of between 0.01 ml/kg patient weight and 10.0 ml/kg patient weight, e.g. 0.1 ml/kg, 0.2 ml/kg, 0.5 ml/kg. In one example, an 80 kg patient, receiving 8 ml twice a day of an intravenous formulation having a concentration of active ingredient of 0.5 mg/ml, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. Consideration should be given to the solubility of the drug. The choice of appropriate buffer and pH of a formulation, depending on solubility of the drug to be administered, is readily made by a person having ordinary skill in the art.

The compounds can also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

The thrombin inhibitors are typically administered as active ingredients in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The invention also includes a method for treating an inflammatory disease in a patient which comprises treating the patient with a composition comprising a compound of the present invention. Such diseases include but are not limited to nephritis, systemic lupus erythematosus, rheumatoid arthritis, glomerulonephritis, and sacoidosis.

The invention is also a method for treating an inflammatory disease in a patient that comprises treating the patient with a combination comprising a compound of the invention and an NSAID, e.g., a COX-2 inhibitor. Such diseases include but are not limited to nephritis, systemic lupus, erythematosus, rheumatoid arthritis, glomerulonephritis, vasculitis and sacoidosis.

The present invention is a method for relieving pain, fever and inflammation of a variety of conditions including nephritis, systemic lupus erythematosus, rheumatoid arthritis, glomerulonephritis, sacoidosis, rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis degenerative joint diseases (osteoarthritis), gout and ankylosing spondylitis, bursitis, burns, injuries, following surgical and dental procedures in a patient by administering to the patient a therapeutically effective amount of a compound of the invention. Thrombin inhibitors may also be useful for the treatment of dementia including pre-senile and senile dementia, and in particular, dementia associated with Alzheimer Disease.

In inflammatory diseases wherein fibrin formation is prominent, the fibrin may be a determinant of the pathology. Fibrin serves as a matrix onto which inflammatory cells can migrate and adhere. (see Sherman et al., 1977 *J. Exp. Med.* 145:76–85; Altieri et al., 1986 *J. Clin. Invest.* 78:968–976; Wright et al., 1983 *Proc. Natl. Acad. Sci.* 85:7734–7738; Altieri et al., 1993 *J. Biol. Chem.* 268;1847–1853). Fibrin also enhances expression of the inflammatory cytokine IL-1beta and decreases expression of IL-1 receptor antagonist by human peripheral blood mononuclear cells (see Perez 1995 *J. Immunol.* 154:1879–1887). The anticoagulants warfarin and heparin attenuate delayed-type hypersensitivity reactions and experimental nephritis in animals. (see Jasain et al., Immunopathogenesis of Rheumatoid Arthritis Eds. G.S. Panayi et al., Surrey, UK, Reedbooks, Ltd. and Halpern et al., 1965 *Nature* 205:257–259). Enzymatic defibrination with ancrod diminishes the degree of experimental nephritis (Naish et al., 1972 *Clin. Sci.* 42:643–646), systemic lupus erythematosus (Cole et al., 1990 *Kidney Int.* 37:29–35, and rheumatoid arthritis (see Busso et al., 1998 *J. Clin. Invest.* 102:41–50) in animals, and glomerulonephritis in man (see Kim et al., 1988 *Q. J. Med.* 69:879–905). Additionally, intra articular injection of fibrin induces arthritis in rabbits immunized with fibrin Dumonde et al., 1961 *British Journal of Experimental Pathology* XLIII:373–383), and antigen-induced arthritis in mice is exacerbated in urokinase-deficient mice wherein fibrinolysis synovial fibrin is compromised (see Busso et al., 1998 *J. Clin. Invest.* 102:41–50).

In diseases where fibrin deposition is prominent such as, but not limited to, rheumatoid arthritis, systemic lupus erythematosus, glomerulonephritis, vasculitis and sacoidosis, lowering the steady state concentration of fibrin by administration of a compound of the invention will, according to the instant invention, diminish the pathological inflammatory responses associated with these diseases.

Similarly, compounds of the invention will be useful as a partial or complete substitute for conventional NSAIDs in preparations wherein they are presently co-administered with other agents or ingredients. Thus in further aspects, the invention encompasses pharmaceutical compositions for treating inflammatory diseases as defined above comprising a non-toxic therapeutically effective amount of a compound of the invention as defined above and one or more ingredients such as another pain reliever including acetaminophen or phenacetin; a potentiator including caffeine; an H2-antagonist, aluminum or magnesium hydroxide, simethicone, a decongestant including phenylephrine, phenylpropanolamine, pseudophedrine, oxymetazoline, ephinephrine, naphazoline, xylometazoline, propylhexedrine, or levodesoxyephedrine; an antiitussive including codeine, hydrocodone, caramiphen, carbetapentane, or dextramethorphan; a diuretic; a sedating or non-sedating antihistamine. In addition the invention encompasses a method of treating inflammatory diseases comprising administration to a patient in need of such treatment a non-toxic therapeutically effect amount of a compound of the invention, optionally co-administered with one or more of such ingredients as listed immediately above.

The instant invention also involves a novel combination therapy comprising the administration of a therapeutically effective amount of an NSAID such as a COX-2 inhibitor in combination with a therapeutically effective amount, as described above, of a compound of the invention to a mammal, and more particularly, to a human. The combination therapy is used to treat inflammatory diseases.

The instant pharmaceutical combinations comprising a compound of the invention, in therapeutically effective amounts described above, in combination with an NSAID such as a COX-2 inhibitor include administration of a single pharmaceutical dosage formulation which contains both a compound of the invention and the NSAID, as well as administration of each active agent in its own separate pharmaceutical dosage formulation. Where separate dosage formulations are used, the compound of the invention and the NSAID can be administered at essentially the same time, i.e., concurrently, or at separately staggered times, i.e, sequentially. The "instant pharmaceutical combination" is understood to include all these regimens. Administration in these various ways are suitable for the present invention as long as the beneficial pharmaceutical effect of the compound of the invention and the NSAID are realized by the patient at substantially the same time. Such beneficial effect is preferably achieved when the target blood level concentrations of each active drug are maintained at substantially the same time. It is preferred that the compound of the invention and the NSAID be co-administered concurrently on a once-a-day dosing schedule; however, varying dosing schedules, such as the compound of the invention once per day and the NSAID once, twice or more times per day, or the NSAID once per day and the compound of the invention once, twice or more times per day, is also encompassed herein. A single oral dosage formulation comprised of both the compound of the invention and the NSAID is preferred. A single dosage formulation will provide convenience for the patient.

The instant invention also provides pharmaceutical compositions comprised of a therapeutically effective amount of an NSAID, or a pharmaceutically acceptable salt thereof, in combination with a therapeutically effective amount of a compound of the invention, or a pharmaceutically acceptable salt thereof, and a pharmaceutically acceptable carrier. One embodiment of the instant compositions is a single composition adapted for oral administration comprised of a therapeutically effective amount of a COX-2 inhibitor in combination with a therapeutically effective amount of a compound of the invention and a pharmaceutically acceptable carrier. The combination can also be administered in separate dosage forms, each having one of the active agents. If administered in separate dosage forms, the separate dosage forms are administered such that the beneficial effect of each active agent is realized by the patient at substantially the same time.

Common NSAIDs include salicylates such as aspirin, sodium salicylate, choline salicylate, salicylsalicylic acid, diflunisal, and salsalate; indoleacetic acids such as indomethacin and sulindac; pyrazoles such as phenylbutazone, oxyphenbutazone; pyrrolealkanoic acids such as tolmetin; phenylacetic acids such as ibuprofen, feroprofen, flurbiprofen, and ketoprofen; fenamates such as mefanamic acid, and meclofenamate; oxicams such as piroxicam; and naphthaleneacetic acids such as naproxen. Cyclo-oxygenase inhibitors such as COX-1 and COX-2 inhibitors are also NSAIDs.

Employing the human whole blood COX-1 assay and the human whole blood COX-2 assay described in C. Brideau et al, Inflamm. Res. 45: 68–74 (1996), herein incorporated by reference, preferably, the compounds have a cyclooxygenase-2 $IC_{50}$ of less than about 2 µM in the human whole blood COX-2 assay, yet have a cyclooxygenase-1 $IC_{50}$ of greater than about 5 µM in the human whole blood COX-1 assay. Also preferably, the compounds have a selectivity ratio of cyclooxygenase-2 inhibition over cyclooxygenase-1 inhibition of at least 10, and more preferably of at least 40. The resulting selectivity may indicate an ability to reduce the incidence of common NSAID-induced side effects.

The inhibitor of cyclooxygenase-2 may be administered at a dosage level up to conventional dosage levels for NSAIDs. Suitable dosage levels will depend upon the antiinflammatory effect of the chosen inhibitor of cyclooxygenase-2, but typically suitable levels will be about 0.001 to 50 mg/kg per day, preferably 0.005 to 30 mg/kg per day, and especially 0.05 to 10 mg/kg per day, e.g., 12.5 mg once each day or 25 mg once each day. The compound may be administered on a regimen of up to 6 times per day, preferably 1 to 4 times per day, and especially once per day.

The dosage regimen utilizing a compound of the invention in combination with the NSAID is selected in accordance with a variety of factors including type, species, age, weight, sex and medical condition of the patient; the severity of the condition to be treated; the route of administration; the renal and hepatic function of the patient; and the particular compound or salt or ester thereof employed. Since two different active agents are being used together in a combination therapy, the potency of each of the agents and the interactive effects achieved by combining them together must also be taken into account. A consideration of these factors is well within the purview of the ordinarily skilled clinician for the purpose of determining the therapeutically effective or prophylactically effective dosage amounts needed to prevent, counter, or arrest the progress of the condition.

Administration of the drug combination to the patient includes both self-administration and administration to the patient by another person.

Additional active agents may be used in combination with the compound of the invention in a single dosage formulation, or may be administered to the patient in a separate dosage formulation, which allows for concurrent or sequential administration. Examples of additional active agents which may be employed include HMG-CoA synthase inhibitors; squalene epoxidase inhibitors; squalene synthetase inhibitors (also known as squalene synthase inhibitors), acyl-coenzyme A: cholesterol acyltransferase (ACAT) inhibitors; probucol; niacin; fibrates such as clofibrate, fenofibrate, and gemfibrizol; cholesterol absorption inhibitors; bile acid sequestrants; LDL (low density lipoprotein) receptor inducers; vitamin $B_6$ (also known as pyridoxine) and the pharmaceutically acceptable salts thereof such as the HCl salt; vitamin $B_{12}$ (also known as cyanocobalamin); β-adrenergic receptor blockers; folic acid or a pharmaceutically acceptable salt or ester thereof such as the sodium salt and the methylglucamine salt; and anti-oxidant vitamins such as vitamin C and E and beta carotene.

The thrombin inhibitors can also be co-administered with suitable anti-platelet agents, including, but not limited to, fibrinogen receptor antagonists (e.g. to treat or prevent unstable angina or to prevent reocclusion after angioplasty and restenosis), anticoagulants such as aspirin, thrombolytic agents such as plasminogen activators or streptokinase to achieve synergistic effects in the treatment of various vascular pathologies, or lipid lowering agents including anti-hypercholesterolemics (e.g. HMG CoA reductase inhibitors such as lovastatin and simvastatin, HMG CoA synthase inhibitors, etc.) to treat or prevent atherosclerosis. For example, patients suffering from coronary artery disease, and patients subjected to angioplasty procedures, would benefit from coadministration of fibrinogen receptor antagonists and thrombin inhibitors. Also, thrombin inhibitors enhance the efficiency of tissue plasminogen activator-mediated thrombolytic reperfusion. Thrombin inhibitors may be administered first following thrombus formation, and tissue plasminogen activator or other plasminogen activator is administered thereafter.

Typical doses of thrombin inhibitors of the invention in combination with other suitable anti-platelet agents, anticoagulation agents, or thrombolytic agents may be the same as those doses of thrombin inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

Unless otherwise stated, all NMR determinations were made using 400 MHz field strength.

The compounds claimed in this invention can be prepared via the schemes described below. In general, 2-heterocyclic benzylamines were coupled with various pyrazinone or pyridinone carboxylic acids to produce the claimed compounds:

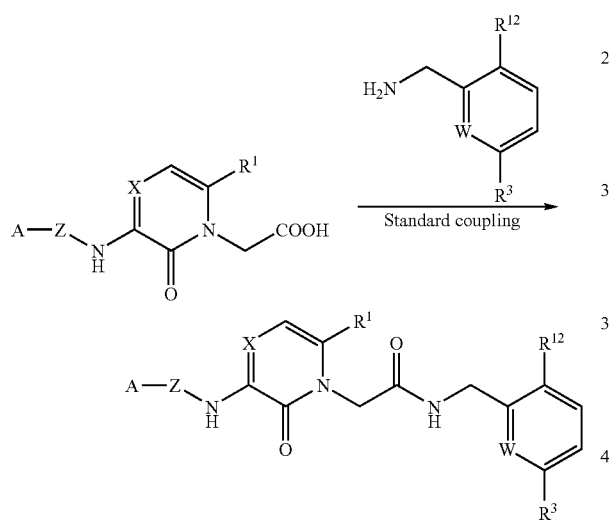

where A-Z is, for example,
2,2-difluoro-2-pyridin-2-yl-ethylamino,
2,2-difluoro-2-(1-oxy-pyridin-2-yl)-ethylamino,
(cyclopropylmethyl-amino)-propylamino,
1-dimethylaminomethyl-2-phenyl-ethylamino, or
phenylmethanesulfonylamino;
X is N or CH;
$R^1$ is Cl or hydrogen;
$R^{12}$ is a 5-membered heterocyclic ring;
$R^3$ is Cl or hydrogen; and
W is CH or N.

The synthesis of the benzylamines is depicted in schemes 1 through 10 and the carboxylic acids are found in schemes 11 through 16.

In scheme 1, the thiadiazole ring was synthesized via cyclization of 1-1 with thionyl chloride. Functional group transformation of the methyl group of 1-2 to the benzylamine was accomplished in three steps via the methyl bromide and methyl azide.

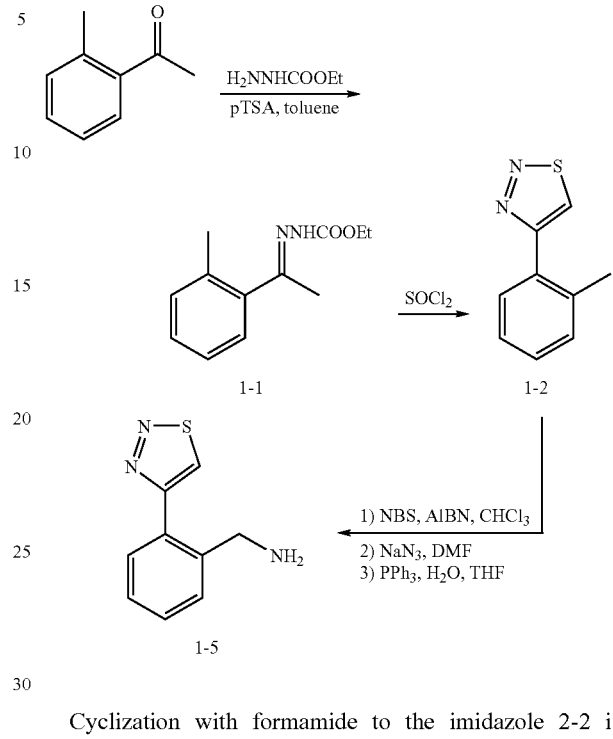

Cyclization with formamide to the imidazole 2-2 is depicted in scheme 2. Protection of the imidazole group with trityl, conversion of the phenyl bromide to the nitrile and subsequent reduction gave the benzylamine, 2-6.

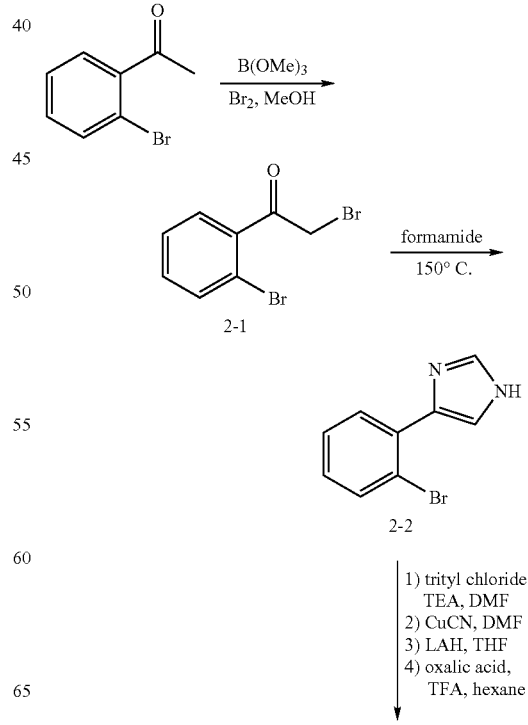

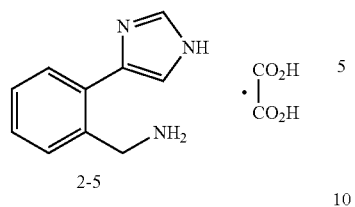

2-5

In scheme 3, an aminobenzoic acid was converted to the tetrazole 3-1 or 4 through cyclization with sodium azide and trimethyl orthoformate. The carboxylic acid of 3-1 or 4 was converted to the amide and then to the nitrile which was reduced to the amine 3-4 or 4.

Scheme 3

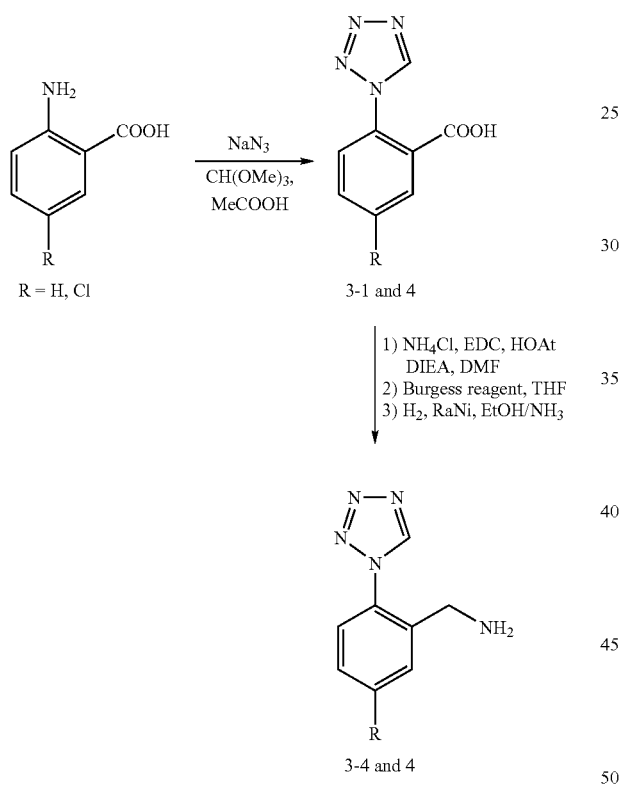

The pyrazole ring of 5-1 was formed from 2-hydrazinobenzoic acid and malonaldehyde bis-dimethylacetal as shown in scheme 4. The carboxylic acid was converted to the amide which was then reduced to give 5-3.

Scheme 4

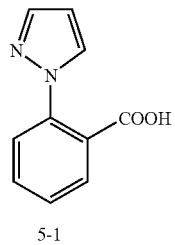

5-1

1) NH₄Cl, EDC, HOAt
   DIEA, DMF
2) BH₃, THF 5-3

In scheme 5 phthalonitrile was cyclized to the imidazole, 6-2 via the benzimidic acid 6-1. Reduction of the nitrite afforded 6-4.

Scheme 5

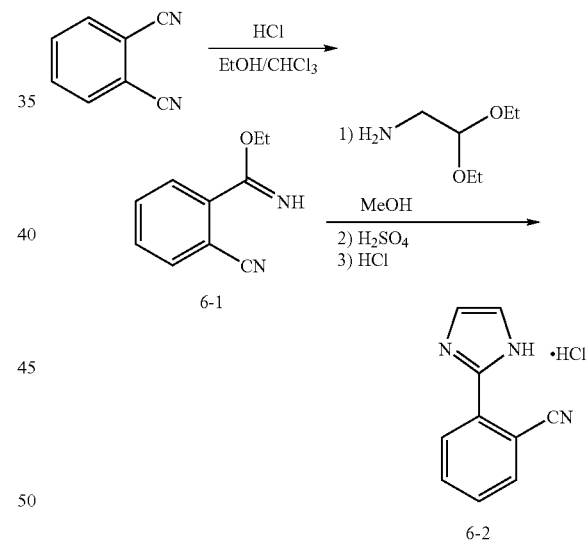

In scheme 6, the fluorine atom of 2-cyano-3-fluoropyridine was displaced with [1,2,4]-triazole to give 7-1 and with tetrazole to give 11-1. Reduction yielded the respective benzylamines 7-3 and 11-2.
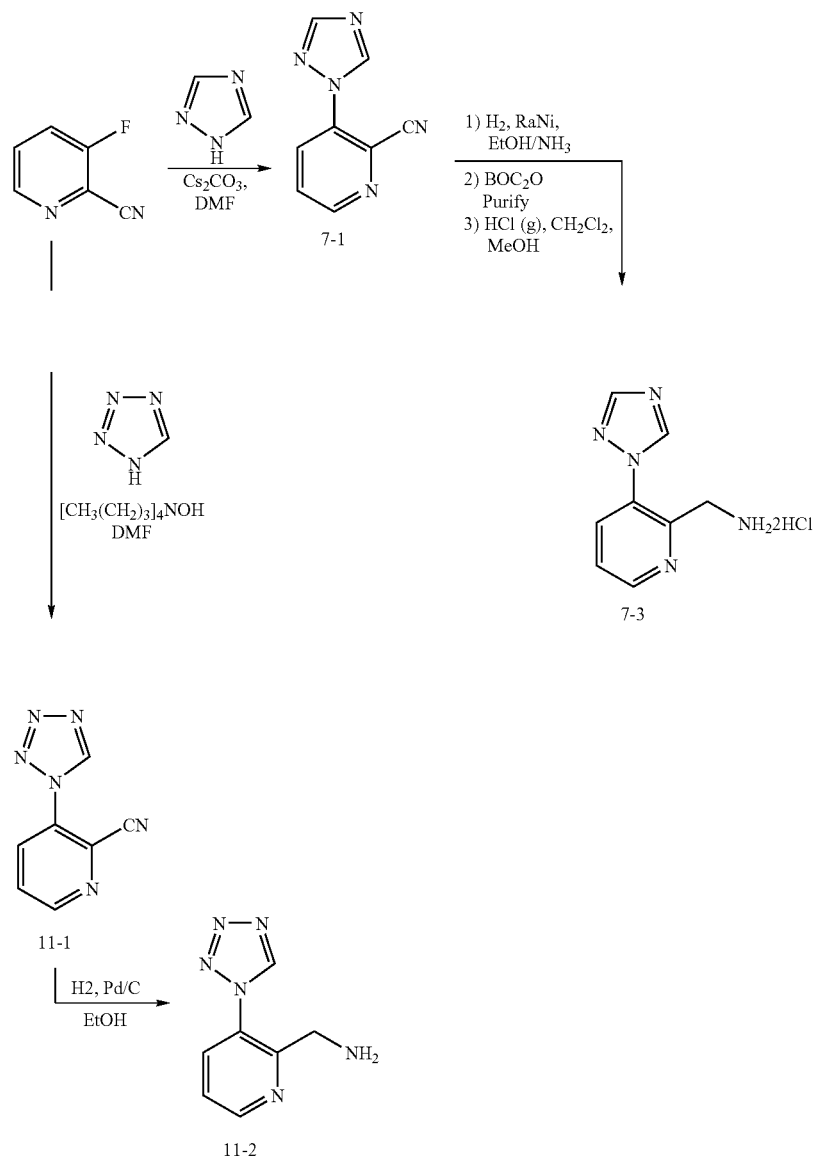
Chlorine was displaced by [1,2,4]-triazole in scheme 7 to give 8-1 with subsequent reduction to 8-2.
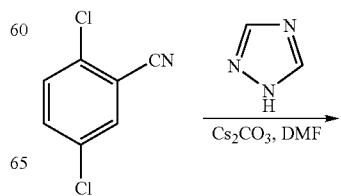

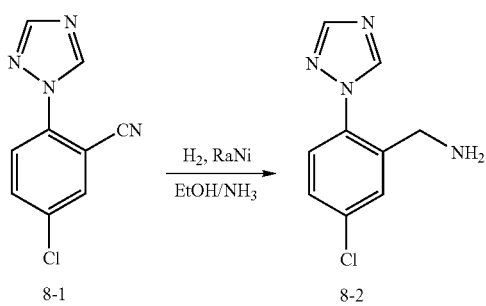

In scheme 8, displacement of fluorine on 2-fluorocyanobenzene gave two regioisomers, 9-1 which were reduced to 9-2 and 10-1. Displacement with imidazole and reduction gave 13-2.

Pyrazole was protected as its THP derivative in scheme 9 to give 12-1 which was then reacted with triisopropyl borate and deprotected to give the boronic acid, 12-2. Palladium mediated coupling of this compound with Boc protected bromobenzylamine, 12-3 gave 12-4. Removal of the Boc group gave 12-5.

Scheme 9

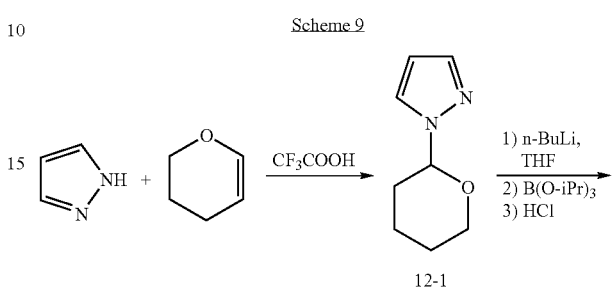

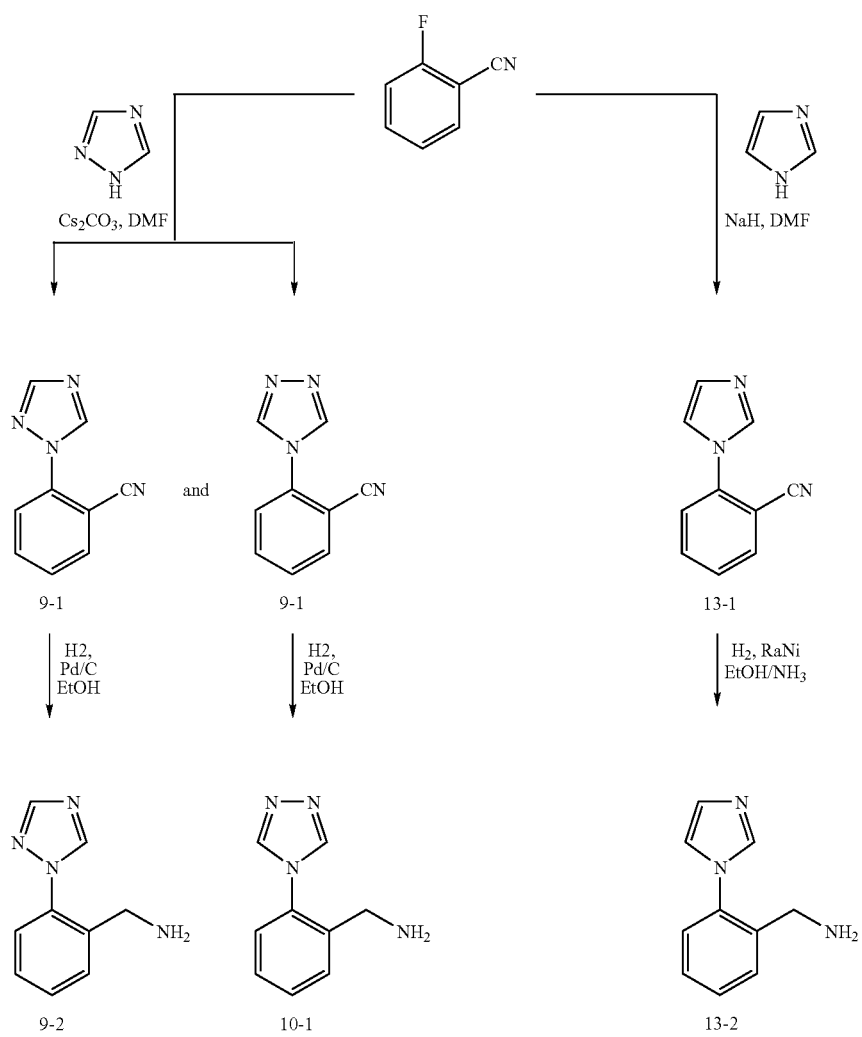

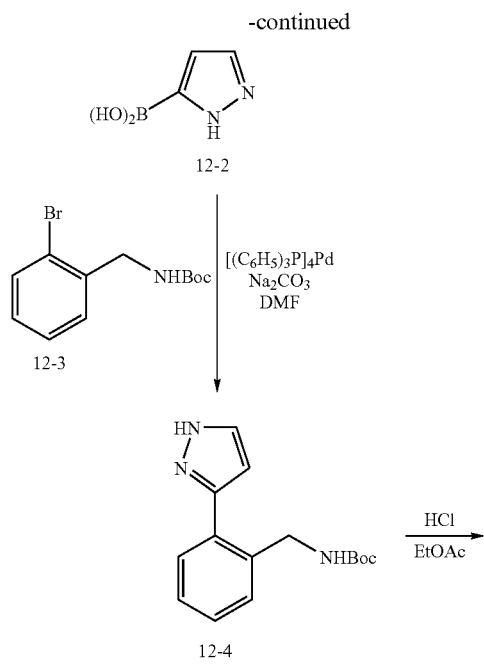
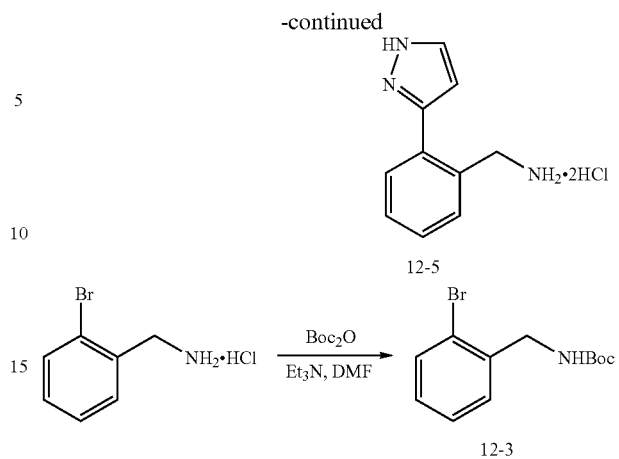

The final benzylamine synthesis, shown in scheme 10 begins with 2-bromomethyl-benzonitrile. Displacement of bromine with azide followed by reduction and concurrent protection of the benzylamine with a Boc group gave 14-2. Cyclization to the tetrazole 14-3 was afforded with sodium azide and ammonium chloride. Boc removal gave 14-4. Reaction of 14-3 with iodomethane gave two regioisomers, 15-1 which were then deprotected to give 15-2 and 16-1.

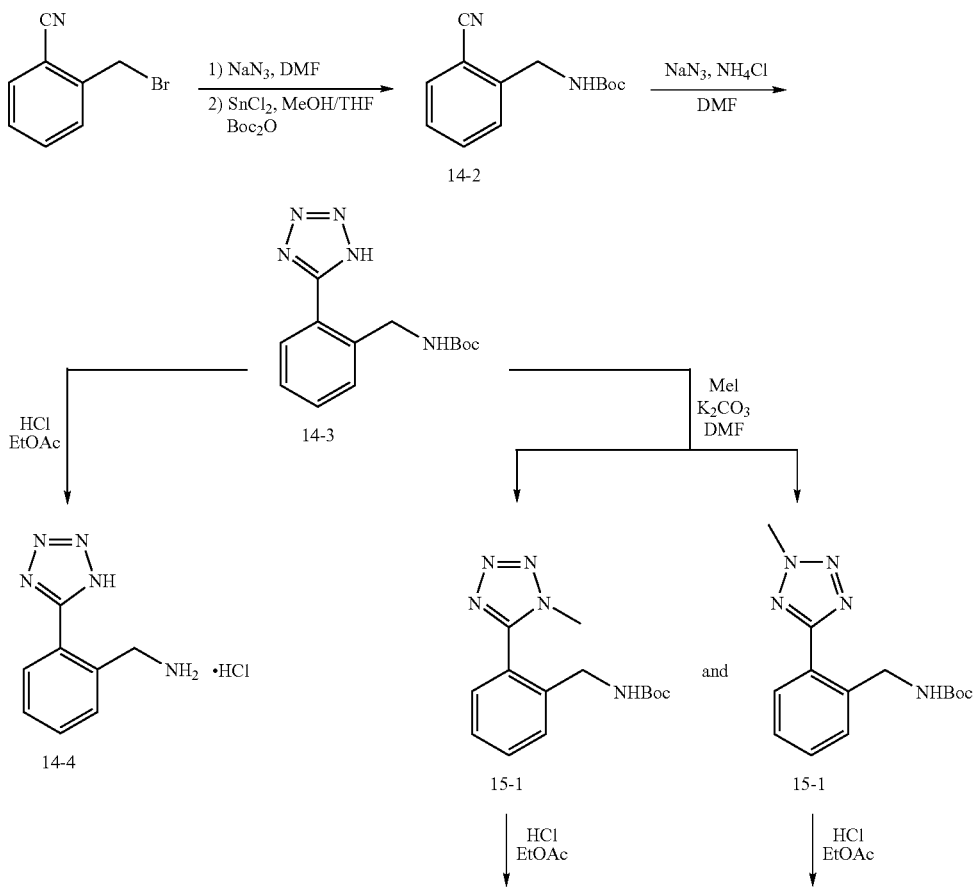

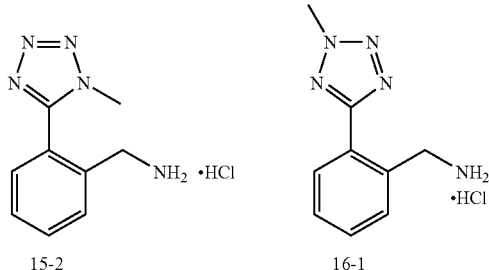

As shown in scheme 11, the synthesis of the 2,2-difluoro-2-pyridin-2-yl-ethylamine, 17-6 involved generation of 2-lithiopyridine from 2-bromopyridine in ether, followed by reaction with diethyl oxalate to give the ketoester, 17-1. Treatment with excess diethylaminosulfurtrifluoride provided the difluoro compound, 17-2 which was reduced using sodium borohydride. The resulting 2,2-difluoro-2-pyridin-2-yl-ethanol was converted to the corresponding triflate using triflic anhydride and 2,6-di-t-butyl-4-methylpyridine as the base. The crude triflate was then treated with sodium azide in DMF to give the azide, 17-5. Reduction of the azide by catalytic hydrogenation provided the 2,2-difluoro-2-pyridin-2-yl-ethylamine, 17-6. The pyridine N-oxide, 18-2 was prepared by treating the azide intermediate, 18-1 with mCPBA and then reducing the azide with triphenylphosphine.

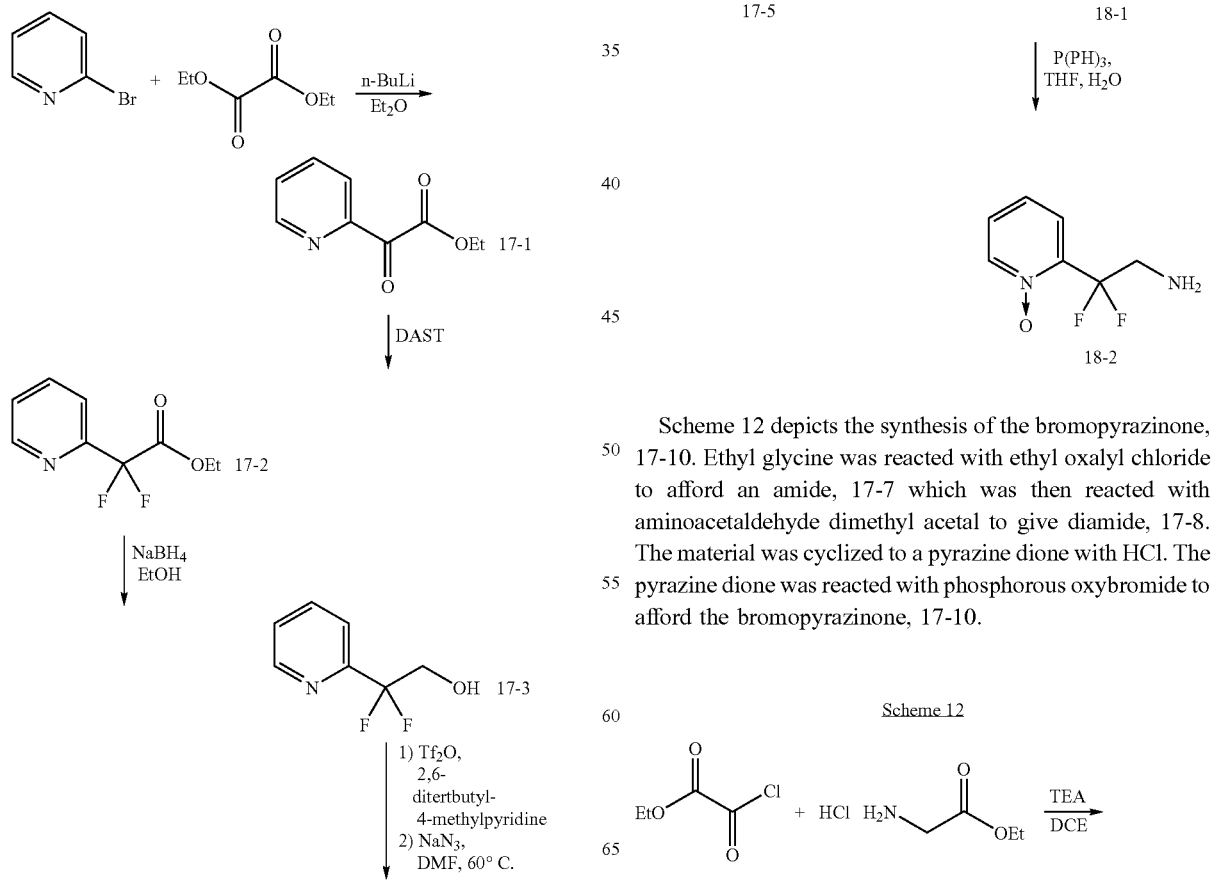

Scheme 12 depicts the synthesis of the bromopyrazinone, 17-10. Ethyl glycine was reacted with ethyl oxalyl chloride to afford an amide, 17-7 which was then reacted with aminoacetaldehyde dimethyl acetal to give diamide, 17-8. The material was cyclized to a pyrazine dione with HCl. The pyrazine dione was reacted with phosphorous oxybromide to afford the bromopyrazinone, 17-10.

Scheme 12

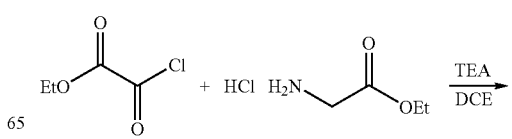

-continued

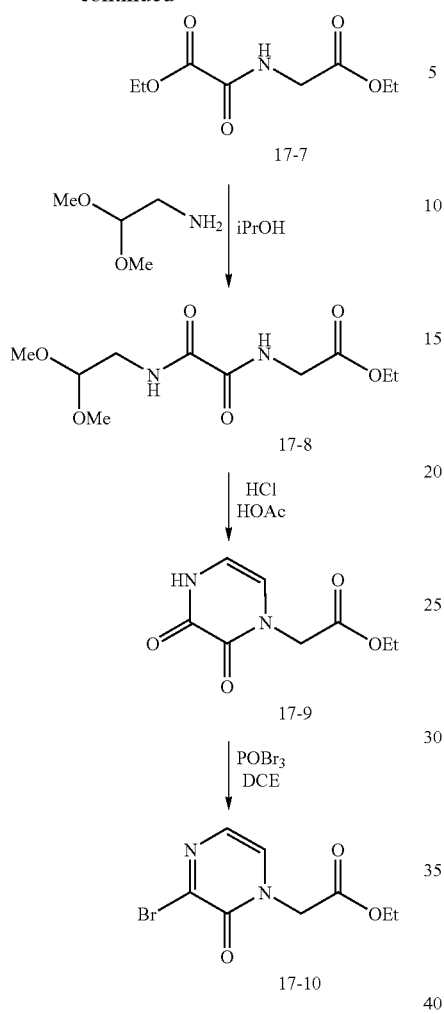

Condensation of the products from schemes 11 and 12 was accomplished by heating in toluene/ethanol. Scheme 13 depicts the reaction with 2,2-difluoro-2-pyridin-2-yl-ethylamine, 17-6 and scheme 14 shows the identical reaction sequence with the N-oxide, 18-2. In both schemes the ethyl esters of the condensed products were hydrolyzed to the carboxylic acids, 19-1 and 20. The pyrazinone ring was chlorinated using N-chlorosuccinimide to give 17-12 and 18-4 which were then hydrolized to the carboxylic acids, 17-13 and 18-5.

Scheme 13

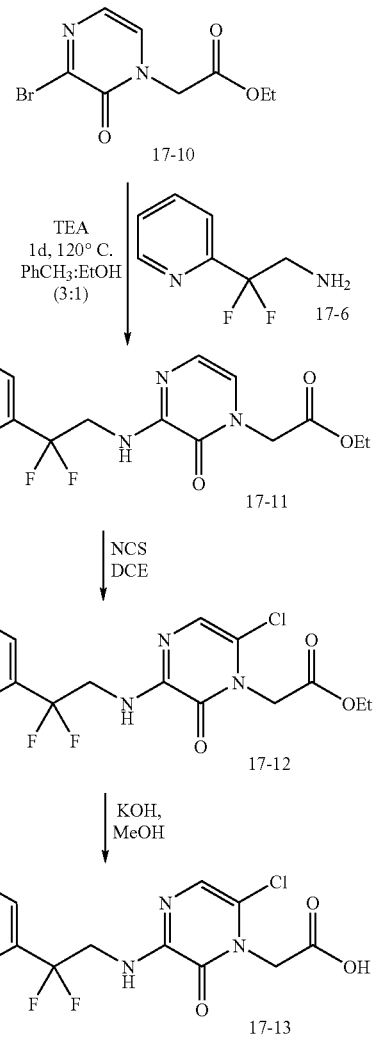

Scheme 14

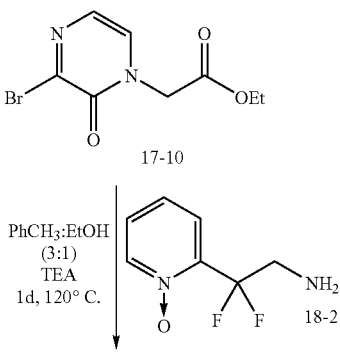

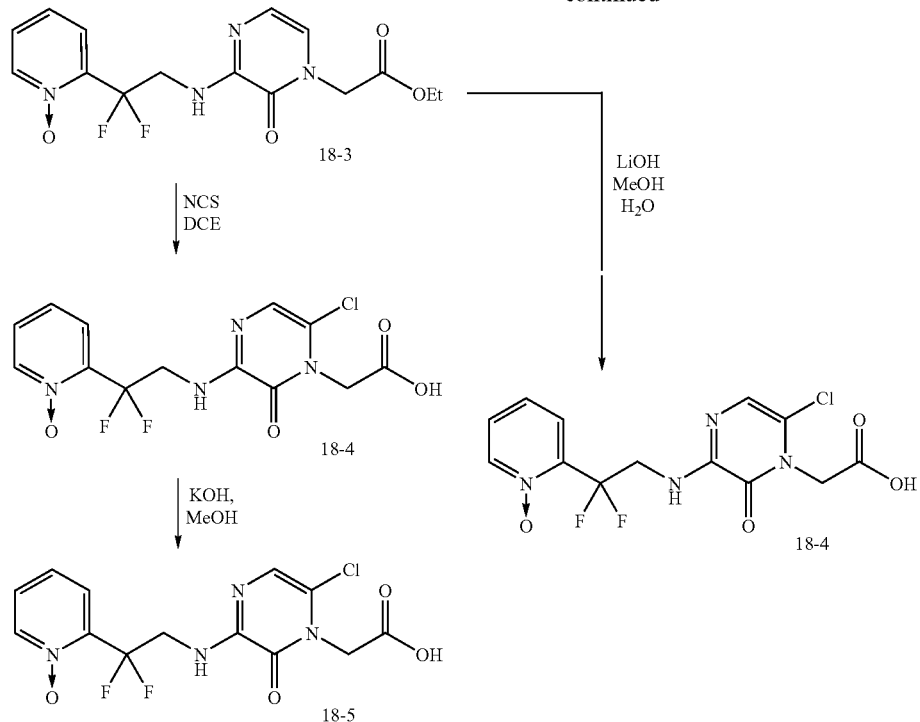

Scheme 15 depicts a reaction sequence leading to a pyrazinone bearing an alkyl cyclopropyl moiety. Cyclopropanecarboxaldehyde was reductively aminated with a Cbz-protected diamine to give 21-1. Protecting group manipulation yielded the Boc-diamine, 21-3. Reaction with the bromo pyrazinone, 17-10 and subsequent hydrolysis of the ethyl ester gave the carboxylic acid, 21-5. Chlorination of the pyrazinone, 21-4 and hydrolysis gave 22-2.

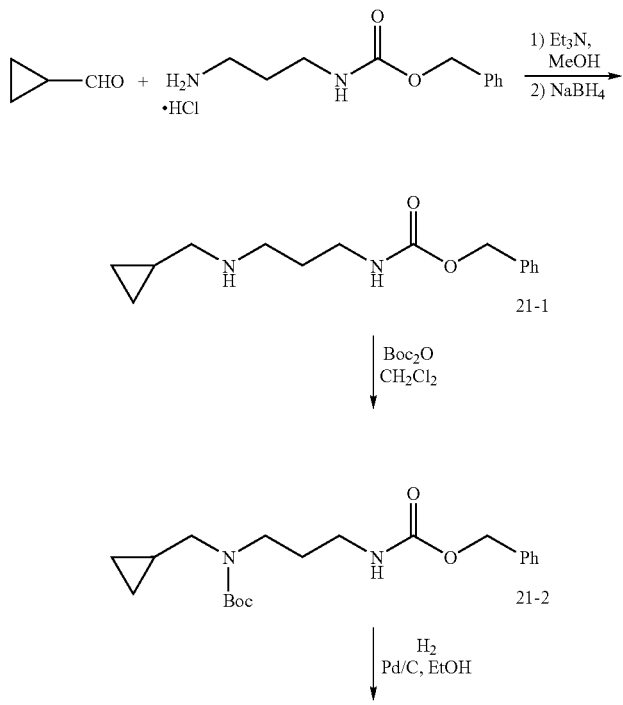

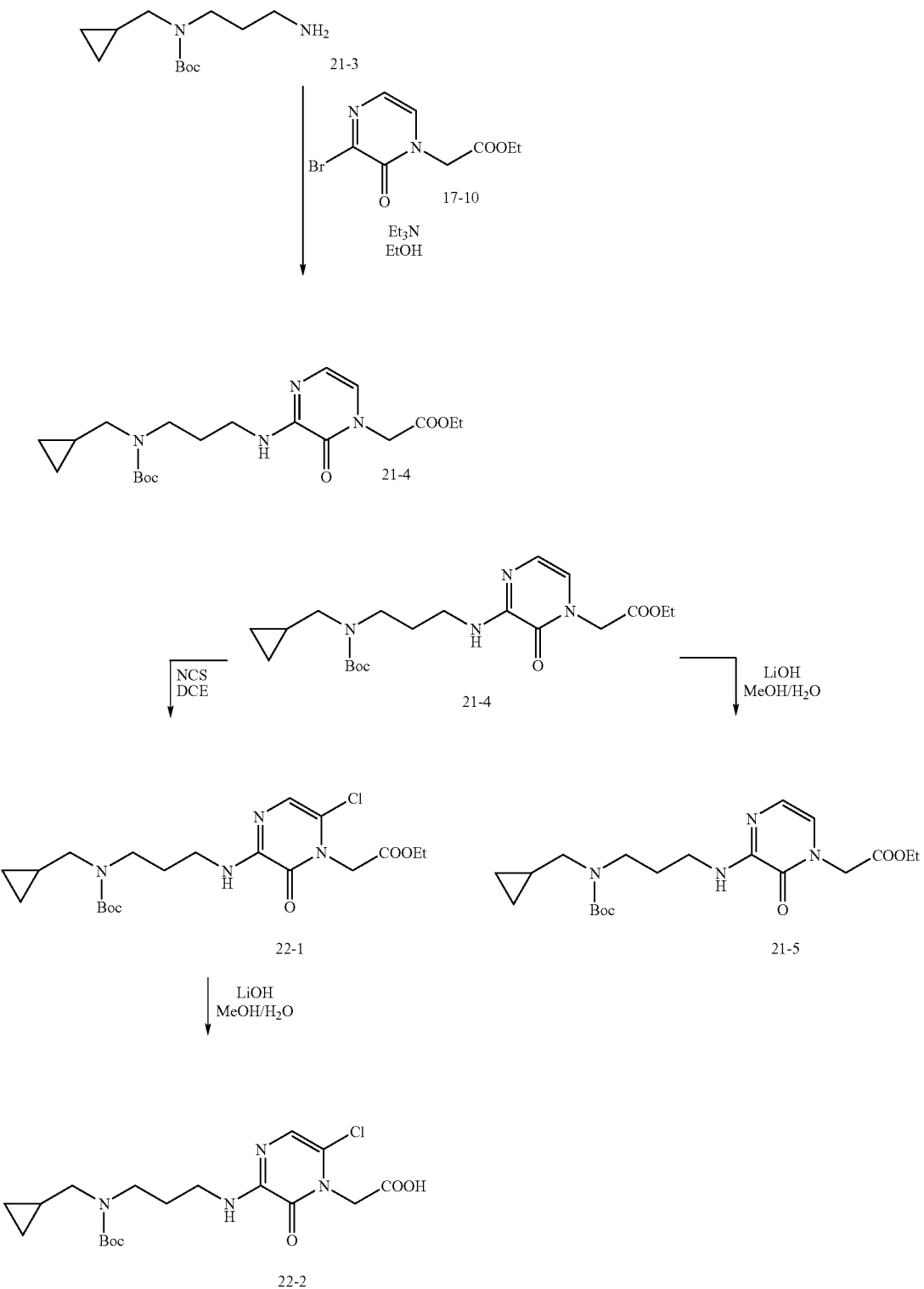
In scheme 16, the bromopyrazinone, 17-10 was reacted with (S)-1-azidomethyl-2-phenyl-ethylamine by heating. Chlorination of the pyrazinone ring and reduction of the azide yielded 23-3. The primary amine was reductively aminated with formaldehyde and the ester was hydrolyzed to give the amino acid pyrazinone, 23-5.

Scheme 16

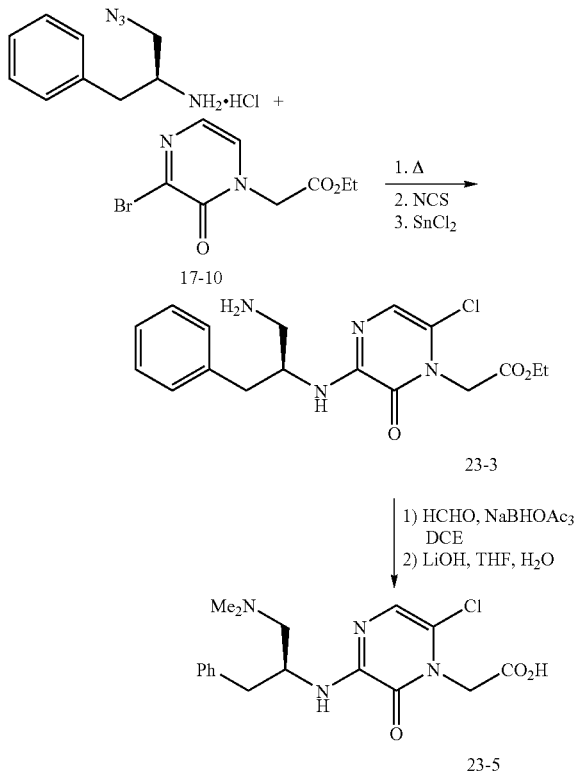

Examples 24 through 63 depict the products resulting from amide couplings between the heterocyclic benzylamines (schemes 1–10, examples 1–16) and the pyrazinone or pyridinone carboxylic acids (schemes 11–16, examples 17–23). A general coupling procedure employed the following reagents: 1-(3-dimethylaminopropyl)-3-ethylcarbodiimide hydrochloride (EDC), 1-hydroxy-7-azabenzotriazole (HOAt) and a tertiary base (diisopropylethylamine, for ex).

EXAMPLE 1

2-[1,2,3]Thiadiazole-4-yl-benzylamine

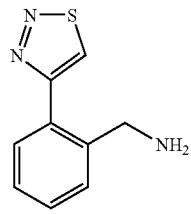

Step A

N'-(1-o-Tolyl-ethylidene)-hydrazinecarboxylic acid ethyl ester (1-1)

A solution of 2'-methylacetophenone (0.98 ml, 7.4 mmol), ethyl carbazate (0.81 g, 7.8 mmol) and p-toluenesulfonic acid monohydrate (70 mg, 0.37 mmol) in toluene (30 ml) was heated at reflux temperature with a Dean-Stark apparatus for 2 h. Solvent evaporation and flash chromatography (silica gel, hexane-ethyl acetate, 80:20) gave N'-(1-o-tolyl-ethylidene)-hydrazinecarboxylic acid ethyl ester; $^1$H NMR (CDCl$_3$, 400 MHz) δ 7.72 (bs, 1H), 7.21 (m, 4H), 4.31 (q, 2H, J=7.1 Hz), 2.37 (s, 3H), 2.17 (s, 3H), 1.34 (t, 3H, J=7.1 Hz).

Step B 4-o-Tolyl-[1,2,3]thiadiazole (1-2)

To thionyl chloride (1 ml), cooled to 0° C. was added N'-(1-o-tolyl-ethylidene)-hydrazinecarboxylic acid ethyl ester. The reaction mixture was heated to 60° C. for 1 h. Solvent evaporation gave 4-o-tolyl-[1,2,3]thiadiazole; $^1$H NMR (CDCl$_3$, 400 MHz) δ 8.51 (s, 1H), 7.65 (d, 1H, J=7.3 Hz), 7.36 (m, 3H), 2.46 (s, 3H).

Step C 4-(2-Bromomethyl-phenyl)-[1,2,3]thiadiazole (1-3)

A solution of 4-o-tolyl-[1,2,3]thiadiazole (100 mg, 0.57 mmol), N-bromosuccinimide (100 mg, 0.57 mmol) and 2,2'-azobisisobutyronitrile (9.4 mg, 0.057 mmol) in chloroform (10 ml) was heated at reflux temperature for ~18 h. Additional chloroform was added and the mixture was washed with water, 5% sodium thiosulfate solution and brine. Drying and solvent evaporation gave 4-(2-bromomethyl-phenyl)-[1,2,3]thiadiazole; $^1$H NMR (CDCl$_3$, 300 MHz) δ 8.87 (s, 1H), 7.67–7.39 (m, 4H), 4.71 (s, 2H).

Step D 4-(2-Azidomethyl-phenyl)-[1,2,3]thiadiazole (1-4)

A solution of 4-(2-bromomethyl-phenyl)-[1,2,3]thiadiazole (7.0 g, 0.027 mol) and sodium azide (5.3 g, 0.081 mol) in N,N-dimethylformamide (200 ml) was stirred at room temperature overnight. Ethyl acetate was added and the reaction mixture was washed with water and brine. Drying and solvent evaporation gave an oil; flash chromatography (silica gel, hexane-ethyl acetate, 96:4) gave 4-(2-azidomethyl-phenyl)-[1,2,3]thiadiazole; $^1$H NMR (CDCl$_3$, 300 MHz) δ 8.74 (s, 1H), 7.76 (m, 1H), 7.53 (m, 3H), 4.54 (s, 2H).

Step E

2-[1,2,3]Thiadiazole-4-yl-benzylamine (1-5)

A solution of 4-(2-azidomethyl-phenyl)-[1,2,3]thiadiazole (1.0 g, 4.6 mmol), triphenylphosphine (1.4 g, 5.5 mmol) and water (0.12 ml, 6.9 mmol) in tetrahydrofuran (20 ml) was stirred at room temperature overnight. Solvent evaporation and flash chromatography (silica gel, chloroform-2-propanol, 95:5–92:8) gave 2-[1,2,3]thiadiazole-4-yl-benzylamine; $^1$H NMR (CDCl$_3$, 300 MHz) δ 8.87 (s, 1H), 7.67 (d, 1H, J=8 Hz), 7.45 (m, 3H), 3.88 (s, 2H).

EXAMPLE 2

2-(1-Trityl-1H-imidazol-4-yl)-benzylamine oxalate salt

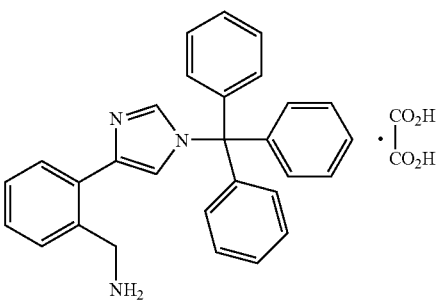

Step A

2-Bromo-1-(2-bromo-phenyl)-ethanone (2-1)

To a solution of 2-bromo-acetophenone (75.0 g, 0.37 mol) in methanol (220 ml) was added trimethyl borate (55 ml, 0.48 mol). This solution was stirred at room temperature under nitrogen for 45 min. Then bromine (20.4 ml, 0.39 mol) was added dropwise over 2 h. The reaction temperature was closely monitored and maintained between 23 to 27° C. Below 23° C. product formation was slow and above 27° C. there was significant dibromoketone formation. The reaction was stirred for an additional 1 h. At this point the reaction consisted of a mixture of 2-bromo-1-(2-bromo-phenyl)ethanone and the dimethylketal as the major products (by GC). Water (220 ml) was added and the mixture was heated to reflux ~74° C. for 40 min. After cooling, two phases separated. Concentration of the bottom layer afforded a yellow oil as the product. This oil was used for the next step without further purification.

Step B 4-(2-Bromo-phenyl)-1H-imidazole (2-2)

To a 1 liter, three neck flask containing 2-bromo-1-(2-bromo-phenyl)-ethanone (95 g, 340 mmol) was added formamide (240.0 ml, 6.8 mol). The resulting two phase mixture was heated to 145° C. for 14 h under nitrogen. At this temperature the reaction solution was homogeneous. The progress of the reaction was monitored by TLC (silica gel, ethyl acetate), product $R_f$=0.23. After cooling, the reaction was diluted with ethyl acetate (500 ml). To this solution was added 15% aqueous potassium carbonate solution (440 ml) in portions while stirring. The phases that formed were separated. The aqueous layer was extracted with ethyl acetate (175 ml×2). The combined organic layer was then washed with brine (50 ml×2), dried (sodium sulfate) and concentrated in vacuo to yield an amber solid.

Step C 4-(2-Bromo-phenyl)-1-trityl-1H-imidazole (2-3)

To a solution of crude 4-(2-bromo-phenyl)-1H-imidazole (73.5 g, 0.33 mol) and triethylamine (45.8 ml, 0.33 mol) in dry dimethylformamide (750 ml) at 0° C. was added a solution of trityl chloride in dry dimethylformamide (850 ml) dropwise over 40 min. When the addition was complete, the ice bath was removed and the reaction was stirred at room temperature for 1.5 h. Then the reaction mixture was poured into a stirring mixture of ice water (ca. 2.0 L). A light orange solid precipitated. After stirring for 20 min the solid was filtered and dried to give a light amber solid. This solid was used in the next reaction without further purification.

Step D 2-(1-Trityl-1H-imidazol-4-yl)-benzonitrile (2-4)

To a solution of 4-(2-bromo-phenyl)-1-trityl-1H-imidazole (73.0 g, 163.3 mmol) in dimethylformamide (500 ml) was added copper (I) cyanide (17.5 g, 195.9 mmol). The reaction was heated to ~80° C. under nitrogen for 14 h. After cooling to about 50° C., the reaction was diluted with toluene (ca. 300 ml) and slowly poured onto ammonium hydroxide (3N, 1.5 L) while stirring vigorously. The mixture was stirred for 40 min and then filtered in vacuo over a bed of celite (slow filtration, required ~2 h). The phases were separated and the organic layer was washed with brine (75 ml×3) and dried (sodium sulfate). Concentration of the solvent afforded a light brown solid. The crude product contains ~10–15% of trityl alcohol (by HPLC) and was used without further purification in the subsequent step.

Step E 2-(1-Trityl-1H-imidazol-4-yl)-benzylamine (2-5)

2-(1-Trityl-1H-imidazol-4-yl)-benzonitrile (17.6 g, 42.7 mmol) was dissolved in dry tetrahydrofuran (320 ml) and stirred under nitrogen in an ice bath. To this solution was added lithium aluminum hydride (1.0 M in THF, 45 ml, 45 mmol) dropwise over 15 min. After the addition was complete the ice bath was removed and the reaction was stirred at room temperature. The reaction was closely monitored by HPLC and was typically complete within 45 min to 1.5 h. This close monitoring was essential because with longer reaction times, the amount of deprotected imidazole increased. Once complete, the reaction was diluted with tetrahydrofuran (200 ml) and quenched with water (1.7 ml), 15% sodium hydroxide solution (1.7 ml) and water (5.1 ml). This mixture was stirred at room temperature for 3 h. The solid was filtered over a layer of celite and rinsed with tetrahydrofuran (200 ml). Rotary evaporation of the filtrate afforded 2-(1-trityl-1H-imidazol-4-yl)-benzylamine as a thick amber oil.

Step F 2-(1-Trityl-1H-imidazol-4-yl)-benzylamine oxalate salt (2-6)

The crude 2-(1-trityl-1H-imidazol-4-yl)-benzylamine (66.1 g, 159 mmol) was dissolved in tetrahydrofuran (420 ml). Solid oxalic acid (14.3 g, 159 mmol) was added to the solution while stirring. This mixture was stirred at room temperature for 15 min and then added dropwise to stirring hexane (2000 ml). Tetrahydrofuran (100 ml) was used to rinse the glassware. A yellow solid precipitated. The mixture was stirred for an additional 20 min and the product was isolated by filtration. The solid was rinsed with 4:1 hexane: tetrahydrofuran (625 ml) and dried in a vacuum oven at ~45° C. with an air purge for 18 h to afford 2-(1-trityl-1H-imidazol-4-yl)-benzylamine oxalate salt; MS (ES+) M+1 416.6 for $C_{29}H_{25}N_3$.

EXAMPLE 3

2-Tetrazol-1-yl-benzylamine

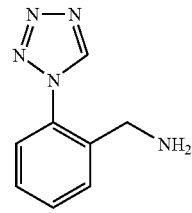

Step A

2-Tetrazol-1-yl-benzoic acid (3-1)

A suspension of 2-aminobenzoic acid (6.0 g, 0.044 mol), trimethyl orthoformate (14.2 ml, 0.13 mol) and sodium azide (8.4 g, 0.13 mol) in glacial acetic acid (150 ml) was stirred at room temperature for 2 h. Filtration and concentration from toluene gave 2-tetrazol-1-yl-benzoic acid; $^1$H NMR (CD$_3$OD, 400 MHz) δ 9.47 (s, 1H), 8.19 (dd, 1H, J=7.7 Hz, J=1.6 Hz), 7.79 (m, 2H), 7.61 (dd, 1H, J=7.7 Hz, J=1.5 Hz).

Step B

2-Tetrazol-1-yl-benzamide (3-2)

A solution of 2-tetrazol-1-yl-benzoic acid (1.0 g, 5.2 mmol), ammonium chloride (0.56 g, 10.4 mmol), 1-(3-dimethylaminopropyl)-3-ethylcarbodiimide hydrochloride (2.0 g, 10.4 mmol), 1-hydroxy-7-azabenzotriazole (1.4 g, 10.4 mmol) and diisopropylethylamine (3.6 ml, 20.8 mmol) in N,N-dimethylformamide (15 ml) was stirred at room temperature overnight. Water was added and the reaction mixture was extracted with ethyl acetate. The combined organic layers were washed with brine. Drying and solvent evaporation gave 2-tetrazol-1-yl-benzamide; $^1$H NMR (CD$_3$OD, 400 MHz) δ 9.44 (s, 1H), 7.72 (m, 4H).

Step C

2-Tetrazol-1-yl-benzonitrile (3-3)

To a solution of 2-tetrazol-1-yl-benzamide (1.5 g, 7.9 mmol) in tetrahydrofuran (50 ml) was added (methoxycarbonylsulfamoyl)ammonium hydroxide, inner salt (2.8 g, 11.8 mmol) in three portions over 1.5 h. Water was added and the reaction mixture was extracted with ethyl acetate. The combined organic layers were washed with brine. Drying and solvent evaporation gave 2-tetrazol-1-yl-benzonitrile; $^1$H NMR (CDCl$_3$, 400 MHz) δ 9.27 (s, 1H), 7.90 (m, 3H), 7.72 (m, 1H).

Step D

2-Tetrazol-1-yl-benzylamine (3-4)

A solution of 2-tetrazol-1-yl-benzonitrile (1.3 g, 7.6 mmol) in ethanol saturated with ammonia (125 ml) was stirred in the presence of Raney nickel (50% slurry in water, washed with ethanol, catalytic amount) under a hydrogen atmosphere overnight. The reaction mixture was filtered over celite and concentrated to give 2-tetrazol-1-yl-benzylamine; $^1$H NMR (CDCl$_3$, 400 MHz) δ 9.28 (s, 1H), 7.59 (m, 2H), 7.47 (m, 2H), 3.70 (s, 2H).

EXAMPLE 4

5-Chloro-2-tetrazol-1-yl-benzylamine (4)

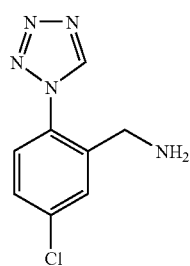

Prepared following a similar protocol as described in Example 3,2-amino-5-chloro-benzoic acid was converted to 5-chloro-2-tetrazol-1-yl-benzylamine. $^1$H NMR (CDCl$_3$, 400 MHz) δ 9.24 (s, 1H), 7.64 (d, 1H, J=2.2 Hz), 7.46 (m, 1H), 7.38 (m, 1H), 3.68 (s, 2H).

EXAMPLE 5

2-Pyrazol-1-yl-benzylamine trifluoroacetic acid salt

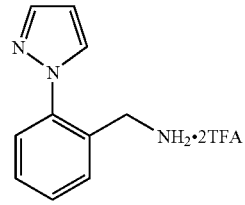

Step A

2-Pyrazol-1-yl-benzoic acid (5-1)

To a vigorously stirred mixture of 2-hydrazinobenzoic acid hydrochloride (50 g, 0.27 mol) and malonaldehyde bis-dimethylacetal (43 ml, 0.27 mol) in water (630 ml) was gradually added conc. HCl (30 ml). The reaction mixture was refluxed for 2 h and methanol was evaporated. The inorganic layer was treated with charcoal until colorless, cooled, left for 2 h and filtered. The residue was washed with cold water and dried in the air to give 2-pyrazol-1-yl-benzoic acid; MS (ES+) M+1 189.4 for $C_{10}H_8N_2O_2$.

Step B

2-Pyrazol-1-yl-benzamide (5-2)

A solution of 2-pyrazol-1-yl-benzoic acid (50 mg, 0.26 mmol), ammonium chloride (28 mg, 0.52 mmol), 1-(3-dimethylaminopropyl)-3-ethylcarbodiimide hydrochloride (100 mg, 0.52 mmol), 1-hydroxy-7-azabenzotriazole (71 mg, 0.52 mmol) and diisopropylethylamine (0.17 ml, 1.0 mmol) in N,N-dimethylformamide (0.75 ml) was stirred at room temperature for 5 h. Water was added and the reaction mixture was extracted with ethyl acetate. Drying and solvent evaporation gave 2-pyrazol-1-yl-benzamide; $^1$H NMR (CD$_3$OD, 400 MHz) δ 7.92 (d, 1H, J=2.4 Hz), 7.70–7.48 (m, 5H), 6.49 (m, 1H).

Step C

2-Pyrazol-1-yl-benzylamine trifluoroacetic acid salt (5-3)

A solution of 2-pyrazol-1-yl-benzamide (68 mg) and borane-tetrahydrofuran complex (1M solution in tetrahydrofuran, 1.4 ml, 1.4 mmol) in tetrahydrofuran (2 ml) was heated at reflux temperature for 2 h. Hydrochloric acid (1M solution in water, 2.8 ml) was added and the reaction mixture was heated at reflux temperature for 30 minutes. The solution was neutralized with 1N sodium hydroxide, concentrated to remove tetrahydrofuran and extracted with chloroform. Drying and solvent evaporation gave an oil; purification by reverse phase preparative HPLC (5% to 95% CH$_3$CN in water containing 0.1% TFA, C18 PRO YMC 20×150 mm) gave 2-pyrazol-1-yl-benzylamine trifluoroacetic acid salt; $^1$H NMR (CDCl$_3$, 400 MHz) δ 8.80 (bs, 2H), 7.80 (m, 2H), 7.62–7.37 (m, 4H), 6.56 (t, 1H, J=2.2 Hz), 4.07 (s, 2H).

EXAMPLE 6

2-(1H-Imidazol-2-yl)-benzylamine

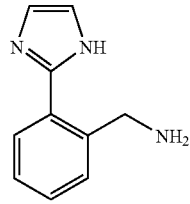

Step A

2-Cyano-benzimidic acid ethyl ester hydrochloride (6-1)

A suspension of phthalonitrile (70 g, 0.55 mol) in ethanol (100 ml) and chloroform (200 ml) was warmed and then cooled to 0° C. The reaction mixture was saturated with HCl (g) and then aged at 0° C. for 2 weeks. The resultant precipitate was filtered and washed with chloroform. Dilution of the filtrate with ether produced additional 2-cyano-benzimidic acid ethyl ester hydrochloride.

Step B 2-(1H-Imidazol-2-yl)-benzonitrile hydrochloride (6-2)

A solution of 2-cyano-benzimidic acid ethyl ester hydrochloride (43 g, 0.20 mol) and 2,2-diethoxy-ethylamine (30 ml, 0.21 mol) in methanol (430 ml) was aged at room temperature for 1 h. The reaction mixture was concentrated to remove methanol and conc. sulfuric acid (110 ml) was added. After heating on a steam bath for 1.5 h, the reaction mixture was diluted with water (700 ml) and extracted with chloroform. The aqueous phase was made strongly basic with sodium hydroxide and extracted with chloroform. hydrochloric acid (12N) was added to give pH 3–4, tar was filtered and the filtrate was concentrated. The resultant brown solid was sublimed at 200–220° C. The purified solid was dissolved in hydrochloric acid solution (6N, 110 ml), byproducts filtered and the filtrate concentrated. The residue was diluted with ethanol (100–120 ml) containing hydrochloric acid (12N, 1 ml), boiled briefly and filtered. Further concentration and cooling of the filtrate gave 2-(1H-imidazol-2-yl)benzonitrile hydrochloride (1.5 g). The filtrate was concentrated further and diluted with acetone. Filtration gave 2-(1H-imidazol-2-yl)-benzoic acid hydrochloride (7.3 g). Dilution of the filtrate with acetone and filtration of the resultant solid gave additional 2-(1H-imidazol-2-yl)-benzonitrile hydrochloride; mp 200–204° C.; IR 4.5 μ.

Step C 2-(1H-Imidazol-2-yl)-benzonitrile (6-3)

To a solution of 2-(1H-imidazol-2-yl)-benzonitrile hydrochloride (3 g, 0.014 mol) in water (20 ml) was added sodium hydroxide solution (2.5 N, 5 ml). Filtration of the resultant precipitate and recrystallization from ethyl acetate gave 2-(1H-imidazol-2-yl)-benzonitrile; Anal. Calcd. For $C_{10}H_7N_3$: C, 70.99; H, 4.17; N, 24.84. Found: C, 70.74; H, 4.08; N, 25.24.

Step D 2-(1H-Imidazol-2-yl)-benzylamine (6-4)

A solution of 2-(1H-imidazol-2-yl)-benzonitrile (50 mg, 0.30 mmol) in ethanol saturated with ammonia (5 ml) was stirred in the presence of Raney nickel (50% slurry in water, washed with ethanol, catalytic amount) under a hydrogen atmosphere for 2 h. The reaction mixture was filtered over celite and concentrated to give 2-(1H-imidazol-2-yl)-benzylamine; $^1$H NMR (CDCl$_3$, 400 MHz) δ 8.13 (d, 1H, J=7.5 Hz), 7.42 (m, 1H), 7.28 (m, 2H), 7.18 (bs, 2H), 3.96 (s, 2H).

EXAMPLE 7

C-(3-[1,2,4]Triazol-1-yl-pyridin-2-yl)-methylamine hydrochloride salt

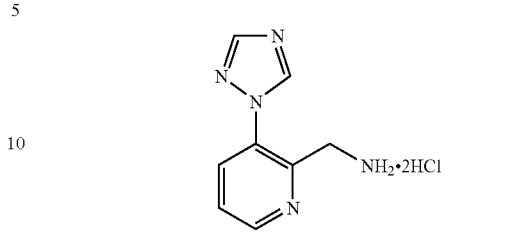

Step A

3-[1,2,4]Triazol-1-yl-pyridine-2-carbonitrile (7-1)

To a solution of 2-cyano-3-fluoro-pyridine (2.99 g, 24.49 mmol, preparation described in Sakamoto et. al., Chem. Pharm. Bull. 1985, 33(2), 565–571) in DMF (30 ml) is added cesium carbonate (2.03 g, 29.39 mmol) and 1,2,4-triazole (2.03 g, 29.39 mmol) and the reaction mixture is stirred at 65° C. for 4 h. After cooling to room temperature, the mixture is diluted with water and extracted with EtOAc 3 times. The aqueous layer is saturated with LiCl and further extracted with EtOAc. The combined organic layer is dried on sodium sulfate, concentrated in vacuo. The crude product is purified by flash chromatography (silica gel, 2% MeOH containing 10% NH$_4$OH in CH$_2$Cl$_2$ to 6%) to give 3-[1,2,4]triazol-1-yl-pyridine-2-carbonitrile. $^1$H NMR (CDCl$_3$, 400 MHz) δ 8.95 (s, 1H); 8.8 (d, J=4 Hz, 1H); 8.24 (s, 1H); 8.22 (d, J=8.5 Hz, 1H); 7.75 (dd, J=4, 8.5 Hz, 1H).

Step B (3-[1,2,4]Triazol-1-yl-pyridin-2-ylmethyl)-carbamic acid tert-butyl ester (7-2)

To a suspension of Raney Nickel (ca. 3 pipets of suspension in water, washed/decanted with EtOH several times) in MeOH saturated with NH$_3$ (200 ml) was added 3-[1,2,4]triazol-1-yl-pyridine-2-carbonitrile (3.745 g, 21.88 mmol). The mixture was hydrogenated at 55 Psi for 18 h. The reaction mixture was filtered on celite under a flow of argon and the filtrate was concentrated in vacuo. To a solution of the crude material in CH$_2$Cl$_2$ (100 ml) and MeOH (10 ml) was added di-tert-butyl dicarbonate (6.2 g, 28.4 mmol) and the reaction mixture was stirred at room temperature for 30 min. The crude product obtained by concentration in vacuo is purified by flash chromatography (silica gel, 2% MeOH containing 10% NH$_4$OH in CH$_2$Cl$_2$ to 6%) to give (3-[1,2,4]triazol-1-yl-pyridin-2-ylmethyl)-carbamic acid tert-butyl ester. $^1$H NMR (CDCl$_3$, 400 MHz) δ 8.72 (d, J=4.8 Hz, 1H); 8.42 (s, 1H); 8.18 (s, 1H); 7.70 (d, J=7.6 Hz, 1H); 7.40 (dd, J=4.8, 7.6 Hz, 1H); 5.85 (bs, 1H); 4.43 (d, J=5.4 Hz, 2H); 1.45 (s, 9H).

Step C

C-(3-[1,2,4]Triazol-1-yl-pyridin-2-yl)-methylamine hydrochloride salt (7-3)

Through a solution of (3-[1,2,4]triazol-1-yl-pyridin-2-ylmethyl)-carbamic acid tert-butyl ester (4.08 g) in CH$_2$Cl$_2$ (100 ml) and MeOH (20 ml) cooled to 0° C. was bubbled HCl (g) for 10 min. The flask was sealed and the reaction mixture was stirred at room temperature for 18 h. Nitrogen was bubbled through the reaction mixture for 5 min and the reaction mixture was concentrated to give C-(3[1,2,4]triazol-1-yl-pyridin-2-yl)-methylamine hydrochloride salt as a white solid. $^1$H NMR (CD$_3$OD, 400 MHz) δ 9.67 (s, 1H); 8.85 (d, J=5.3 Hz, 1H); 8.72 (s, 1H); 8.18 (d, J=8 Hz, 1H); 7.7 (dd, J=5.3, 8 Hz, 1H); 4.45 (s, 2H).

EXAMPLE 8

5-Chloro-2-[1.2.4]triazol-1-yl-benzylamine

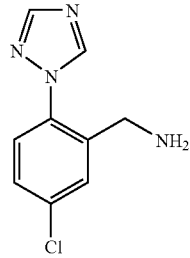

Step A

5-Chloro-2-[1,2,4]triazol-1-yl-benzonitrile (8-1)

To a solution of 2,5-dichlorobenzonitrile (10 g, 58.1 mmol) in DMF (100 ml) was added cesium carbonate (22.7 g, 69.8 mmol) and 1,2,4-triazole (4.8 g, 69.8 mmol) and the reaction mixture was stirred at 65° C. for 5.5 h, at 75° C. for 16 h, at 85° C. for 7 h. More 1,2,4-triazole (5 g) was added and the reaction mixture was stirred at 85° C. for 18 h and at 100° C. for 4 h. After cooling to room temperature, the mixture was diluted with water and extracted with EtOAc 3 times. The combined organic layer was washed with aqueous LiCl, dried on sodium sulfate, concentrated in vacuo to give 5-chloro-2-[1,2,4]triazol-1-yl-benzonitrile as a white solid which was used in the next step without further purification.

Step B

5-Chloro-2-[1,2,4]triazol-1-yl-benzylamine (8-2)

To a suspension of 5-chloro-2-[1,2,4]triazol-1-yl-benzonitrile (11.87 g, 58 mmol) in EtOH saturated with $NH_3$ (500 ml) was added Raney Nickel (ca. 5 pipets of suspension in water, washed/decanted with EtOH several times). The mixture was hydrogenated at 1 atm for 26 h. The reaction mixture was filtered on celite under a flow of argon and the filtrate was concentrated in vacuo. The crude product was purified by flash chromatography (silica gel, 5% MeOH containing 10% $NH_4OH$ in $CH_2Cl_2$ to 10%) to give 5-chloro-2-[1,2,4]triazol-1-yl-benzylamine as a white solid. $^1H$ NMR ($CDCl_3$, 400 MHz) δ 8.47 (s, 1H); 8.14 (s, 1H); 7.58 (d, J=2.3 Hz, 1H); 7.38 (dd, J=2.3, 7.9 Hz, 1H); 7.30 (d, J=7.9 Hz, 1H); 3.70 (s, 2H). 8.72 (d, J=4.8 Hz, 1H); 8.42 (s, 1H); 8.18 (s, 1H); 7.70 (d, J=7.6 Hz, 1H); 7.40 (dd, J=4.8, 7.6 Hz, 1H); 5.85 (bs, 1H); 4.43 (d, J=5.4 Hz, 2H); 1.45 (s, 9H).

EXAMPLE 9

2-(1,2,4-Triazol-1-yl)benzylamine

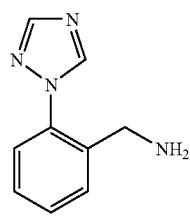

Step A 2-(1,2,4-Triazol-1-yl)cyanobenzene (9-1)

To a stirred solution of 2-fluorocyanobenzene (5.0 g, 41 mmol) in DMF (75 mL) was added 1,2,4-triazole (3.0 g, 43 mmol) and cesium carbonate (14 g, 43 mmol). The mixture was warmed to 50° C. and stirred under inert atmosphere for 18 h. The mixture was cooled to ambient temperature, diluted with an equal volume of EtOAc, filtered, and the filtrate solvents were removed under reduced pressure. The residue was partitioned between ether (50 mL) and water (100 mL). The undissolved solid was collected by suction filtration and dried under reduced pressure to give 4.6 g of a 10:1 mixture of 2-(1,2,4-triazol-1-yl)cyanobenzene (hplc retention time=2.29 min, 5% to 100% $CH_3CN$ in water containing 0.1% TFA, Zorbax C8, 4.6 mm ID×7.5 cm, 3.5 micron; TLC Rf=0.6, EtOAc) and 2-(1,2,4-triazol-4-yl)cyanobenzene (hplc retention time=1.91 min, 5% to 100% $CH_3CN$ in water containing 0.1% TFA, Zorbax C8, 4.6 mm ID×7.5 cm, 3.5 micron; TLC Rf=0.1, EtOAc). The mixture was separated by flash chromatography using a gradient elution of 0:100 to 5:95 MeOH:EtOAc to give 2-(1,2,4-triazol-1-yl)cyanobenzene ($^1H$ NMR (DMSO-$d_6$) δ 9.19 (s, 1H), 8.37 (s, 1H), 8.10 (d, J=7.6 Hz, 1H), 7.96–7.87 (m, 2H), 7.71 (t, J=7.7 Hz, 1H); mass spec m/z=171 ($M^++H$)) and 2-(1,2,4-triazol-4-yl)cyanobenzene ($^1H$ NMR (DMSO-$d_6$) δ 9.03 (s, 2H), 8.13 (d, J=7.6 Hz, 1H), 7.93 (t, J=7.8 Hz, 1H), 7.80 (d, J=7.8 Hz, 1H), 7.74 (t, J=7.7 Hz, 1H); mass spec m/z=171 ($M^++H$)), both as white solids.

Step B 2-(1,2,4-Triazol-1-yl)-benzylamine (9-2)

A solution of 2-(1,2,4-triazol-1-yl)cyanobenzene (508 mg, 2.99 mmol) and 25% by weight of palladium on carbon, 10% catalyst (134 mg) in ethanol (75 ml) was placed on a PARR hydrogenation Apparatus under a hydrogen atmosphere at 55 psi. overnight. The mixture was filtered through celite and concentrated to give 2-(1,2,4-triazol-1-yl)-benzylamine; $^1H$ NMR ($CD_3OD$) δ 8.80 (s, 1H), 8.22 (s, 1H), 7.64–7.43 (m, 4H), 3.66 (s, 2H).

EXAMPLE 10

2-(1,2,4-Triazol-4-yl)benzylamine

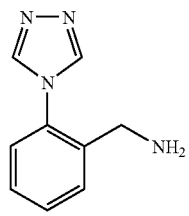

Step A 2-(1,2,4-Triazol-4-yl)benzylamine (10-1)

2-(1,2,4-Triazol-4-yl)cyanobenzene (0.3 g; 1.76 mmol) from step A of example 9 was combined with 30% by weight of palladium on carbon, 10% catalyst (100 mg) in ethanol (75 ml) and placed on a PARR hydrogenation apparatus under a hydrogen atmosphere at 55 psi. for 48 hours. The mixture was filtered through celite and concentrated to give 2-(1,2,4-triazol-4-yl)benzylamine; $^1H$ NMR ($CD_3OD$) δ 8.77 (s, 2H), 7.69–7.59 (m, 4H), 3.61 (s, 2H).

EXAMPLE 11

3-(Tetrazol-1-yl)-2-aminomethylpyridine

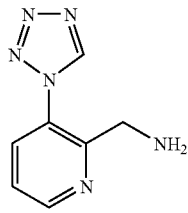

Step A 3-(Tetrazol-1-yl)cyanopyridine (11-1)

To a stirred solution of tetrazole (1.0 g, 14 mmol) in DMF (150 mL) was added 40% aqueous tetrabutylammonium hydroxide (7.8 g, 12 mmol). The solvent was removed under reduced pressure. To ensure removal of all the water from the tetrabutylammonium hydroxide solution, the residue was redissolved in DMF and the solution was evaporated under reduced pressure. This procedure was repeated a total of three times. The residue was then dissolved in DMF (60 mL) and 2-cyano-3-fluoro-pyridine (1.5 g, 12 mmol, preparation described in Sakamoto et. al., *Chem. Pharm. Bull.* 1985, 33(2), 565–571) was added. The reaction was stirred at ambient temperature under inert atmosphere for four days, at which time hplc analysis indicated about 65% conversion of the 3-fluoro-2-cyanopyridine to new products. The solvent was removed under reduced pressure and the residue was partitioned between EtOAc and water. The EtOAc layer was separated, dried over anhydrous $MgSO_4$, and filtered. The solvent was removed under reduced pressure and the residue was purified by flash chromatography using a gradient elution of 1:4 to 100:0 EtOAc:hexanes to give 3-(tetrazol-1-yl)cyanopyridine as a white crystalline solid (TLC Rf=0.5, 1:1 EtOAc-hexanes; hplc retention time=2.04 min, 5% to 100% $CH_3CN$ in water containing 0.1% TFA, Zorbax C8, 4.6 mm ID×7.5 cm, 3.5 micron); $^1$H NMR ($CDCl_3$) δ 9.42 (s, 1H), 8.94 (dd, J=1.3, 4.6 Hz, 1H), 8.31 (dd, J=1.3, 8.4 Hz, 1H), 7.87 (dd, J=4.6, 8.4 Hz, 1H).

Step B 3-(Tetrazol-1-yl)-2-aminomethylpyridine (11-2)

A solution of 3-(tetrazol-1-yl)cyanopyridine (250 mg, 1.45 mmol) and 45% by weight of palladium on carbon, 10% catalyst (110 mg) in ethanol (75 ml) was placed on a PARR hydrogenation Apparatus under a hydrogen atmosphere at 55 psi. overnight. The mixture was filtered through celite and concentrated to give 3-(tetrazol-1-yl)-2-aminomethylpyridine; $^1$H NMR (CD3OD) δ 9.60 (s, 1H), 8.83–8.81 (m, 1H), 7.99–7.97 (m, 1H), 7.59–7.56 (m, 1H), 3.77 (s, 2H).

EXAMPLE 12

2-(1H-Pyrazol-3-yl)-benzylamine hydrochloride salt

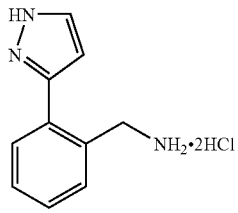

Step A 1-(Tetrahydro-pyran-2-yl)-1H-pyrazole (12-1)

To pyrazole (14.3 g, 0.21 mol) was added 3,4-dihydro-2H-pyran (29 ml, 0.315 mol) and, after complete dissolving, trifluoroacetic acid (0.1 ml, 0.0013 mol) was added to the obtained solution. The reaction mixture was refluxed for 5 h, sodium hydride (0.2 g, 0.008 mol) was added, and the mixture was distilled to give 1-(tetrahydro-pyran-2-yl)-1H-pyrazole; b.p. ~60–65° C./0.5–1 torr.

Step B

1H-Pyrazol-3-ylboronic acid (12-2)

To a solution of 1-(tetrahydro-pyran-2-yl)-1H-pyrazole (7.61 g, 0.0525 mol) in dry THF (50 ml), a 1.6M hexane solution of BuLi (33 ml) was added dropwise at −70° C. A white bulky precipitate formed immediately. Triisopropyl borate (12.7 ml, 0.055 mol) was added over 10 min at the same temperature (−70° C.), and kept at this temperature for 1 h. Then the mixture was decomposed with 2 eq. of 2M HCl under intensive stirring to give a white bulky precipitate. During decomposition, the temperature rose from −70° C. to 20° C. The precipitate was filtered off, washed with water and benzene (until the disappearance of a typical smell) to give 1H-pyrazol-3-ylboronic acid; $^1$H NMR ($D_2O$) δ 7.47 (d, 1H), 6.20 (d, 1H).

Step C tert-Butyl-2-bromobenzylcarbamate (12-3)

To a solution of 2-bromobenzylamine hydrochloride (11.12 g, 0.05 mol) in dimethylformamide (50 ml) was added di-tert-butyl dicarbonate (10.91 g, 0.05 mol) and triethylamine (3.66 ml, 0.05 mol). The reaction mixture was stirred at room temperature overnight. Saturated sodium carbonate solution was added and the mixture was extracted with ethyl acetate. The combined organic layers were washed with brine. Drying and solvent evaporation gave tert-butyl-2-bromobenzylcarbamate; MS (ES+) M+1 286.4 for $C_{12}H_{16}BrNO_2$.

Step D tert-Butyl-2-(1H-pyrazol-3-yl)benzylcarbamate (12-4)

To a solution of 1H-pyrazol-3-ylboronic acid (156 mg, 1.4 mmol), tetrakis(triphenylphosphine)palladium(0) (242 mg, 0.21 mmol), and sodium carbonate (222 mg, 2.1 mmol) in dimethylformamide (2 ml), was added tert-butyl-2-bromobenzylcarbamate (200 mg, 0.699 mmol). The suspension was stirred at 100° C. for 2 h, cooled to room temperature, poured onto saturated sodium bicarbonate and extracted with ethyl acetate. The combined organic layers were washed with saturated sodium chloride, dried with magnesium sulfate and concentrated in vacuo. The crude material was passed through silica (ISCO, 0–30% ethyl acetate/hexane) to give tert-butyl 2-(1H-pyrazol-3-yl)benzylcarbamate; MS (ES+) M+1 274.1 for $C_{15}H_{19}N_3O_2$.

Step E 2-(1H-Pyrazol-3-yl)-benzylamine hydrochloride salt (12-5)

hydrogen chloride gas was bubbled through a 0° C. solution of tert-butyl 2-(1H-pyrazol-3-yl)benzylcarbamate (60 mg, 0.220 mmol) in ethyl acetate (5 ml) for 2 min and stirred for 40 min. A precipitate formed, and the suspension was concentrated in vacuo to give 2-(1H-pyrazol-3-yl)-benzylamine hydrochloride salt; MS (ES+) M+1 174.1 for $C_{10}H_{11}N_3$.

EXAMPLE 13

2-Imidazol-1-yl-benzylamine

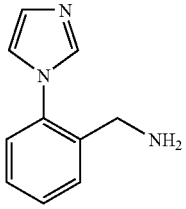

Step A

2-Imidazol-1-yl-benzonitrile (13-1)

To a solution of 1H-imidazole (0.61 g, 9.0 mmol) in dimethylformamide (8 ml) was added sodium hydride (60% in oil, 0.36 g, 9.0 mmol) and the reaction mixture was stirred at room temperature for 40 min. 2-Fluoro-benzonitrile (0.9 ml, 8.2 mmol) was added and the reaction was stirred at room temperature for 45 min, heated to 60° C. for 45 min and then stirred at room temperature overnight. Ethyl acetate was added and the mixture was washed with water and brine. Drying and solvent evaporation gave 2-imidazol-1-yl-benzonitrile; $^1$H NMR (CDCl$_3$, 400 MHz) δ 7.86 (bs, 1H), 7.84 (m, 1H), 7.75 (m, 1H), 7.54 (m, 1H), 7.47 (dd, 1H, J=8.1 Hz, J=1 Hz), 7.36 (m, 1H), 7.27 (m, 1H).

Step B

2-Imidazol-1-yl-benzylamine (13-2)

A solution of 2-imidazol-1-yl-benzonitrile (200 mg, 1.2 mmol) in ethanol saturated with ammonia (20 ml) was stirred in the presence of Raney nickel (50% slurry in water, washed with ethanol, catalytic amount) under a hydrogen atmosphere for 4 h. The reaction mixture was filtered over celite and concentrated to give 2-Imidazol-1-yl-benzylamine; $^1$H NMR (CDCl$_3$, 400 MHz) δ 7.69 (bs, 1H), 7.57 (m, 1H), 7.47 (m, 1H), 7.38 (m, 1H), 7.27 (m, 1H), 7.22 (bs, 1H), 7.16 (m, 1H), 3.73 (s, 2H).

EXAMPLE 14

2-(1H-Tetrazol-5-yl)-benzylamine hydrochloride salt

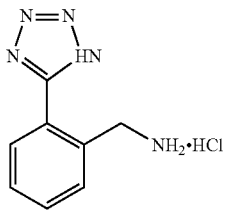

Step A

2-Azidomethyl-benzonitrile (14-1)

A solution of 2-bromomethyl-benzonitrile (1.0 g, 5.1 mmol) and sodium azide (0.40 g, 6.1 mmol) in dimethylformamide (10 ml) was stirred at room temperature for 2 h. Ethyl acetate was added and the reaction mixture was washed with water and brine. Drying and solvent evaporation gave 2-azidomethyl-benzonitrile; $^1$H NMR (CDCl$_3$, 400 MHz) δ 7.71 (d, 1H, J=7.7 Hz), 7.64 (m, 1H), 7.53 (d, 1H, J=7.8 Hz), 7.47 (t, 1H, J=7.6 Hz), 4.62 (s, 2H).

Step B (2-Cyano-benzyl)-carbamic acid tert-butyl ester (14-2)

A solution of 2-azidomethyl-benzonitrile (0.59 g, 3.7 mmol), tin (II) chloride (1.0 g, 5.5 mmol) and di-tert-butyl dicarbonate (1.2 g, 5.5 mmol) in methanol (16 ml) and tetrahydrofuran (8 ml) was stirred at room temperature for 1 h. Concentration and flash chromatography (silica gel, hexane-ethyl acetate, 85:15) gave (2-cyano-benzyl)-carbamic acid tert-butyl ester; $^1$H NMR (CDCl$_3$, 400 MHz) δ 7.64 (d, 1H, J=7.8 Hz), 7.58 (m, 1H), 7.52 (m, 1H), 7.37 (m, 1H), 5.12 (bs, 1H), 4.50 (d, 2H, J=6 Hz), 1.45 (s, 9H).

Step C

[2-(1H-Tetrazol-5-yl)-benzyl]-carbamic acid tert-butyl ester (14-3)

A solution of (2-cyano-benzyl)-carbamic acid tert-butyl ester (35 mg, 0.15 mmol), sodium azide (49 mg, 0.75 mmol), ammonium chloride (40 mg, 0.75 mmol) in dimethylformamide (0.5 ml) was heated to 110° C. for 8 h. After cooling to room temperature, ethyl acetate was added and the resultant solid filtered. Concentration of the filtrate gave [2-(1H-tetrazol-5-yl)-benzyl]-carbamic acid tert-butyl ester; $^1$H NMR (CD$_3$OD, 400 MHz) δ 7.71(d, 1H, J=7.5 Hz), 7.58 (m, 2H), 7.48 (m, 1H), 4.44 (s, 2H), 1.42 (s, 9H).

Step D 2-(1H-Tetrazol-5-yl)-benzylamine hydrochloride salt (14-4)

Through a solution of [2-(1H-tetrazol-5-yl)-benzyl]-carbamic acid tert-butyl ester (33 mg) in ethyl acetate (15 ml), cooled to 0° C. was bubbled HCl (g) for 5 min. The reaction was stirred at room temperature for 0.5 h. Nitrogen was bubbled through the reaction mixture and ether was added. Filtration gave 2-(1H-tetrazol-5-yl)-benzylamine hydrochloride salt; $^1$H NMR (CD$_3$OD, 400 MHz) δ 7.86 (d, 1H, J=7.7 Hz), 7.79 (m, 1H), 7.69 (m, 1H), 7.63 (m, 1H), 4.36 (s, 2H).

EXAMPLE 15

2-(1-Methyl-1H-tetrazol-5-yl)-benzylamine hydrochloride salt

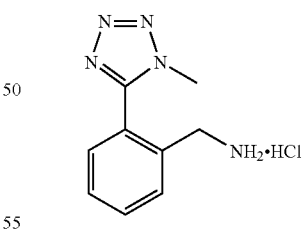

Step A

[2-(1-Methyl-1H-tetrazol-5-yl)-benzyl]-carbamic acid tert-butyl ester (15-1)

A solution of [2-(1H-tetrazol-5-yl)-benzyl]-carbamic acid tert-butyl ester (0.23 g, 0.84 mmol, preparation described in example 14, Step C), crushed potassium carbonate (0.58 g, 4.2 mmol) and iodomethane (0.26 ml, 4.2 mmol) in dimethylformamide (4.7 ml) was stirred at room temperature for 1 h. Water was added and the reaction mixture was extracted with chloroform. Drying and solvent evaporation gave a mixture of regioisomers; separation and purification by reverse phase preparative HPLC (5% to 95% CH₃CN in water containing 0.1% TFA, C18 PRO YMC 20×150 mm) gave [2-(1-methyl-1H-tetrazol-5-yl)-benzyl]-carbamic acid tert-butyl ester; ¹H NMR (CDCl₃, 400 MHz) δ 7.66 (d, 1H, J=7.4 Hz), 7.58 (m, 1H), 7.46 (m, 1H), 7.33 (d, 1H, J=7.6 Hz), 4.17 (d, 2H, J=6.3 Hz), 4.05 (s, 3H), 1.41 (s, 9H) and [2-(2-methyl-2H-tetrazol-5-yl)-benzyl]-carbamic acid tert-butyl ester; ¹H NMR (CDCl₃, 400 MHz) δ 8.06 (d, 1H, J=7.4 Hz), 7.61 (d, 1H, J=7 Hz), 7.44 (m, 2H), 5.82 (bs, 1H), 4.52 (d, 2H, J=6.5 Hz), 4.44 (s, 3H), 1.43 (s, 9H).

Step B 2-(1-Methyl-1H-tetrazol-5-yl)-benzylamine hydrochloride salt (15-2)

Through a solution of [2-(1-methyl-1H-tetrazol-5-yl)-benzyl]-carbamic acid tert-butyl ester (10 mg) in ethyl acetate (5 ml), cooled to 0° C. was bubbled HCl (g) for 5 min. The reaction was stirred at room temperature for 0.5 h. Nitrogen was bubbled through the reaction mixture. Concentration from ethyl acetate gave 2-(1-methyl-1H-tetrazol-5-yl)-benzylamine hydrochloride salt; ¹H NMR (CD₃OD, 400 MHz) δ 7.75 (m, 4H), 4.18 (s, 3H), 4.11 (m, 2H).

EXAMPLE 16

2-(2-Methyl-2H-tetrazol-5-yl)-benzylamine hydrochloride salt

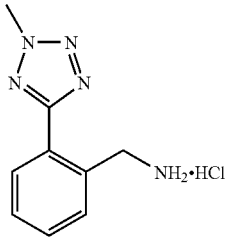

Step A 2-(2-Methyl-2H-tetrazol-5-yl)-benzylamine hydrochloride salt (16-1)

Through a solution of [2-(2-methyl-2H-tetrazol-5-yl)-benzyl]-carbamic acid tert-butyl ester (15 mg, preparation described in example 15, Step A) in ethyl acetate (5 ml), cooled to 0° C. was bubbled HCl (g) for 5 min. The reaction was stirred at room temperature for 0.5 h. Nitrogen was bubbled through the reaction mixture. Concentration from ethyl acetate gave 2-(2-methyl-2H-tetrazol-5-yl)-benzylamine hydrochloride salt; ¹H NMR (CD₃OD, 400 MHz) δ 8.24 (m, 1H), 7.63 (m, 3H) 4.48 (s, 3H), 4.47 (m, 2H).

EXAMPLE 17

[6-Chloro-3-(2,2-difluoro-2-pyridin-2-yl-ethylamino)-2-oxo-2H-pyrazin-1-yl]-acetic acid

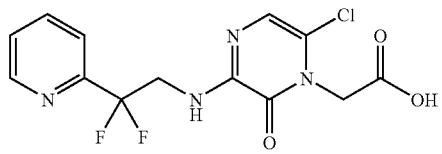

Step A

Oxo-pyridin-2-yl-acetic acid ethyl ester (17-1)

To a stirred solution of 20 mL (210 mmol) of 2-bromopyridine in 500 mL of dry ether at −78° C. under Ar was added 85 mL of a 2.5 M solution of n-butyllithium in hexane in a slow stream. After stirring in the cold for 30 min, the solution was transferred over a 5 min period via two cannula into a 0° C. stirred solution of 100 mL (736 mmol) of diethyl oxalate in 1.0 L of dry ether under Ar. After stirring for 2 h in the cold, the reaction mixture was washed with 600 mL of sat. NaHCO₃, water, and brine. The solution was dried over MgSO₄ and the solvents concentrated at reduced pressure to give a red oil that was purified by SiO₂ chromatography (10×15 cm) using 1:4 to 35:65 EtOAc-hexanes. The product-containing fractions were concentrated at reduced pressure to afford the product as a reddish oil: ¹H NMR (CDCl₃) δ 1.42 (t, 3H), 4.45–4.55 (m, 2H), 7.55–7.6 (m, 1H), 7.9–7.95 (m, 1H), 8.11 (d, 1H), 8.78 (d, 1H).

Step B

Difluoro-pyridin-2-yl-acetic acid ethyl ester (17-2)

A stirred solution of 22 g (123 mmol) of oxo-pyridin-2-yl-acetic acid ethyl ester and 75 g (465 mmol) of diethylaminosulfurtrifluoride (DAST) were heated to 55° C. under Ar overnight. Because the reaction was not complete, 5 g additional DAST was added, and the reaction heated for an additional 24 h. The reaction mixture was cooled to rt, and poured very slowly into a stirred mixture of 1 kg of ice, 400 mL of ethyl acetate and 500 mL of sat. NaHCO₃. After the addition, the mixture was basified by the addition of solid NaHCO₃. The aqueous layer was extracted with EtOAc, and the combined organic layers washed with sat. NaHCO₃, brine, dried over Na₂SO₄ and the solvents concentrated at reduced pressure to give the product as a brown oil: ¹H NMR (CDCl₃) δ 1.35 (t, 3H), 4.35–4.4 (m, 2H), 7.4–7.45 (m, 1H), 7.75 (d, 1H), 7.95 (d, 1H), 8.45 (d, 1H).

Step C 2,2-Difluoro-2-pyridin-2-yl-ethanol (17-3)

To a stirred solution of 19.5 g (97 mmol) of difluoro-pyridin-2-yl-acetic acid ethyl ester in 200 mL of absolute ethanol at 0° C. was added 4.42 g (116 mmol) of sodium borohydride in small portions. After 30 min, the reaction was quenched by the addition of 50 mL of sat. NH₄Cl. The reaction mixture was concentrated at reduced pressure and the residue partitioned between 500 mL of ethyl acetate and sat. NaHCO₃. The organic layer was washed with water, brine, and dried over Na₂SO₄ and concentrated at reduced pressure to give a brown oil that was purified on SiO₂ (10×17 cm) using 1:1 EtOAc-hexane. After re-chromatographing the mixed fractions, all clean fractions were combined and concentrated at reduced pressure, giving the product as a beige crystalline solid: ¹H NMR (CDCl₃) δ 3.6 (t, 1H), 4.17–4.3 (m, 2H), 7.4–7.45 (m, 1H), 7.73 (d, 1H), 7.84–7.91 (m, 1H), 8.61 (d, 1H).

Step D trifluoro-methanesulfonic acid 2,2-difluoro-2-pyridin-2-yl-ethyl ester (17-4)

To a stirred solution of 5 g (31.4 mmol) of 2,2-difluoro-2-pyridin-2-yl-ethanol and 9.69 g (47.2 mmol) of 2,6-di-t-butyl-4-methylpyridine in 110 mL of methylene chloride at −78° C. under Ar was added 7.93 mL (47.2 mmol) of triflic anhydride dropwise. After 1 h, the reaction was diluted with 100 mL of pentane and filtered. The filtrate was concentrated and treated again with pentane and filtered. Concentration of the filtrate gave the product as a brown oil, contaminated with 2,6 -di-t-butyl-4-methylpyridine: $^1$H NMR (CDCl$_3$) δ 5.12 (t, 2H), 7.45–7.5 (m, 1H), 7.75 (d, 1H), 7.86–7.94 (m, 1H), 8.65 (d, 1H).

Step E 2-(2-Azido-1,1-difluoro-ethyl)-pyridine (17-5)

To a stirred solution of 5.5 g of trifluoro-methanesulfonic acid 2,2-difluoro-2-pyridin-2-yl-ethyl ester 1–4 in 70 mL of DMF was added 6.74 g (104 mmol) of sodium azide under Ar. The mixture was heated to 60° C. overnight. A second batch was run in the same manner, and after cooling to rt, both reactions were poured into 600 mL of water, and extracted with 3×500 mL of ether. The combined extracts were washed with brine, dried over Na$_2$SO$_4$ and concentrated at reduced pressure to give an oil that was purified by SiO$_2$ (10×6 cm) using hexane 1:3 EtOAc-hexane and 1:1 EtOAc-hexane. The product-containing fractions were concentrated at reduced pressure to give the product as a yellow oil: $^1$H NMR (CDCl$_3$) δ 4.05 (t, 2H), 7.4–7.45 (m, 1H), 7.73 (d, 1H), 7.83–7.89 (m, 1H), 8.67 (d, 1H).

Step F 2,2-Difluoro-2-pyridin-2-yl-ethylamine (17-6)

A stirred solution of 100 mg of 2-(2-azido-1,1-difluoro-ethyl)-pyridine was hydrogenated in 10 mL of ethyl acetate over 100 mg of 10% palladium on carbon using a balloon for 1 h. The catalyst was removed by filtration and the solvents removed at reduced pressure. A total of 1.8 g (9.7 mmol) of the azide was reduced using this procedure to give 2,2-difluoro-2-pyridin-2-yl-ethylamine as a yellow oil: $^1$H NMR (CDCl$_3$) δ 8.66 (d, 1H, 4.2 Hz), 7.82 (td,1H, 7.7, 1.7 Hz), 7.68 (d, 1H, 8.1 Hz), 7.37–7.40 (m, 1H), 3.44 (t, 2H, 14.3 Hz), 1.41 (br s, 2H).

Step G

N-Ethoxycarbonylmethyl-oxalamic acid ethyl ester (17-7)

To a suspension of ethyl glycine.HCl (38.4 g, 275 mmol) in 1,2-dichloroethane (360 mL) was added triethylamine (77.0 mL, 550 mmol) at room temperature. After stirring for 30 minutes the heterogenous mixture was cooled to 0° C. and ethyl oxalyl chloride (30.3 mL, 275 mol) was added dropwise over the course of 1 h. Upon completion of the addition, the cooling bath was removed and the reaction was stirred at room temperature overnight. The reaction was diluted with water (250 mL) and the layers separated. The aqueous layer was backwashed with 2 portions of dichloromethane (250 mL). The combined organic layers were washed with water (250 mL), followed by brine (250 mL), dried over MgSO$_4$ and concentrated to give N-ethoxycarbonylmethyl-oxalamic acid ethyl ester as an oil that was taken directly onto the next step.

Step H

[(2,2-Dimethoxy-ethylaminooxalyl)-amino]-acetic acid ethyl ester (17-8)

To a solution of N-ethoxycarbonylmethyl-oxalamic acid ethyl ester (84.0 g, 414 mmol) 2–1 in 2-propanol (500 mL) was added aminoacetaldehyde dimethyl acetal (45.7 g, 435 mmol) in one portion. After stirring overnight at room temperature, the reaction mixture was concentrated to a thick orange oil. This thick slurry was diluted with 2-propanol (300 mL) and the solid was broken up with a spatula. Filtration afforded a solid which was further rinsed with an additional portion of 2-propanol. Removal of residual 2-propanol was accomplished via high vacuum to afford a light orange solid: $^1$H NMR (CDCl$_3$) δ 7.82 (br s, 1H), 7.50 (br s, 1H), 4.41 (t, 1H, 5.3 Hz), 4.24 (q, 2H, 7.1 Hz), 4.09 (d, 2H, 5.9 Hz), 3.47 (dd, 2H, 5.3, 6.2 Hz), 3.40 (s, 6H), 1.30 (t, 3H, 7.1 Hz).

Step I (2,3-Dioxo-3,4-dihydro-2H-pyrazin-1-yl)-acetic acid ethyl ester (17-9)

A solution of [(2,2-Dimethoxy-ethylanminooxalyl)-amino]-acetic acid ethyl ester (89.8 g, 343 mmol), acetic acid (400 mL), and conc. HCl (2 mL) was heated to reflux. After 1 h the black reaction was concentrated to a thick oil (high vacuum employed to ensure complete removal of AcOH) which was diluted with EtOH (150 mL) and MeOH (150 mL). Scraping the thick black oil with a spatula induced precipitation of the product. The MeOH was removed via rotary evaporation and the remaining slurry was filtered and rinsed with EtOH (200 mL) to deliver a tan solid. Recrystallization from refluxing EtOH (300 mL) afforded the product as an off-white powder: $^1$H NMR (CD$_3$OD) δ 6.50 (d, 1H, 5.9 Hz), 6.36 (d, 1H, 5.9 Hz), 4.58 (s, 2H), 4.23 (q, 2H, 7.1 Hz), 1.28 (t, 3H, 7.1 Hz). Further crude dione could be obtained upon concentration of the mother liquor.

Step J (3-Bromo-2-oxo-2H-pyrazin-1-yl)-acetic acid ethyl ester (17-10)

A solution of (2,3-dioxo-3,4-dihydro-2H-pyrazin-1-yl)-acetic acid ethyl ester (25.0 g, 126 mmol) and phosphorous oxybromide (37.9 g, 132 mmol) in 1,2-dichloroethane (250 mL) was heated to reflux. After 8 h the reaction mixture was treated with sat. aq. Na$_2$CO$_3$ (250 mL) and stirred for 1 h. The mixture was diluted with water (100 mL) and dichloromethane (100 mL), the layers were separated and the aqueous layer was backwashed with EtOAc (3×200 mL). The combined organics were dried (MgSO$_4$), and concentrated to give an oil which was stored on a high vacuum line overnight to afford a brown solid. $^1$H NMR (CDCl$_3$) δ 7.17 (d, 1H, 4.2 Hz), 7.07 (d, 1H, 4.2 Hz), 4.65 (s, 2H), 4.27 (q, 2H, 7.2 Hz), 1.31 (t, 3H, 7.2 Hz).

Step K

[3-(2.2-Difluoro-2-pyridin-2-yl-ethylamino)-2-oxo-2H-pyrazin-1-yl]-acetic acid ethyl ester (17-11)

A solution of 4.80 g (30.4 mmol) of 2,2-difluoro-2-pyridin-2-yl-ethylamine, 4.24 mL (30.4 mmol) of triethylamine and 7.93 g (30.4 mmol) of (3-bromo-2-oxo-2H-pyrazin-1-yl)-acetic acid ethyl ester was heated to 120° C. in a sealed tube overnight in 12 mL of toluene and 4 mL of ethanol. The reaction was concentrated and the residue was partitioned between dichloromethane and sat. aq. NaHCO$_3$. The aqueous layer was backwashed with 4 portions of dichloromethane. The combined organic layers were dried over MgSO$_4$ and the solvents removed at reduced pressure to give an oil that was chromatographed on SiO$_2$ using 60:40 to 40:60 hexane-EtOAc to give Ethyl 3 -(2,2-difluoro-2-(2-pyridylethylamino)pyrazin(1H)-2-one-1-acetate as a yellow solid: $^1$H NMR (CDCl$_3$) δ 8.67 (dd, 1H, 4.8, 0.7 Hz), 7.81 (ddd,1H, 7.8, 7.8, 1.7 Hz), 7.69 (dd, 1H, 7.8, 1 Hz), 7.38 (dd, 1H, 5.1, 7.0 Hz), 6.86 (d, 1H, 4.8 Hz), 6.54 (br t, 1H, 5.9 Hz), 6.40 (d, 1H, 4.6 Hz), 4.54 (s, 2H), 4.38 (td, 2H, 14.0, 6.4 Hz), 4.24 (q, 2H, 7.1 Hz), 1.29 (t, 3H, 7.1 Hz).

Step L

[6-Chloro-3-(2,2-difluoro-2-pyridin-2-yl-ethylamino)-2-oxo-2H-pyrazin-1-yl]-acetic acid ethyl ester (17-12)

A stirred solution of 6.81 g (20.1 mmol) of [3-(2,2-difluoro-2-pyridin-2-yl-ethylamino)-2-oxo-2H-pyrazin-1-yl]-acetic acid ethyl ester and 2.42 g (18.1 mmol) of N-chlorosuccinimide in 100 mL of 1,2-dichloroethane was heated to reflux. An additional 242 mg (1.81 mmol) and 75 mg (0.56 mmol) of NCS were added to the reaction mixture after 1 h and 1.5 h, respectively. After 2.5 h total, the solution was cooled to room temperature and partitioned between dichloromethane (150 mL) and sat. aq. NaHCO$_3$ (200 mL). The layers were separated and the aqueous phase was backwashed with dichloromethane (2×200 mL). The combined organic layers were dried over MgSO$_4$ and the solution concentrated to a volume of 10 mL. This liquid was directly loaded onto a SiO$_2$ column and eluted with 65:35 to 55:45 hexane-EtOAc to give the title compound as a yellow solid: $^1$H NMR (CDCl$_3$) δ 8.68 (d, 1H, 4.8, Hz), 7.83 (ddd,1H, 7.7, 7.7, 1.6 Hz), 7.9 (dd, 1H, 7.9 Hz), 7.40 (dd, 1H, 4.9, 7.3 Hz), 6.96 (s, 1H), 6.49 (br t, 1H, 5.9 Hz), 4.89 (s, 2H), 4.38 (td, 2H, 13.9, 6.5 Hz), 4.26 (q, 2H, 7.1 Hz), 1.30 (t, 3H, 7.1 Hz).

Step M

[6-Chloro-3-(2.2-difluoro-2-pyridin-2-yl-ethylamino)-2-oxo-2H-pyrazin 1-yl]-acetic acid (17-13)

To a stirred solution of 7.27 g (19.5 mmol) of [6-chloro-3-(2,2-difluoro-2-pyridin-2-yl-ethylamino)-2-oxo-2H-pyrazin-1-yl]-acetic acid ethyl ester in 200 mL of methanol was added 39 mL (39.0 mmol) of 1M aq. potassium hydroxide. After 3 h the solution was acidified to pH=7 using conc. HCl, and concentrated at reduced pressure (azeotrope with PhCH$_3$) to give a white solid containing potassium chloride and the product. $^1$H NMR (CD$_3$OD) δ 8.64 (d, 1H, 4.8 Hz), 7.93 (ddd,1H, 7.7, 7.7, 1.5 Hz), 7.70 (d, 1H, 8.0 Hz), 7.49 (dd, 1H, 5.2, 7.4 Hz), 6.80 (s, 1H), 4.67 (s, 2H), 4.27 (t, 2H, 13.9 Hz).

EXAMPLE 18

{6-Chloro-3-[2,2-difluoro-2-(1-oxy-pyridin-2-yl)-ethylamino]-2-oxo-2H-pyrazin-1-yl}-acetic acid

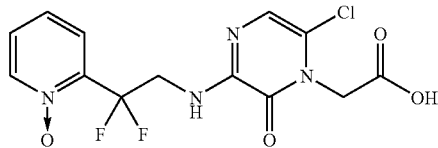

Step A 2-(2-Azido-1,1-difluoro-ethyl)-pyridine-1-oxide (18-1)

To a stirred solution of 2-(2-azido-1,1-difluoro-ethyl)-pyridine (5.75 g, 31.3 mmol, preparation described in example 17, step E) in 1,2-dichloroethane (100 mL) was added 3-chloroperoxybenzoic acid (10.26 g, 41.6 mmol) and 3-tert-butyl-4-hydroxy-5methylphenyl sulfide (1.12 g, 3.13 mmol) under Ar. The mixture was heated at 55° C. overnight. In the morning, the solution was poured into a sat. aq. NaHCO$_3$/Na$_2$S$_2$O$_3$ solution (200 mL). The layers were separated and the aqueous phase was backwashed with dichloromethane (3×150 mL). The combined organic layers were dried over MgSO$_4$, concentrated and chromatographed on a short SiO$_2$ column using 100% EtOAc to give the title compound as a white solid: $^1$H NMR (CDCl$_3$) δ 4.38 (t, 2H, 13.5 Hz), 7.36–7.44 (m, 2H), 7.72 (dd, 1H, 2.3 Hz, 7.6 Hz), 8.26 (d, 1H, 6.1 Hz).

Step B 2,2-Difluoro-2-(1-oxy-pyridin-2-yl)-ethylamine (18-2)

Triphenylphosphine (7.72 g, 29.5 mmol) was added to a water bath cooled solution of 2-(2-azido-1,1-difluoro-ethyl)-pyridine-1-oxide (5.61 g, 28.1 mmol) in THF (90 mL). After 1 h water (10 mL) was added and the mixture was heated to 55° C. Two hours after the addition of water, the heating bath was removed and the solution was allowed to stir overnight. The reaction was subsequently concentrated, diluted with EtOAc (250 mL), and HCl (25 mL, 2.6M in EtOAc) was added dropwise. Stirring was continued for 20 min, after which time the mixture was filtered and rinsed with EtOAc (150 mL). To a stirred suspension of this solid in dichloromethane (300 mL) was added NaOH (3.33 g in 15 mL H$_2$O) dropwise. After 15 min the mixture was poured into a separatory funnel and the organic phase was separated. The aqueous phase was saturated with solid NaCl and extracted with CH$_2$Cl$_2$ (3×100 mL). The combined organic extracts were dried over Na$_2$SO$_4$ and concentrated to an oil which solidified upon storage in the freezer: $^1$H NMR (CDCl$_3$) δ 8.25 (br d, 1H, 6.2 Hz), 7.69 (dd, 1H, 2.8, 7.3 Hz), 7.32–7.39 (m, 2H), 3.76 (t, 2H, 15.2 Hz), 1.29 (br s, 2H).

Step C

{3-[2,2-Difluoro-2-(1-oxy-pyridin-2-yl)-ethylamino]-2-oxo-2H-pyrazin-1-yl}-acetic acid ethyl ester (18-3)

A mixture of 3.0 g (17.2 mmol) of 2,2-difluoro-2-(1-oxy-pyridin-2-yl)-ethylamine, 2.72 mL (19.5 mmol) of triethylamine and 4.5 g (17.2 mmol) of (3-bromo-2-oxo-2H-pyrazin-1-yl)-acetic acid ethyl ester in 9 mL of toluene and 3 mL of ethanol was heated to 120° C. in a sealed tube for 24 h. The reaction was concentrated and the residue was partitioned between EtOAc (200 mL) and sat. aq. NaHCO$_3$ (200 mL). The aqueous layer was backwashed with EtOAc (5×150 mL). The combined organic layers were dried over MgSO$_4$ and the solvents removed at reduced pressure to give a brown solid. This crude material was diluted with EtOAc (50 mL), filtered, and rinsed with EtOAc (2×50 mL) to afford the title compound as a tan powder: $^1$H NMR (CDCl$_3$) δ 8.26 (d, 1H, 6.4 Hz), 7.61 (br d, 1H, 7.9 Hz), 7.34 (dd, 1H, 6.6, 6.6 Hz), 7.26 (dd, 1H), 6.78 (d, 1H, 4.6 Hz), 6.39 (br t, 1H, 6.6 Hz), 6.37 (d, 1H, 4.6 Hz), 4.66 (td, 2H, 13.8, 7.0 Hz), 4.52 (s, 2H), 4.23 (q, 2H, 7.1 Hz), 1.28 (t, 3H, 7.1 Hz).

Step D

{6-Chloro-3-[2,2-difluoro-2-(1-oxy-pyridin-2-yl)-ethylamino]-2-oxo-2H-pyrazin-1-yl}-acetic acid ethyl ester (18-4)

A stirred solution of 4.96 g (14.0 mmol) of {3-[2,2-difluoro-2-(1-oxy-pyridin-2-yl)-ethylamino]-2-oxo-2H-pyrazin-1-yl}-acetic acid ethyl ester and 1.86 g (14.0 mmol) of N-chlorosuccinimide in 200 mL of 1,2-dichloroethane was heated to 70° C. After 3 h the solution was cooled to room temperature and partitioned between dichloromethane (150 mL) and sat. aq. NaHCO$_3$ (200 mL). The layers were separated and the aqueous phase was backwashed with dichloromethane (4×200 mL) and EtOAc (2×200 mL). The combined organic layers were dried over NaSO$_4$ and the solution concentrated. This crude solid was purified on a SiO$_2$ column with 100% EtOAc to 10:90 MeOH:EtOAc to give the title compound as a white solid: $^1$H NMR (CDCl$_3$) δ 8.26 (d, 1H, 6.4 Hz), 7.62 (dd, 1H, 2.2, 7.9 Hz), 7.35 (ddd, 1H, 2.1, 7.7, 7.7 Hz), 7.2 (dd, 1H, 7.7 Hz), 6.86 (s, 1H), 6.35 (br t, 1H, 6.7 Hz), 4.85 (s, 2H), 4.64 (td, 2H, 13.8, 6.9 Hz), 4.24 (q, 2H, 7.1 Hz), 1.29 (t, 3H, 7.1 Hz).

Step E

{6-Chloro-3-[2,2-difluoro-2-(1-oxy-pyridin-2-yl)-ethylamino]-2-oxo-2H-pyrazin-1-yl}-acetic acid (18-5)

To a stirred solution of 4.88 g (12.6 mmol) of {6-Chloro-3-[2,2-difluoro-2-(1-oxypyridin-2-yl)-ethylamino]-2-oxo-2H-pyrazin-1-yl}-acetic acid ethyl ester in methanol (100 mL) was added 5.0 g potassium hydroxide (89.1 mmol dissolved in 20 mL water). After 1 h the solution was concentrated, diluted with 50 mL of water and acidified to pH=7 using conc. HCl. Concentration at reduced pressure (azeotrope with PhCH$_3$) afforded an off-white solid containing potassium chloride and the title compound: $^1$H NMR (CD$_3$OD) δ 8.36 (d, 1H, 6.2 Hz), 7.69 (dd, 1H, 7.7, 2.2 Hz), 7.51–7.59 (m, 2H), 6.67 (s, 1H), 4.62 (s, 2H), 4.55 (t, 2H, 13.1 Hz).

EXAMPLE 19

[3-(2,2-Difluoro-2-pyridin-2-yl-ethylamino)-2-oxo-2H-pyrazin-1-yl]acetic acid

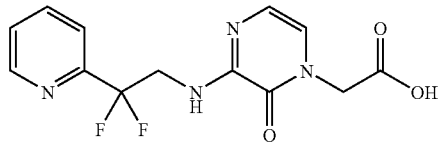

Step A 3-(2,2-Difluoro-2-pyridin-2-yl-ethylamino)-2-oxo-2H-pyrazin-1-yl]acetic acid (19-1)

To a solution of 2.84 g (8.41 mmol) [3-(2,2-difluoro-2-pyridin-2-yl-ethylamino)-2oxo-2H-pyrazin-1-yl]-acetic acid ethyl ester (preparation described in example 17, step K) in 10.0 mL methanol was added 8.83 mL (8.83 mmol) 1.0N lithium hydroxide (aq) and the light yellow solution stirred 1 h at room temperature. The reaction pH was adjusted to 7.0 with a dropwise addition of 1.0N HCl in ether to give a precipitate. The solid was removed by filtration, washed well with water and dried under high vacuum for 24 h to give 3-[2,2-Difluoro-2-pyridin-2-yl-ethylamino)-2-oxo-2H-pyrazin-1-yl]acetic acid as a white solid: $^1$H NMR (DMSO-d$_6$, 400 MHz): δ 13.13 (br s, 1H), 8.70 (d, 1H, J=4.7 Hz), 7.98 (t, 1H, J=7.8 Hz), 7.70 (d, 1H, J=7.9 Hz), 7.60–7.55 (m, 1H), 7.16 (t, 1H, J=6.7 Hz), 6.84 (d, 1H, J=4.7 Hz), 6.73 (d, 1H, J=4.6 Hz), 4.57 (s, 2H), 4.24 (dt, 2H, J=6.6 and 15.2 Hz); MS (Electrospray): M+H=311.0.

EXAMPLE 20

{3-[2,2-Difluoro-2-(1-oxy-pyridin-2-yl)-ethylamino]-2-oxo-2H-pyrazin-1-yl}-acetic acid (20)

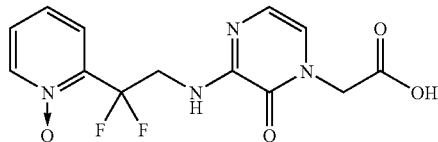

Prepared following a similar protocol as described in example 19, {3-[2,2-difluoro-2-(1-oxy-pyridin-2-yl)-ethylamino]-2-oxo-2H-pyrazin-1-yl}-acetic acid ethyl ester (preparation described in example 18, step C) was converted to {3-[2,2-difluoro-2-(1-oxy-pyridin-2-yl)-ethylamino]-2-oxo-2H-pyrazin-1-yl}-acetic acid.

EXAMPLE 21

{3-[3-(tert-Butoxycarbonyl-cyclopropylmethyl-amino)-propylamino]-2-oxo-2H-pyrazin-1-yl}-acetic acid

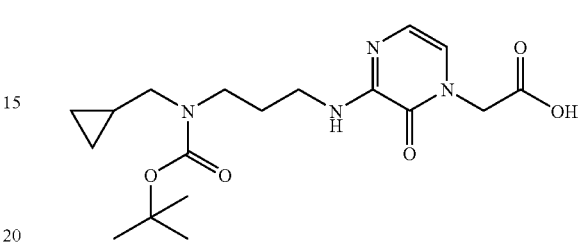

Step A

[3-(Cyclopropylmethyl-amino)-propyl]-carbamic acid benzyl ester (21-1)

A solution of cyclopropanecarbaldehyde (4.6 ml, 0.061 mol), (3-amino-propyl)-carbamic acid benzyl ester hydrochloride (15 g, 0.061 mol) and triethylamine (8.5 ml, 0.061 mol) in methanol (244 ml) was stirred at room temperature overnight. Sodium borohydride (3.7 g, 0.098 mol) was added and the reaction mixture was stirred at room temperature for 4 h. Sodium hydroxide solution (1N) was added and the reaction was concentrated to remove methanol. The residue was extracted with ethyl acetate and the combined extracts were washed with brine. Drying and solvent evaporation gave an oil; flash chromatography (silica gel, chloroform saturated with ammonia-2-propanol, 99.5:0.5) gave [3-(cyclopropylmethyl-amino)-propyl]-carbamic acid benzyl ester; $^1$H NMR (CDCl$_3$, 400 MHz) δ 7.35 (m, 5H), 5.60 (bs, 1H), 5.10 (s, 2H), 3.30 (q, 2H, J=6.1 Hz), 2.70 (t, 2H, J=6.5 Hz), 2.43 (d, 2H, J=6.8 Hz), 1.67 (m, 2H), 0.92 (m, 1H), 0.46 (m, 2H), 0.099 (q, 2H, J=4.9 Hz).

Step B (3-Benzyloxycarbonylamino-propyl)-cyclopropylmethyl-carbamic acid tert-butyl ester (21-2)

A solution of [3-(cyclopropylmethyl-amino)-propyl]-carbamic acid benzyl ester (3.6 g, 0.014 mol) and di-tert-butyl dicarbonate (3 g, 0.014 mol) in methylene chloride (75 ml) was stirred at room temperature for 1 h. Concentration and flash chromatography (silica gel, hexane-ethyl acetate, 85:15–83:17) gave (3-benzyloxycarbonylamino-propyl)-cyclopropylmethyl-carbamic acid tert-butyl ester; $^1$H NMR (CDCl$_3$, 400 MHz) δ 7.36 (m, 5H), 5.09 (s, 2H), 3.36 (m, 2H), 3.18 (m, 2H), 3.04 (m, 2H), 1.64 (m, 2H), 1.45 (s, 9H), 0.95 (m, 1H), 0.48 (m, 2H), 0.19 (q, 2H, J=4.9 Hz).

Step C (3-Amino-propyl)-cyclopropylmethyl-carbamic acid tert-butyl ester (21-3)

A solution of (3-benzyloxycarbonylamino-propyl)-cyclopropylmethyl-carbamic acid tert-butyl ester (4.2 g, 0.012 mol) in ethanol (60 ml) was stirred in the presence of palladium on carbon (10%, 0.42 g) under a hydrogen atmosphere for 2 h. Filtration through celite and concentration gave (3-amino-propyl)-cyclopropylmethyl-carbamic acid tert-butyl ester; $^1$H NMR (CDCl$_3$, 400 MHz) δ 3.35 (m, 2H), 3.08 (m, 2H), 2.70 (t, 2H, J=6.8 Hz), 1.67 (m, 2H), 1.46 (s, 9H), 1.30 (bs, 2H), 0.97 (m, 1H), 0.48 (m, 2H), 0.20 (q, 2H, J=5 Hz).

Step D

{3-[3-(tert-Butoxycarbonyl-cyclopropylmethyl-amino)-propylamino]-2-oxo-2H-pyrazin-1-yl}-acetic acid ethyl ester (21-4)

A solution of (3-amino-propyl)-cyclopropylmethyl-carbamic acid tert-butyl ester (5 g, 0.022 mol), (3-bromo-2-oxo-2H-pyrazin-1-yl)-acetic acid ethyl ester (5.2 g, 0.020 mol, preparation described in example 17, step J) and triethylamine (3.3 ml, 0.024 mol) in ethanol (16 ml) was heated to 80° C. in a sealed tube overnight. Concentration and flash chromatography (silica gel, chloroform-diethyl ether, 90: 10) gave {3-[3-(tert-butoxycarbonyl-cyclopropylmethyl-amino)-propylamino]-2-oxo-2H-pyrazin-1-yl}-acetic acid ethyl ester; $^1$H NMR (CDCl$_3$, 400 MHz) δ 6.85 (d, 1H, J=4.7 Hz), 6.36 (d, 1H, J=4.7 Hz), 4.56 (s, 2H), 4.25 (q, 2H, J=7.1 Hz), 3.42 (m, 2H), 3.36 (m, 2H), 3.10 (m, 2H), 1.87 (m, 2H), 1.46 (s, 9H), 1.30 (t, 3H, J=7.1 Hz), 0.96 (m, 1H), 0.48 (m, 2H), 0.20 (m, 2H).

Step E

{3-[3-(tert-Butoxycarbonyl-cyclopropylmethyl-amino)-propylamino]-2-oxo-2H-pyrazin-1-yl}-acetic acid (21-5)

A solution of {3-[3-(tert-butoxycarbonyl-cyclopropylmethyl-amino)-propylamino]-2-oxo-2H-pyrazin-1-yl}-acetic acid ethyl ester (250 mg, 0.61 mmol) and lithium hydroxide monohydrate (33 mg, 0.79 mmol) in water (0.72 ml) and methanol (3.6 ml) was stirred at room temperature for 2 h. hydrochloric acid solution (1N, 0.79 ml) was added and the reaction mixture was stirred at room temperature for 10 min. Concentration from methanol gave {3-[3-(tert-butoxycarbonyl-cyclopropylmethyl-amino)-propylamino]-2-oxo-2H-pyrazin-1-yl}-acetic acid; $^1$H NMR (CD$_3$OD, 400 MHz) δ 6.78 (d, 1H, J=4.8 Hz), 6.69 (d, 1H, J=4.9 Hz), 4.61 (s, 2H), 3.32 (m, 4H), 3.12 (d, 2H, J=6.8 Hz), 1.89 (m, 2H), 1.45 (s, 9H), 1.00 (m, 1H), 0.48 (m, 2H), 0.22 (m, 2H).

EXAMPLE 22

{3-[3-(tert-Butoxycarbonyl-cyclopropylmethyl-amino)-propylamino]-6-chloro-2-oxo-2H-pyrazin-1-yl}-acetic acid

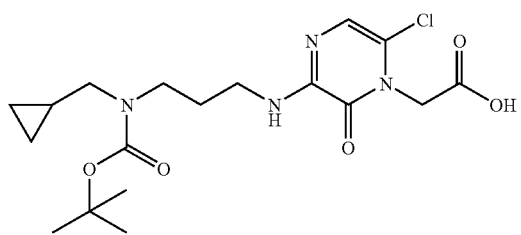

Step A

{3-[3-(tert-Butoxycarbonyl-cyclopropylmethyl-amino)-propylamino]-6-chloro-2-oxo-2H-pyrazin-1-yl}-acetic acid ethyl ester (22-1)

A solution of {3-[3-(tert-butoxycarbonyl-cyclopropylmethyl-amino)-propylamino]-2-oxo-2H-pyrazin-1-yl}-acetic acid ethyl ester (250 mg, 0.61 mmol, preparation described in example 21, step D) and N-chlorosuccinimide (73 mg, 0.55 mmol) in 1,2-dichloroethane (4.2 ml) was heated to 80° C. for 1.5 h. Additional N-chlorosuccinimide (8 mg) was added and the reaction mixture was heated for 1 h. Concentration and flash chromatography (silica gel, hexane-ethyl acetate, 80:20) gave {3-[3-(tert-butoxycarbonyl-cyclopropylmethyl-amino)-propylamino]-6-chloro-2-oxo-2H-pyrazin-1-yl}-acetic acid ethyl ester (0.22 g, 81%); $^1$H NMR (CDCl$_3$, 400 MHz) δ 6.94 (s, 1H), 4.90 (s, 2H), 4.26 (q, 2H, J=7.1 Hz), 3.40 (m, 4H), 3.10 (m, 2H), 1.87 (m, 2H), 1.48 (s, 9H), 1.31 (t, 3H, J=7.1 Hz), 0.97 (m, 1H), 0.49 (m, 2H), 0.21 (m, 2H).

Step B

{3-[3-(tert-Butoxycarbonyl-cyclopropylmethyl-amino)-propylamino]-6-chloro-2-oxo-2H-pyrazin-1-yl}-acetic acid (22-2)

A solution of {3-[3-(tert-butoxycarbonyl-cyclopropylmethyl-amino)-propylamino]-6-chloro-2-oxo-2H-pyrazin-1-yl}-acetic acid ethyl ester (0.22 g, 0.50 mmol) and lithium hydroxide monohydrate (27 mg, 0.65 mmol) in water (0.65 ml) and methanol (3 ml) was stirred at room temperature for 1.5 h. hydrochloric acid solution (1N, 0.65 ml) was added and the reaction mixture was stirred at room temperature for 5 min. Concentration from methanol gave {3-[3-(tert-butoxycarbonyl-cyclopropylmethyl-amino)-propylamino]-6-chloro-2-oxo-2H-pyrazin-1-yl}-acetic acid; $^1$H NMR (CD$_3$OD, 400 MHz) δ 6.90 (s, 1H), 4.90 (s, 2H), 3.34 (m, 4H), 3.11 (d, 2H, J=6.8 Hz), 1.88 (m, 2H), 1.45 (s, 9H), 0.99 (m, 1H), 0.49 (m, 2H), 0.22 (m, 2H).

EXAMPLE 23

[6-Chloro-(S)-3-(1-dimethylaminomethyl-2-phenyl-ethylamino)-2-oxo-2H-pyrazin-1-yl]-acetic acid

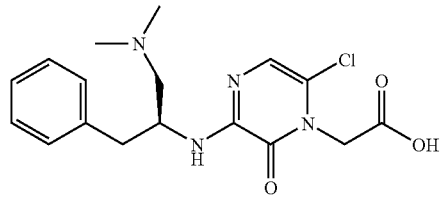

Step A (S)-[3-(1-Azidomethyl-2-phenyl-ethylamino)-2-oxo-2H-pyrazin-1-yl]-acetic acid ethyl ester (23-1)

To a solution of (3-bromo-2-oxo-2H-pyrazin-1-yl)-acetic acid ethyl ester (8.75 g, 33.5 mmol, preparation described in example 17, step J) in EtOH (60 ml) was added (S)-1-azidomethyl-2-phenyl-ethylamine hydrochloride (7.5 g, 35.3 mmol, prepared from (S)-(−)-2-(tertbutoxycarbonylamino)-3-phenyl-1-propanol following the procedure of Horwell et al (J. Med. Chem. 1991, 34, 404–414) and Boc removal under standard HCl(g) conditions) and triethylamine (10.8 ml, 77.6 mmol). The pressure flask was flushed with argon, sealed and the reaction mixture was stirred at 110° C. for 3 days. The reaction mixture was concentrated in vacuo and purified by flash chromatography (silica gel, 20% EtOAc in hexane to 40%) to give (S)-[3-(1-azidomethyl-2-phenylethylamino)-2-oxo-2H-pyrazin-1-yl]-acetic acid ethyl ester as a brown syrup. $^1$H NMR (CDCl$_3$, 400 MHz): δ 7.36–7.20 (m, 5H); 6.85 (d, J=4.4 Hz, 1H); 6.41 (d, J=4.4 Hz, 1H); 6.20 (bd, J=8 Hz, 1H); 4.58 (A of AB, d, J=17.5 Hz, 1H));); 4.52 (B of AB, d, J=17.5 Hz, 1H)); 4.43–4.33 (m, 1H); 4.25 (q, J=7.3 Hz, 2H); 3.52 (A of ABX, dd, J=12.5, 5 Hz, 1H); 3.40 (B of ABX, dd, J=12.5, 5 Hz, 1H); 3.00 (A of ABX, dd, J=14, 6.7 Hz, 1H); 2.92 (B of ABX, dd, J=14, 7.9 Hz, 1H); 1.29 (t, J=7.3 Hz, 3H).

Step B (S)-[3-(1-Azidomethyl-2-phenyl-ethylamino)-6-chloro-2-oxo-2H-pyrazin-1-yl]-acetic acid ethyl ester (23-2)

To a solution of (S)-[3-(1-azidomethyl-2-phenyl-ethylamino)-2-oxo-2H-pyrazin-1-yl]-acetic acid ethyl ester (5.8 g, 16.3 mmol) in dichloroethane (90 ml) was added N-chlorosuccinimide (2.17 g, 16.3 mmol) and the reaction mixture was stirred at 85° C. for 1 h 30 and at room temperature for 18 h. The reaction mixture was concentrated in vacuo and purified by flash chromatography (silica gel, 20% diethyl ether in hexane to 45%) to give (S)-[3-(1-azidomethyl-2-phenyl-ethylamino)-6-chloro-2-oxo-2H-pyrazin-1-yl]-acetic acid ethyl ester as a thick syrup. $^1$H NMR (CDCl$_3$, 400 MHz): δ 7.38–7.20 (m, 5H); 6.85 (s, 1H); 6.10 (bd, J=8.8 Hz,1H); 4.92 (A of AB, d, J=17.7 Hz, 1H));); 4.86 (B of AB, d, J=17.7 Hz, 1H)); 4.40–4.30 (m, 1H); 4.25 (q, J=7 Hz, 2H); 3.52 (A of ABX, dd, J=12.4, 4.6 Hz, 1H); 3.40 (B of ABX, dd, J=12.4, 4.6 Hz, 1H); 3.00 (A of ABX, dd, J=13.5, 6.4 Hz, 1H); 2.92 (B of ABX, dd, J=13.5, 7.4 Hz, 1H); 1.29 (t, J=7 Hz, 3H).

Step C (S)-[3-(1-Aminomethyl-2-phenyl-ethylamino)-6-chloro-2-oxo-2H-pyrazin-1-yl]-acetic acid ethyl ester (23-3)

To a solution of (S)-[3-(1-azidomethyl-2-phenyl-ethylamino)-6-chloro-2-oxo-2H-pyrazin-1-yl]-acetic acid ethyl ester (5.67 g, 14.5 mmol) in MeOH (80 ml) and THF (40 ml) was added SnCl$_2$ (4.1 g, 21.8 mmol) and the reaction mixture was stirred at room temperature for 18 h. The reaction mixture was concentrated in vacuo, azeotroped with CH$_2$Cl$_2$, and purified by flash chromatography (silica gel, 6% MeOH containing 10% NH$_4$OH in CH$_2$Cl$_2$ to 10%) to give (S)-[3-(1-aminomethyl-2-pheny-ethylamino)-6-chloro-2-oxo-2H-pyrazin-1-yl]-acetic acid ethyl ester as a beige solid. $^1$H NMR (CDCl$_3$, 400 MHz): δ 7.35–7.15 (m, 5H); 6.92 (s, 1H); 6.17 (bd, J=8.5 Hz, 1H); 4.88 (s, 2H));); 4.35–4.15(m, 3H); 3.00–2.70 (m, 4H); 1.32 (t, J=6.9 Hz, 3 H); rotation: [α]$_d$=−82.6° (c=0.42, MeOH).

Step D

[6-Chloro-(S)-3-(1-dimethylaminomethyl-2-phenyl-ethylamino)-2-oxo-2H-pyrazin-1-yl]-acetic acid ethyl ester (23-4)

To a solution of (S)-[3-(1-aminomethyl-2-phenyl-ethylamino)-6-chloro-2-oxo-2H-pyrazin-1-yl]-acetic acid ethyl ester (700 mg, 1.92 mmol) in DCE (20 ml) was added formaldehyde (719 ul of a 37% solution in water, 9.59 mmol) and sodium triacetoxyborohydride (813 mg, 3.84 mmol) and the reaction mixture was stirred at room temperature for 1.5 h. The reaction mixture was diluted with CH$_2$Cl$_2$ and quenched with 1N NaOH and water, and stirred at room temperature for 5 min. The organic layer was separated and the aqueous layer extracted with CH$_2$Cl$_2$ twice. The combined organic layer was washed with brine, dried on Na$_2$SO$_4$, and purified by flash chromatography (silica gel, 2% MeOH containing 10% NH$_4$OH in CH$_2$Cl$_2$ to 4%) to give [6-chloro-(S)-3-(1-dimethylaminomethyl-2-phenyl-ethylamino)-2-oxo-2H-pyrazin-1-yl]-acetic acid ethyl ester as an oil. $^1$H NMR (CDCl$_3$, 400 MHz): δ 7.35–7.15 (m, 5H); 6.93 (s, 1H); 6.15 (bd, J=6.9 Hz, 1H); 4.92 (A of AB, d, J=17 Hz, 1H); 4.86 (B of AB, d, J=17 Hz, 1H); 4.32–4.22 (m, 1H); 4.27 (q, J=7.5 Hz, 2H); 3.05 (A of ABX, dd, J=13.6, 4.8 Hz, 1H); 2.87 (B of ABX, dd, J=13.6, 6.1 Hz, 1H); 2.37 (A of ABX, dd, J=12.2, 8.3 Hz, 1H); 2.27 (B of ABX, dd, J=12.2, 6.1 Hz, 1H); 1.29 (t, J=7.5 Hz, 3H).

Step E

[6-Chloro-(S)-3-(1-dimethylaminomethyl-2-phenyl-ethylamino)-2-oxo-2H-pyrazin-1-yl]-acetic acid (23-5)

To a solution of [6-chloro-(S)-3-(1-dimethylaminomethyl-2-phenyl-ethylamino)-2oxo-2H-pyrazin-1-yl]-acetic acid ethyl ester (385 mg, 0.98 mmol) in THF (6 ml) is added 1N LiOH (1.27 ml, 1.27 mmol) and the reaction mixture is stirred at room temperature for 3 h. To the reaction mixture is added 1N HCl (1.27 ml, 1.27 mmol) and the mixture is concentrated in vacuo, azeotroped with methanol and dried on high vacuum to give [6-chloro-(S)-3-(1-dimethylaminomethyl-2-phenylethylamino)-2-oxo-2H-pyrazin-1-yl]-acetic acid as a white solid which contains 1.3 eq LiCl. $^1$H NMR (CD$_3$OD, 400 MHz): δ 7.30–7.15 (m, 5H); 6.86 (s, 1H); 4.80 (A of AB, d, J=16.7 Hz, 1H); 4.76–4.66 (m, 1H); 4.56 (B of AB, d, J=16.7 Hz, 1H); 3.45 (A of ABX, dd, J=13, 12.9 Hz, 1H); 3.25 (B of ABX, dd, J=13, 3.4 Hz, 1H); 3.00–2.85 (m, 2H).

EXAMPLE 24

2-[6-Chloro-3-(2,2-difluoro-2-pyridin-2-yl-ethylamino)-2-oxo-2H-pyrazin-1-yl]-N-(2-[1,2,3]thiadiazol-4-yl-benzyl)-acetamide

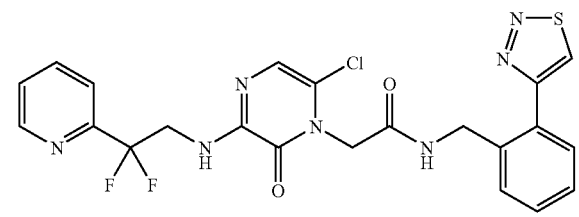

Step A

2-[6-Chloro-3-(2,2-difluoro-2-pyridin-2-yl-ethylamino)-2-oxo-2H-pyrazin-1-yl]-N-(2-[1,2,3]thiadiazol-4-yl-benzyl)-acetamide (24-1)

A solution of [6-chloro-3-(2,2-difluoro-2-pyridin-2-yl-ethylamino)-2-oxo-2H-pyrazin-1-yl]-acetic acid (70 mg, 0.16 mmol, preparation described in example 17), 2-[1,2,3]thiadiazole4-yl-benzylamine (40 mg, 0.21 mmol, preparation described in example 1), 1-(3-dimethylaminopropyl)-3-ethylcarbodiimide hydrochloride (46 mg, 0.24 mmol), 1-hydroxy-7-azabenzotriazole (33 mg, 0.24 mmol) and diisopropylethylamine (42 ul, 0.24 mmol) in N,N-dimethylformamide (2 ml) was stirred at room temperature overnight. Water was added and the reaction mixture was extracted with ethyl acetate. The combined organic layers were washed with brine. Drying and solvent evaporation gave an oil; flash chromatography (silica gel, chloroform-2-propanol-ammonium hydroxide, 99:1:0.1–98:2:0.2) gave 2-[6-chloro-3-(2,2-difluoro-2-pyridin-2-yl-ethylamino)-2-oxo-2H-pyrazin-1-yl]-N-(2-[1,2,3]thiadiazol-4-yl-benzyl)-acetamide; $^1$H NMR (CDCl$_3$, 400 MHz) δ 8.66 (m, 2H), 7.82 (dt, 1H, J=7.8 Hz, J=1.6 Hz), 7.69 (m, 1H), 7.64 (m, 1H), 7.53 (m, 1H), 7.48–7.38 (m, 3H), 6.92 (s, 1H), 6.47 (t, 1H, J=6 Hz), 4.81 (s, 2H), 4.47 (d, 2H, J=6.3 Hz), 4.36 (dt, 2H, J=14 Hz, J=6.4 Hz); MS (ES+) M+1 518.45 for C$_{22}$H$_{18}$ClF$_2$N$_7$O$_2$.

EXAMPLE 25

2-{6-Chloro-3-[2,2-difluoro-2-(1-oxy-pyridin-2-yl)-ethylamino]-2-oxo-2H-pyrazin-1-yl}-N-(2-[1,2,3]thiadiazol-4-yl-benzyl)-acetamide

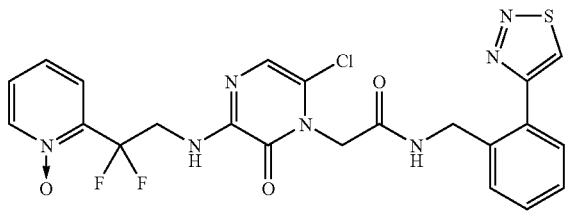

Step A

2-{6-Chloro-3-[2,2-difluoro-2-(1-oxy-pyridin-2-yl)-ethylamino]-2-oxo-2H-pyrazin-1-yl}-N-(2-[(1,2,3]thiadiazol-4-yl-benzyl)-acetamide (25-1)

A solution of {6-chloro-3-[2,2-difluoro-2-(1-oxy-pyridin-2-yl)-ethylamino]-2-oxo-2H-pyrazin-1-yl}-acetic acid (75 mg, 0.16 mmol, preparation described in example 18), 2-[1,2,3]thiadiazole-4-yl-benzylamine (40 mg, 0.21 mmol, preparation described in example 1), 1-(3-dimethylaminopropyl)-3-ethylcarbodiimide hydrochloride (46 mg, 0.24 mmol), 1-hydroxy-7-azabenzotriazole (33 mg, 0.24 mmol) and diisopropylethylamine (42 ul, 0.24 mmol) in N,N-dimethylformamide (2 ml) was stirred at room temperature overnight. Water was added and the reaction mixture was extracted with ethyl acetate. The combined organic layers were washed with brine. Drying and solvent evaporation gave an oil; flash chromatography (silica gel, chloroform saturated with ammonia-2-propanol 98:2) gave 2-{6-chloro-3-[2,2-difluoro-2-(1-oxy-pyridin-2-yl)-ethylamino]-2-oxo-2H-pyrazin-1-yl}-N-(2-[1,2,3]thiadiazol-4-yl-benzyl)-acetamide; $^1$H NMR (CDCl$_3$, 400 MHz) δ 8.66 (s, 1H), 8.25 (d, 1H, J=6.4 Hz), 7.62 (m, 2H), 7.54 (m, 1H), 7.44 (m, 2H), 7.32 (m, 2H), 6.83 (s, 1H), 6.35 (t, 1H, J=8 Hz), 4.79 (s, 2H), 4.63 (m, 2H), 4.45 (d, 2H, J=6.3 Hz); MS (ES+) M+1 534.4 for C$_{22}$H$_{18}$ClF$_2$N$_7$O$_3$S.

EXAMPLE 26

2-[6-Chloro-3-(2,2-difluoro-2-pyridin-2-yl-ethylamino)-2-oxo-2H-pyrazin-1-yl]-N-(2-tetrazol-1-yl-benzyl)-acetamide trifluoroacetic acid salt

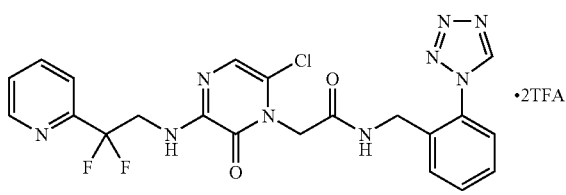

Prepared following a similar protocol as described in example 24, [6-chloro-3-(2,2-difluoro-2-pyridin-2-yl-ethylamino)-2-oxo-2H-pyrazin-1-yl]-acetic acid (preparation described in example 17) and 2-tetrazol-1-yl-benzylamine (preparation described in example 3) were converted to 2-[6-chloro-3-(2,2-difluoro-2-pyridin-2-yl-ethylamino)-2-oxo-2H-pyrazin-1-yl]-N-(2-tetrazol-1-yl-benzyl)-acetamide trifluoroacetic acid salt; MS (ES+) M+1 502.4 for C$_{21}$H$_{18}$ClF$_2$N$_9$O$_2$.

EXAMPLE 27

2-{6-Chloro-3-[2,2-difluoro-2-(1-oxy-pyridin-2-yl)-ethylamino]-2-oxo-2H-pyrazin-1-yl}-N-(2-tetrazol-1-yl-benzyl)-acetamide

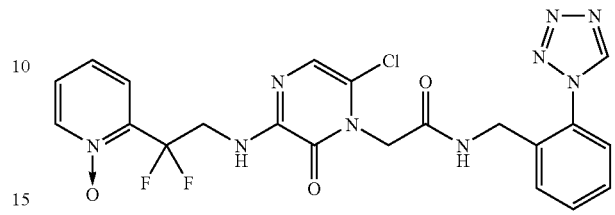

Prepared following a similar protocol as described in example 24, {6-chloro-3-[2,2-difluoro-2-(1-oxy-pyridin-2-yl)-ethylamino]-2-oxo-2H-pyrazin-1-yl}-acetic acid (preparation described in example 18) and 2-tetrazol-1-yl-benzylamine (preparation described in example 3) were converted to 2-{6-chloro-3-[2,2-difluoro-2-(1-oxy-pyridin-2-yl)-ethylamino]-2-oxo-2H-pyrazin-1-yl}-N-(2-tetrazol-1-yl-benzyl)-acetamide; MS (ES+) M+1 518.5 for C$_{21}$H$_{18}$ClF$_2$N$_9$O$_3$.

EXAMPLE 28

2-[6-Chloro-3-(2,2-difluoro-2-pyridin-2-yl-ethylamino)-2-oxo-2H-pyrazin-1-yl]-N-(2-pyrazol-1-yl-benzyl)-acetamide

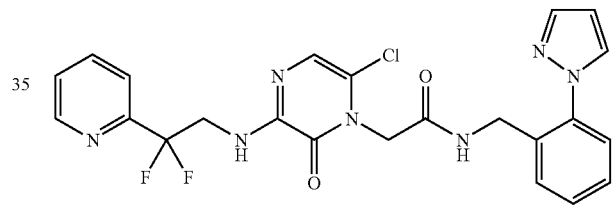

Prepared following a similar protocol as described in example 24, [6-chloro-3-(2,2-difluoro-2-pyridin-2-yl-ethylamino)-2-oxo-2H-pyrazin-1-yl]-acetic acid (preparation described in example 17) and 2-pyrazol-1-yl-benzylamine trifluoroacetic acid salt (preparation described in example 5) were converted to 2-[6-chloro-3-(2,2-difluoro-2-pyridin-2-yl-ethylamino)-2-oxo-2H-pyrazin-1-yl]-N-(2-pyrazol-1-yl-benzyl)-acetamide; MS (ES+) M+1 500.4 for C$_{23}$H$_{20}$ClF$_2$N$_7$O$_2$.

EXAMPLE 29

2-[6-Chloro-3-(2,2-difluoro-2-pyridin-2-yl-ethylamino)-2-oxo-2H-pyrazin-1-yl]-N-[2-(1H-imidazol-2-yl)-benzyl]-acetamide

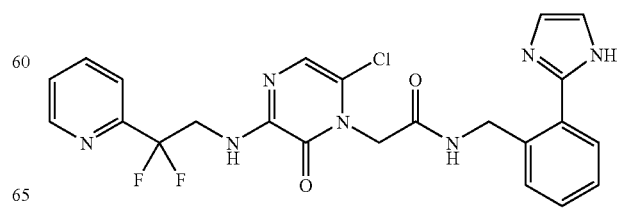

Prepared following a similar protocol as described in example 24, [6-chloro-3-(2,2-difluoro-2-pyridin-2-yl-ethylamino)-2-oxo-2H-pyrazin-1-yl]-acetic acid (preparation described in example 17) and 2-(1H-imidazol-2-yl)-benzylamine (preparation described in example 6) were converted to 2-[6-chloro-3-(2,2-difluoro-2-pyridin-2-yl-ethylamino)-2-oxo-2H-pyrazin-1-yl]-N-[2-(1H-imidazol-2-yl)-benzyl]-acetamide; MS (ES+) M+1 500.5 for $C_{23}H_{20}ClF_2N_7O_2$.

EXAMPLE 30

2-[6-Chloro-3-(2,2-difluoro-2-pyridin-2-yl-ethylamino)-2-oxo-2H-pyrazin-1-yl]-N-(2-[1,2,4]triazol-1-yl-benzyl)-acetamide

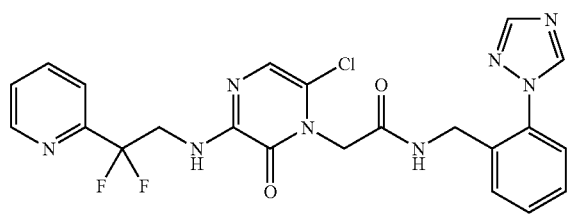

Prepared following a similar protocol as described in example 24, [6-chloro-3-(2,2-difluoro-2-pyridin-2-yl-ethylamino)-2-oxo-2H-pyrazin-1-yl]-acetic acid (preparation described in example 17) and 2-(1,2,4-triazol-1-yl)benzylamine (preparation described in example 9) were converted to 2-[6-chloro-3-(2,2-difluoro-2-pyridin-2-yl-ethylamino)-2-oxo-2H-pyrazin-1-yl]-N-(2-[1,2,4]triazol-1-yl-benzyl)-acetamide; MS (ES+) M+1 501.5 for $C_{22}H_{19}ClF_2N_8O_2$.

EXAMPLE 31

2-{6-Chloro-3-[2,2-difluoro-2-(1-oxy-pyridin-2-yl)-ethylamino]-2-oxo-2H-pyrazin-1-yl}-N-(2-[1,2,4]triazol-1-yl-benzyl)-acetamide trifluoroacetic acid salt

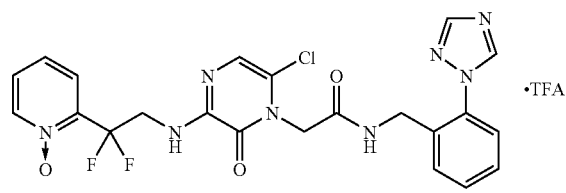

Prepared following a similar protocol as described in example 24, {6-chloro-3-[2,2-difluoro-2-(1-oxy-pyridin-2-yl)-ethylamino]-2-oxo-2H-pyrazin-1-yl}-acetic acid (preparation described in example 18) and 2-(1,2,4-triazol-1-yl) benzylamine (preparation described in example 9) were converted to 2-{6-chloro-3-[2,2-difluoro-2-(1-oxy-pyridin-2-yl)-ethylamino]-2-oxo-2H-pyrazin-1-yl}-N-(2-[1,2,4]triazol-1-yl-benzyl)-acetamide trifluoroacetic acid salt; MS (ES+) M+1 517.5 for $C_{22}H_{19}ClF_2N_8O_3$.

EXAMPLE 32

2-[6-Chloro-3-(2,2-difluoro-2-pyridin-2-yl-ethylamino)-2-oxo-2H-pyrazin-1-yl]-N-(2-imidazol-1-yl-benzyl)-acetamide trifluoroacetic acid salt

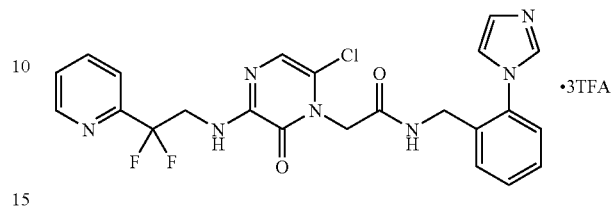

Prepared following a similar protocol as described in example 24, [6-chloro-3-(2,2-difluoro-2-pyridin-2-yl-ethylamino)-2-oxo-2H-pyrazin-1-yl]-acetic acid (preparation described in example 17) and 2-imidazol-1-yl-benzylamine (preparation described in example 13) were converted to 2-[6-chloro-3-(2,2-difluoro-2-pyridin-2-yl-ethylamino)-2-oxo-2H-pyrazin-1-yl]-N-(2-imidazol-1-yl-benzyl)-acetamide trifluoroacetic acid salt; MS (ES+) M+1 500.51 for $C_{23}H_{20}ClF_2N_7O_2$.

EXAMPLE 33

2-[6-Chloro-3-(2,2-difluoro-2-pyridin-2-yl-ethylamino)-2-oxo-2H-pyrazin-1-yl]-N-(2-[1,2,4]triazol-4-yl-benzyl)-acetamide trifluoroacetic acid salt

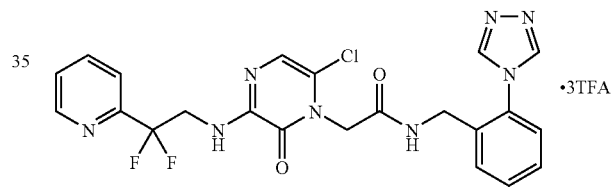

Prepared following a similar protocol as described in example 24, [6-chloro-3-(2,2-difluoro-2-pyridin-2-yl-ethylamino)-2-oxo-2H-pyrazin-1-yl]-acetic acid (preparation described in example 17) and 2-(1,2,4-triazol-4-yl)benzylamine (preparation described in example 10) were converted to 2-[6-chloro-3-(2,2-difluoro-2-pyridin-2-yl-ethylamino)-2-oxo-2H-pyrazin-1-yl]-N-(2-[1,2,4]triazol-4-yl-benzyl)-acetamide trifluoroacetic acid salt; MS (ES+) M+1 501.5 for $C_{22}H_{19}ClF_2N_8O_2$.

EXAMPLE 34

2-[6-Chloro-3-(2,2-difluoro-2-pyridin-2-yl-ethylamino)-2-oxo-2H-pyrazin-1-yl]-N-(3-[1,2,4]triazol-1-yl-pyridin-2-yl-methyl)-acetamide trifluoroacetic acid salt

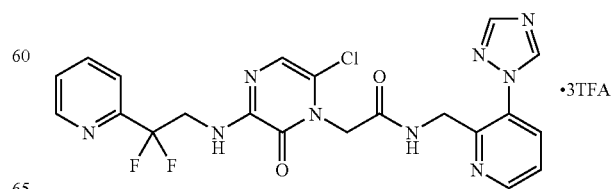

Prepared following a similar protocol as described in example 24, [6-chloro-3-(2,2-difluoro-2-pyridin-2-yl-ethylamino)-2-oxo-2H-pyrazin-1-yl]-acetic acid (preparation described in example 17) and C-(3-[1,2,4]triazol-1-yl-pyridin-2-yl)-methylamine 15 hydrochloride salt (preparation described in example 7) were converted to 2-[6-chloro-3-(2,2-difluoro-2-y-ethylamino)-2-oxo-2H-pyrazin-1-yl]-N-(3-[1,2,4]triazol-1-yl-pyridin-2-ylmethyl)-acetamide trifluoroacetic acid salt; MS (ES+) M+1 502.5 for $C_{21}H_{18}ClF_2N_9O_2$.

EXAMPLE 35

2-{6-Chloro-3-[2,2-difluoro-2-(1-oxy-pyridin-2-yl)-ethylamino]-2-oxo-2H-pyrazin-1-yl}-N-(3-[1,2,4]triazol-1-yl-pyridin-2-ylmethyl)-acetamide

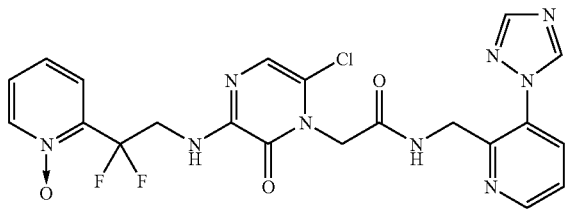

Prepared following a similar protocol as described in example 24, {6-chloro-3-[2,2-difluoro-2-(1-oxy-pyridin-2-yl}-ethylamino]-2-oxo-2H-pyrazin-1-yl)-acetic acid (preparation described in example 18) and C-(3-[1,2,4]triazol-1-yl-pyridin-2-yl)-methylamine hydrochloride salt (preparation described in example 7) were converted to 2-{6-chloro-3-[2,2-difluoro-2-(1-oxy-pyridin-2-yl)-ethylamino]-2-oxo-2H-pyrazin-1-yl}-N-(3-[1,2,4]triazol-1-yl-pyridin-2-ylmethyl)-acetamide; MS (ES+) M+1 518.4 for $C_{21}H_{18}ClF_2N_9O_3$.

EXAMPLE 36

2-[6-Chloro-3-(2,2-difluoro-2-pyridin-2-yl-ethylamino)-2-oxo-2H-pyrazin-1-yl]-N-(5-chloro-2-tetrazol-1-yl-benzyl)-acetamide

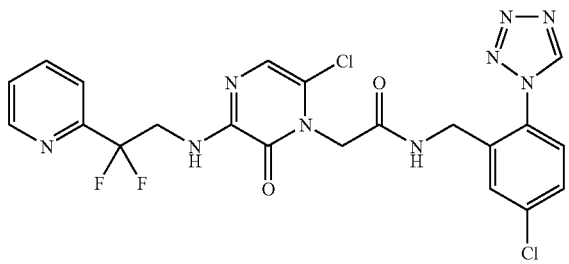

Prepared following a similar protocol as described in example 24, (6-chloro-3-(2,2-difluoro-2-pyridin-2-yl-ethylamino)-2-oxo-2H-pyrazin-1-yl]-acetic acid (preparation described in example 17) and 5-chloro-2-tetrazol-1-yl-benzylamine (preparation described in example 4) were converted to 2-[6-chloro-3-(2,2-difluoro-2-pyridin-2-yl-ethylamino)-2-oxo-2H-pyrazin-1-yl]-N-(5-chloro-2-tetrazol-1-yl-benzyl)-acetamide; MS (ES+) M+1 536.4 for $C_{21}H_{17}Cl_2F_2N_9O_2$.

EXAMPLE 37

2-{6-Chloro-3-[2,2-difluoro-2-(1-oxy-pyridin-2-yl)-ethylamino]-2-oxo-2H-pyrazin-1-yl}-N-(5-chloro-2-tetrazol-1-yl-benzyl)-acetamide

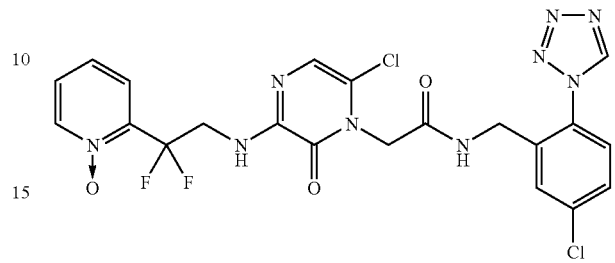

Prepared following a similar protocol as described in example 24, {6-chloro-3-[2,2-difluoro-2-(1-oxy-pyridin-2-yl)-ethylamino]-2-oxo-2H-pyrazin-1-yl}-acetic acid (preparation described in example 18) and 5-chloro-2-tetrazol-1-yl-benzylamine (preparation described in example 4) were converted to 2-{6-chloro-3-[2,2-difluoro-2-(1-oxy-pyridin-2-yl)-ethylamino]-2-oxo-2H-pyrazin-1-yl}-N-(5-chloro-2-tetrazol-1-yl-benzyl)-acetamide; MS (ES+) M+1 552.3 for $C_{21}H_{17}Cl_2F_2N_9O_3$.

EXAMPLE 38

2-[6-Chloro-3-(2,2-difluoro-2-pyridin-2-yl-ethylamino)-2-oxo-2H-pyrazin-1-yl]-N-[2-(1H-imidazol-4-yl)-benzyl]-acetamide trifluoroacetic acid salt

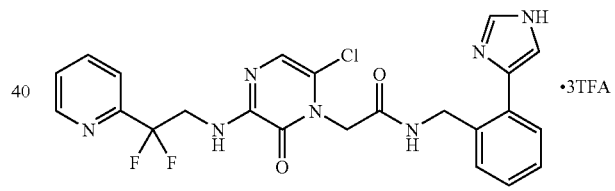

Step A

2-[6-Chloro-3-(2,2-difluoro-2-pyridin-2-yl-ethylamino)-2-oxo-2H-pyrazin-1-yl]-N-[2-(1-trityl-1H-imidazol-4-yl)-benzyl]-acetamide A solution of [6-chloro-3-(2,2-difluoro-2-pyridin-2-yl-ethylamino)-2-oxo-2H-pyrazin-1-yl]-acetic acid (25 mg, 0.058 mmol, preparation described in example 17), 2-(1-trityl-1H-imidazol-4-yl)-benzylamine oxalate salt (35 mg, 0.070 mmol, preparation described in example 2), 1-(3-dimethylaminopropyl)-3-ethylcarbodiimide hydrochloride (17 mg, 0.087 mmol), 1-hydroxy-7-azabenzotriazole (12 mg, 0.087 mmol) and diisopropylethylamine (40 ul, 0.23 mmol) in N,N-dimethylformamide (1 ml) was stirred at room temperature overnight. Water was added and the reaction mixture was extracted with ethyl acetate. The combined organic layers were washed with brine. Drying and solvent evaporation gave 2-[6-chloro-3-(2,2-difluoro-2-pyridin-2-yl-ethylamino)-2-oxo-2H-pyrazin-1-yl]-N-[2-(1-trityl-1H-imidazol-4-yl)-benzyl]-acetamide; $^1$H NMR (CDCl$_3$, 300 MHz) δ 9.11 (m, 1H), 8.65 (d, 1H, J=4.6 Hz), 8.02 (s, 1H), 7.80 (m, 1H), 7.61 (m, 1H), 7.47 (m, 1H), 7.38–7.15 (m, 18H), 6.99 (d, 1H, J=1.2 Hz), 6.78 (s, 1H), 6.36 (m, 1H), 4.78 (s, 2H), 4.43 (d, 2H, J=6.4 Hz), 4.14 (m, 2H).

Step B

2-[6-Chloro-3-(2,2-difluoro-2-pyridin-2-yl-ethylamino)-2-oxo-2H-pyrazin-1-yl]-N-[2-(1H-imidazol-4-yl)-benzyl]-acetamide trifluoroacetic acid salt To a solution of 2-[6-chloro-3-(2,2-difluoro-2-pyridin-2-yl-ethylamino)-2-oxo-2H-pyrazin-1-yl]-N-[2-(1-trityl-1H-imidazol-4-yl)-benzyl]-acetamide (47 mg, 0.058 mmol) in trifluoroacetic acid (1.5 ml) was added triethylsilane (excess) until completion of the reaction. Concentration and purification by reverse phase preparative HPLC (5% to 95% $CH_3CN$ in water containing 0.1% TFA, C18 PRO YMC 20×150 mm) gave 2-[6-chloro-3-(2,2-difluoro-2-pyridin-2-yl-ethylamino)-2-oxo-2H-pyrazin-1-yl]-N-[2-(1H-imidazol-4-yl)-benzyl]-acetamide TFA salt; $^1$H NMR ($CD_3OD$, 400 MHz) δ 8.95 (d, 1H, J=1.3 Hz), 8.63 (d, 1H, J=4.1 Hz), 7.94 (dt, 1H, J=7.7 Hz, J=1.6 Hz), 7.70 (m, 2H), 7.51 (m, 6H), 6.83 (s, 1H), 4.80 (s, 2H), 4.46 (s, 2H), 4.28 (t, 2H, J=14.1 Hz); MS (ES+) M+1 500.4 for $C_{23}H_{20}ClF_2N_7O_2$.

EXAMPLE 39

2-[6-Chloro-3-(2,2-difluoro-2-pyridin-2-yl-ethylamino)-2-oxo-2H-pyrazin-1-yl]-N-[2-(1H-tetrazol-5-yl)-benzyl]-acetamide trifluoroacetic acid salt

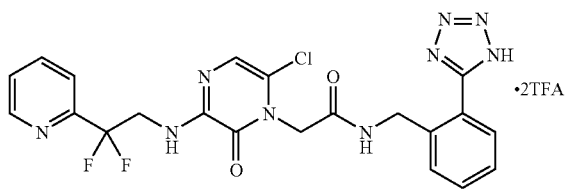

Prepared following a similar protocol as described in example 24, [6-chloro-3-(2,2-difluoro-2-pyridin-2-yl-ethylamino)-2-oxo-2H-pyrazin-1-yl]-acetic acid (preparation described in example 17) and 2-(1H-tetrazol-5-yl)-benzylamine hydrochloride salt (preparation described in example 14) were converted to 2-[6-chloro-3-(2,2-difluoro-2-pyridin-2-yl-ethylamino)-2-oxo-2H-pyrazin-1-yl]-N-[2-(1H-tetrazol-5-yl)-benzyl]-acetamide trifluoroacetic acid salt; MS (ES+) M+1 502.4 for $C_{21}H_{18}ClF_2N_9O_2$.

EXAMPLE 40

2-[6-Chloro-3-(2,2-difluoro-2-pyridin-2-yl-ethylamino)-2-oxo-2H-pyrazin-1-yl]-N-(5-chloro-2-[1,2,4]triazol-1-yl-benzyl)-acetamide trifluoroacetic acid salt

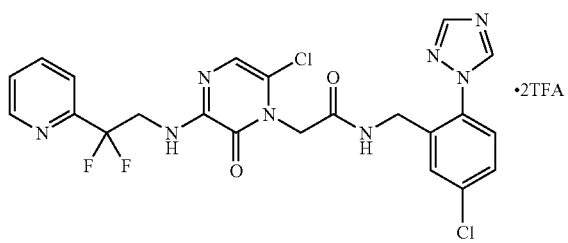

Prepared following a similar protocol as described in example 24, [6-chloro-3-(2,2-difluoro-2-pyridin-2-yl-ethylamino)-2-oxo-2H-pyrazin-1-yl]-acetic acid (preparation described in example 17) and 5-chloro-2-[1,2,4]triazol-1-yl-benzylamine (preparation described in example 8) were converted to 2-[6-chloro-3-(2,2-difluoro-2-pyridin-2-yl-ethylamino)-2-oxo-2H-pyrazin-1-yl]-N-(5-chloro-2-[1,2,4]triazol-1-yl-benzyl)-acetamide trifluoroacetic acid salt;

MS (ES+) M+1 535.4 for $C_{22}H_{18}Cl_2F_2N_8O_2$.

EXAMPLE 41

2-{6-Chloro-3-[2,2-difluoro-2-(1-oxy-pyridin-2-yl)-ethylamino]-2-oxo-2H-pyrazin-1-yl}-N-(5-chloro-2-[1,2,4]triazol-1-yl-benzyl)-acetamide trifluoroacetic acid salt

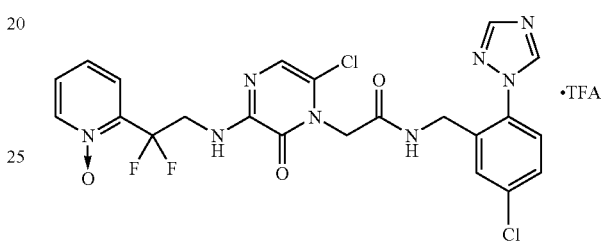

Prepared following a similar protocol as described in example 24, {6-chloro-3-[2,2-difluoro-2-(1-oxy-pyridin-2-yl)-ethylamino]-2-oxo-2H-pyrazin-1-yl}-acetic acid (preparation described in example 18) and 5-chloro-2-[1,2,4]triazol-1-yl-benzylamine (preparation described in example 8) were converted to 2-{6-chloro-3-[2,2-difluoro-2-(1-oxy-pyridin-2-yl)-ethylamino]-2-oxo-2H-pyrazin-1-yl}-N-(5-chloro-2-[1,2,4]triazol-1-yl-benzyl)-acetamide trifluoroacetic acid salt; MS (ES+) M+1 551.4 for $C_{22}H_{18}Cl_2F_2N_8O_3$.

EXAMPLE 42

2-[6-Chloro-3-(2,2-difluoro-2-pyridin-2-yl-ethylamino)-2-oxo-2H-pyrazin-1-yl]-N-(3-tetrazol-1-yl-pyridin-2-ylmethyl)-acetamide

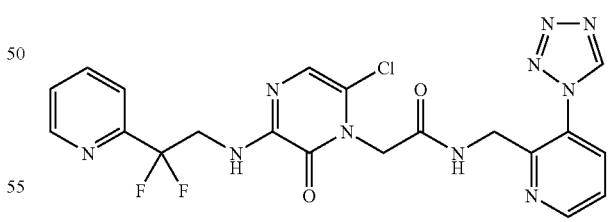

Prepared following a similar protocol as described in example 24, [6-chloro-3-(2,2-difluoro-2-pyridin-2-yl-ethylamino)-2-oxo-2H-pyrazin-1-yl]-acetic acid (preparation described in example 17) and 3-(tetrazol-1-yl)-2-aminomethylpyridine (preparation described in example 11) were converted to 2-[6-chloro-3-(2,2-difluoro-2-pyridin-2-yl-ethylamino)-2-oxo-2H-pyrazin-1-yl]-N-(3-tetrazol-1-yl-pyridin-2-ylmethyl)-acetamide; MS (ES+) M+1 503.4 for $C_{20}H_{17}ClF_2N_{10}O_2$.

EXAMPLE 43

2-{6-Chloro-3-[2,2-difluoro-2-(1-oxy-pyridin-2-yl)-ethylamino]-2-oxo-2H-pyrazin-1-yl}-N-(3-tetrazol-1-yl-pyridin-2-ylmethyl)-acetamide trifluoroacetic acid salt

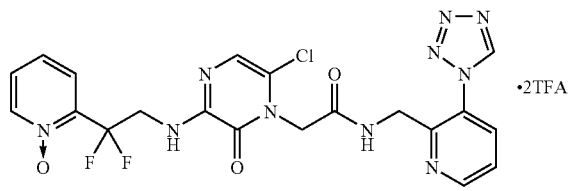

Prepared following a similar protocol as described in example 24, {6-chloro-3-[2,2-difluoro-2-(1-oxy-pyridin-2-yl]-ethylamino]-2-oxo-2H-pyrazin-1-yl)-acetic acid (preparation described in example 18) and 3-(tetrazol-1-yl)-2-aminomethylpyridine (preparation described in example 11) were converted to 2-{6-chloro-3-[2,2-difluoro-2-(1-oxy-pyridin-2-yl)-ethylamino]-2-oxo-2H-pyrazin-1-yl}-N-(3-tetrazol-1-yl-pyridin- 2-ylmethyl)-acetamide trifluoroacetic acid salt; MS (ES+) M+1 519.0 for $C_{20}H_{17}ClF_2N_{10}O_3$.

EXAMPLE 44

2-[6-Chloro-3-(2,2-difluoro-2-pyridin-2-yl-ethylamino)-2-oxo-2H-pyrazin-1-yl]-N-[2-(1H-pyrazol-3-yl)-benzyl]-acetamide trifluoroacetic acid salt

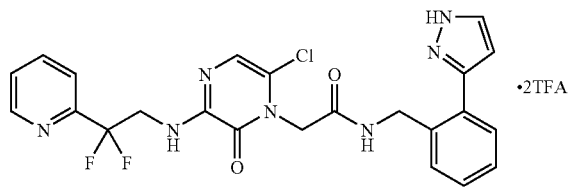

Prepared following a similar protocol as described in example 24, [6-chloro-3-(2,2-difluoro-2-pyridin-2-yl-ethylamino)-2-oxo-2H-pyrazin-1-yl]-acetic acid (preparation described in example 17) and 2-(1H-pyrazol-3-yl)-benzylamine hydrochloride salt (preparation described in example 12) were converted to 2-[6-chloro-3-(2,2-difluoro-2-pyridin-2-yl-ethylamino)-2-oxo-2H-pyrazin-1-yl]-N-[2-(1H-pyrazol-3-yl)-benzyl]-acetamide trifluoroacetic acid salt; MS (ES+) M+1 500.1 for $C_{23}H_{20}ClF_2N_7O_2$.

EXAMPLE 45

2-[6-Chloro-3-(2,2-difluoro-2-pyridin-2-yl-ethylamino)-2-oxo-2H-pyrazin-1-yl]-N-[2-(1-methyl-1H-tetrazol-5-yl)-benzyl]-acetamide trifluoroacetic acid salt

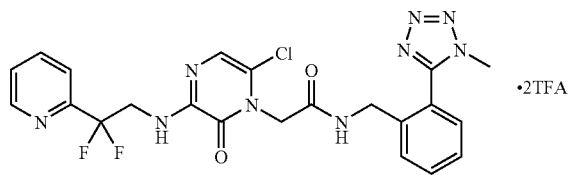

Prepared following a similar protocol as described in example 24, [6-chloro-3-(2,2-difluoro-2-pyridin-2-yl-ethylamino)-2-oxo-2H-pyrazin-1-yl]-acetic acid (preparation described in example 17) and 2-(1-methyl-1H-tetrazol-5-yl)-benzylamine hydrochloride salt (preparation described in example 15) were converted to 2-[6-Chloro-3-(2,2-difluoro-2-pyridin-2-yl-ethylamino)-2-oxo-2H-pyrazin-1-yl]-N-[2-(1-methyl-1H-tetrazol-5-yl)-benzyl]-acetamide trifluoroacetic acid salt; MS (ES+) M+1 516.4 for $C_{22}H_{20}ClF_2N_9O_2$.

EXAMPLE 46

2-[6-Chloro-3-(2,2-difluoro-2-pyridin-2-yl-ethylamino)-2-oxo-2H-pyrazin-1-yl]-N-[2-(2-methyl-2H-tetrazol-5-yl)-benzyl]-acetamide trifluoroacetic acid salt

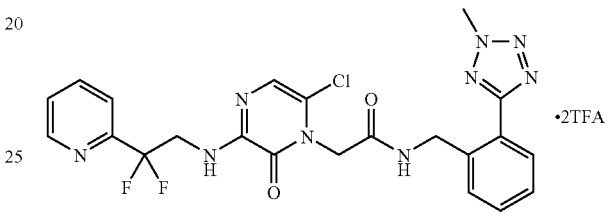

Prepared following a similar protocol as described in example 24, [6-chloro-3-(2,2-difluoro-2-pyridin-2-yl-ethylamino)-2-oxo-2H-pyrazin-1-yl]-acetic acid (preparation described in example 17) and 2-(2-methyl-2H-tetrazol-5-yl)-benzylamine hydrochloride salt (preparation described in example 16) were converted to 2-[6-Chloro-3-(2,2-difluoro-2-pyridin-2-yl-ethylamino)-2-oxo-2H-pyrazin-1-yl]-N-[2-(2-methyl-2H-tetrazol-5-yl)-benzyl]-acetamide trifluoroacetic acid salt; MS (ES+) M+1 516.4 for $C_{22}H_{20}ClF_2N_9O_2$.

EXAMPLE 47

N-(5-Chloro-2-tetrazol-1-yl-benzyl)-2-[3-(2,2-difluoro-2-pyridin-2-yl-ethylamino)-2-oxo-2H-pyrazin-1-yl]-acetamide

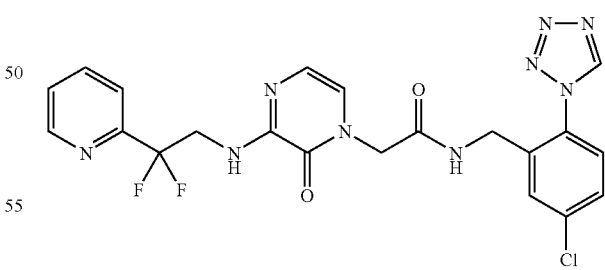

Prepared following a similar protocol as described in example 24, [3-(2,2-difluoro-2-pyridin-2-yl-ethylamino)-2-oxo-2H-pyrazin-1-yl]acetic acid (preparation described in example 19) and 5-chloro-2-tetrazol-1-yl-benzylamine (preparation described in example 4) were converted to N-(5-chloro-2-tetrazol-1-yl-benzyl)-2-[3-(2,2-difluoro-2-pyridin-2-yl-ethylamino)-2-oxo-2H-pyrazin-1-yl]-acetamide; MS (ES+) M+1 502.4 for $C_{21}H_{18}ClF_2N_9O_2$.

EXAMPLE 48

2-[3-(2,2-Difluoro-2-pyridin-2-yl-ethylamino)-2-oxo-2H-pyrazin-1-yl]-N-(2-[1,2,4]triazol-1-yl-benzyl)-acetamide

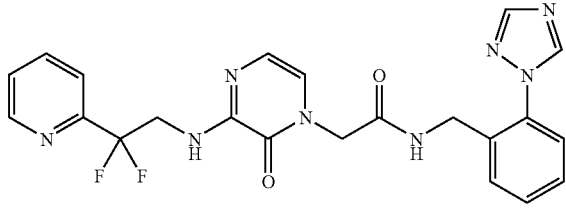

Prepared following a similar protocol as described in example 24, [3-(2,2-difluoro-2-pyridin-2-yl-ethylamino)-2-oxo-2H-pyrazin-1-yl]acetic acid (preparation described in example 19) and 2-(1,2,4-triazol-1-yl)benzylamine (preparation described in example 9) were converted to 2-[3-(2,2-difluoro-2-pyridin-2-yl-ethylamino)-2-oxo-2H-pyrazin-1-yl]-N-(2-[1,2,4]triazol-1-yl-benzyl)-acetamide; MS (ES+) M+1 467.1 for $C_{22}H_{20}F_2N_8O_2$.

EXAMPLE 49

N-(5-Chloro-2-[1,2,4]triazol-1-yl-benzyl)-2-[3-(2,2-difluoro-2-pyridin-2-yl-ethylamino)-2-oxo-2H-pyrazin-1-yl]-acetamide

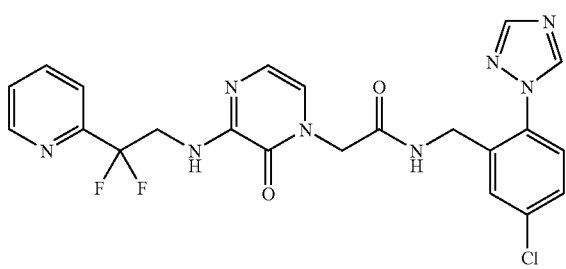

Prepared following a similar protocol as described in example 24, [3-(2,2-difluoro-2-pyridin-2-yl-ethylamino)-2-oxo-2H-pyrazin-1-yl]acetic acid (preparation described in example 19) and 5-chloro-2-[1,2,4]triazol-1-yl-benzylamine (preparation described in example 8) were converted to N-(5-chloro-2-[1,2,4]triazol-1-yl-benzyl)-2-[3-(2,2-difluoro-2-pyridin-2-yl-ethylamino)-2-oxo-2H-pyrazin-1-yl]-acetamide; MS (ES+) M+1 501.0 for $C_{22}H_{19}ClF_2N_8O_2$.

EXAMPLE 50

2-[3-(2,2-Difluoro-2-pyridin-2-yl-ethylamino)-2-oxo-2H-pyrazin-1-yl]-N-(2-tetrazol-1-yl-benzyl)-acetamide trifluoroacetic acid salt

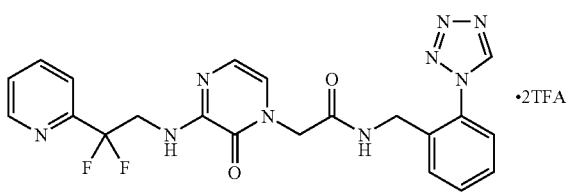

Prepared following a similar protocol as described in example 24, [3-(2,2-difluoro-2-pyridin-2-yl-ethylamino)-2-oxo-2H-pyrazin-1-yl]acetic acid (preparation described in example 19) and 2-tetrazol-1-yl-benzylamine (preparation described in example 3) were converted to 2-[3-(2,2-difluoro-2-pyridin-2-yl-ethylamino)-2-oxo-2H-pyrazin-1-yl]-N-(2-tetrazol-1-yl-benzyl)-acetamide trifluoroacetic acid salt; MS (ES+) M+1 468.1 for $C_{21}H_{19}F_2N_9O_2$.

EXAMPLE 51

2-{3-[2,2-Difluoro-2-(1-oxy-pyridin-2-yl)-ethylamino]-2-oxo-2H-pyrazin-1-yl}-N-(2-tetrazol-1-yl-benzyl)-acetamide trifluoroacetic acid salt

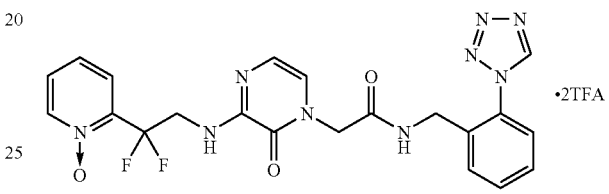

Prepared following a similar protocol as described in example 24, {3-[2,2-difluoro-2-(1-oxy-pyridin-2-yl)-ethylamino]-2-oxo-2H-pyrazin-1-yl}-acetic acid (preparation described in example 20) and 2-tetrazol-1-yl-benzylamine (preparation described in example 3) were converted to 2-{3-[2,2-difluoro-2-(1-oxy-pyridin-2-yl)-ethylamino]-2-oxo-2H-pyrazin-1-yl}-N-(2-tetrazol-1-yl-benzyl)-acetamide trifluoroacetic acid salt;

MS (ES+) M+1 484.1 for $C_{21}H_{19}F_2N_9O_3$.

EXAMPLE 52

2-{3-[2,2-Difluoro-2-(1-oxy-pyridin-2-yl)-ethylamino]-2-oxo-2H-pyrazin-1-yl)—N-(2-[1,2,4]triazol-1-yl-benzyl)-acetamide

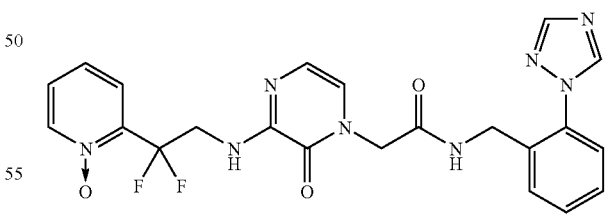

Prepared following a similar protocol as described in example 24, (3-[2,2-difluoro-2-(1-oxy-pyridin-2-yl)-ethylamino]-2-oxo-2H-pyrazin-1-yl}-acetic acid (preparation described in example 20) and 2-(1,2,4-triazol-1-yl)benzylamine (preparation described in example 9) were converted to 2-{3-[2,2-difluoro-2-(1-oxy-pyridin-2-yl)-ethylamino]-2-oxo-2H-pyrazin-1-yl}-N-(2-[1,2,4]triazol-1-yl-benzyl)-acetamide; MS (ES+) M+1 483.1 for $C_{22}H_{20}F_2N_8O_3$.

EXAMPLE 53

N-(5-Chloro-2-[1,2,4]triazol-1-yl-benzyl)-2-{3-[2,2-difluoro-2-(1-oxy-pyridin-2-yl)-ethylamino]-2-oxo-2H-pyrazin-1-yl}-acetamide

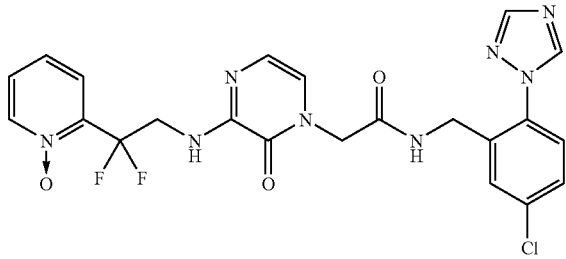

Prepared following a similar protocol as described in example 24, {3-[2,2-difluoro-2-(1-oxy-pyridin-2-yl)-ethylamino]-2-oxo-2H-pyrazin-1-yl}-acetic acid (preparation described in example 20) and 5-chloro-2-[1,2,4]triazol-1-yl-benzylamine (preparation described in example 8) were converted to N-(5-chloro-2-[1,2,4]triazol-1-yl-benzyl)-2-{3-[2,2-difluoro-2-(1-oxy-pyridin-2-yl)-ethylamino]-2-oxo-2H-pyrazin-1-yl}-acetamide; MS (ES+) M+1 517.5 for $C_{22}H_{19}ClF_2N_8O_3$.

EXAMPLE 54

N-(5-Chloro-2-tetrazol-1-yl-benzyl)-2-{3-[2,2-difluoro-2-(1-oxy-pyridin-2-yl)-ethylamino]-2-oxo-2H-pyrazin-1-yl}-acetamide

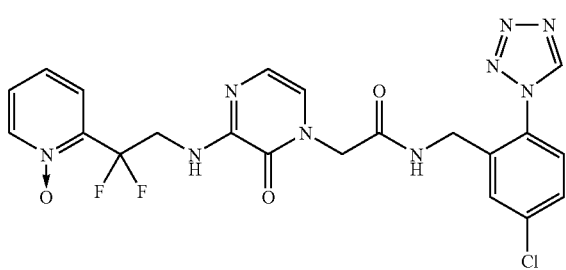

Prepared following a similar protocol as described in example 24, {3-[2,2-difluoro-2-(1-oxy-pyridin-2-yl)-ethylamino]-2-oxo-2H-pyrazin-1-yl}-acetic acid (preparation described in example 20) and and 5-chloro-2-tetrazol-1-yl-benzylamine (preparation described in example 4) were converted to N-(5-chloro-2-tetrazol-1-yl-benzyl)-2-{3-[2,2-difluoro-2-(1-oxy-pyridin-2-yl)-ethylamino]-2-oxo-2H-pyrazin-1-yl}-acetamide; MS (ES+) M+1 518.4 for $C_{21}H_{18}ClF_2N_9O_3$.

EXAMPLE 55

N-(5-Chloro-2-tetrazol-1-yl-benzyl)-2-{3-[3-(cyclopropylmethyl-amino)-propylamino]-2-oxo-2H-pyrazin-1-yl}-acetamide hydrochloride salt

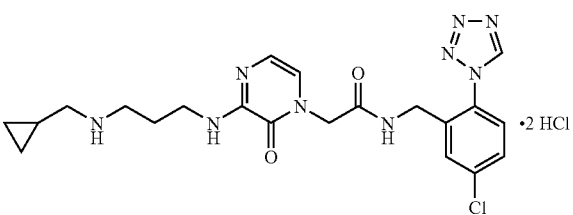

Step A (3-{4-[(5-Chloro-2-tetrazol-1-yl-benzylcarbamoyl)-methyl]-3-oxo-3,4-dihydro-pyrazin-2-ylamino}-propyl)-cyclopropylmethyl-carbamic acid tert-butyl ester Prepared following a similar protocol as described in example 24, {3-[3-(tert-butoxycarbonyl-cyclopropylmethyl-amino)-propylamino]-2-oxo-2H-pyrazin-1-yl}-acetic acid (preparation described in example 21) and 5-chloro-2-tetrazol-1-yl-benzylamine (preparation described in example 4) were converted to 3-{4-[(5-chloro-2-tetrazol-1-yl-benzylcarbamoyl)-methyl]-3-oxo-3,4-dihydro-pyrazin-2-ylamino}-propyl)-cyclopropylmethyl-carbamic acid tert-butyl ester; MS (ES+) M+1 572.5 for $C_{26}H_{34}ClN_9O_4$.

Step B

N-(5-Chloro-2-tetrazol-1-yl-benzyl)-2-{3-[3-(cyclopropylmethyl-amino)-propylamino]-2-oxo-2H-pyrazin-1-yl}-acetamide hydrochloride salt Through a solution of 3-{4-[(5-chloro-2-tetrazol-1-yl-benzylcarbamoyl)-methyl]-3-oxo-3,4-dihydro-pyrazin-2-ylamino}-propyl)-cyclopropylmethyl-carbamic acid tert-butyl ester (74 mg, 0.13 mmol) in ethyl acetate (20 ml), cooled to 0° C. was bubbled HCl (g) for 8 min. The reaction was stirred at room temperature for 0.5 h. Nitrogen was bubbled through the reaction mixture. Concentration from ethyl acetate and trituration from ethyl acetate-ether gave N-(5-chloro-2-tetrazol-1-yl-benzyl)-2-{3-[3-(cyclopropylmethyl-amino)-propylamino]-2-oxo-2H-pyrazin-1-yl}-acetamide hydrochloride salt; MS (ES+) M+1 472.5 for $C_{21}H_{26}ClN_9O_2$.

EXAMPLE 56

N-(5-Chloro-2-[1,2,4]triazol-1-yl-benzyl)-2-{3-[3-(cyclopropylmethyl-amino)-propylamino]-2-oxo-2H-pyrazin-1-yl}-acetamide hydrochloride salt

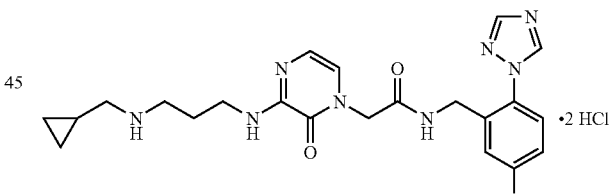

Step A (3-{4-[(5-Chloro-2-[1,2,4]triazol-1-yl-benzylcarbamoyl)-methyl]-3-oxo-3,4-dihydro-pyrazin-2-ylamino}-propyl)-cyclopropylmethyl-carbamic acid tert-butyl ester Prepared following a similar protocol as described in example 24, {3-[3-(tert-butoxycarbonyl-cyclopropylmethyl-amino)-propylamino]-2-oxo-2H-pyrazin-1-yl}-acetic acid (preparation described in example 21) and 5-chloro-2-[1,2,4]triazol-1-yl-benzylamine (preparation described in example 8) were converted to (3-{4-[(5-chloro-2-[1,2,4]triazol-1-yl-benzylcarbamoyl)-methyl]-3-oxo-3,4-dihydro-pyrazin-2-ylamino}-propyl)-cyclopropylmethyl-carbamic acid tert-butyl ester; MS (ES+) M+1 571.5 for $C_{27}H_{35}ClN_8O_4$.

Step B

N-(5-Chloro-2-[1,2,4]triazol-1-yl-benzyl)-2-[3-[3-(cyclopropylmethyl-amino)-propylamino]-2-oxo-2H-pyrazin-1-yl]-acctamide hydrochloride salt Prepared following a similar protocol as described in example 55, step B, (3-{4-[(5-chloro-2-[1,2,4]triazol-1-yl-benzylcarbamoyl)-methyl]-3-oxo-3,4-dihydro-pyrazin-2-ylamino}-propyl)-cyclopropylmethyl-carbamic acid tert-butyl ester was converted to N-(5-chloro-2-[1,2,4]triazol-1-yl-benzyl)-2-{3-[3-(cyclopropylmethyl-amino)-propylamino]-2-oxo-2H-pyrazin-1-yl}-acetamide hydrochloride salt; MS (ES+) M+1 471.5 for $C_{22}H_{27}ClN_8O_2$.

EXAMPLE 57

2-{6-Chloro-3-[3-(cyclopropylmethyl-amino)-propylamino]-2-oxo-2H-pyrazin-1-yl}-N-(2-[1,2,4]triazol-1-yl-benzyl)-acetamide hydrochloride salt

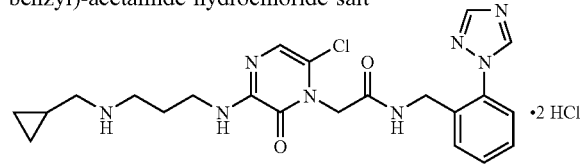

Step A (3-{5-Chloro-3-oxo-4-[(2-[1,2,4]triazol-1-yl-benzylcarbamoyl)-methyl]-3,4-dihydro-pyrazin-2-yl-amino}-propyl)-cyclopropylmethyl-carbamic acid tert-butyl ester Prepared following a similar protocol as described in example 24, {3-[3-(tert-Butoxycarbonyl-cyclopropylmethyl-amino)-propylamino]-6-chloro-2-oxo-2H-pyrazin-1-yl}-acetic acid (preparation described in example 22) and 2-(1,2,4-triazol-1-yl)benzylamine (preparation described in example 9) were converted to (3-{5-chloro-3-oxo-4-[(2-[1,2,4]triazol-1-yl-benzylcarbamoyl)-methyl]-3,4-dihydro-pyrazin-2-yl-amino}-propyl)-cyclopropylmethyl-carbamic acid tert-butyl ester; MS (ES+) M+1 571.5 for $C_{27}H_{35}ClN_8O_4$.

Step B

2-{6-Chloro-3-[3-(cyclopropylmethyl-amino)-propylamino]-2-oxo-2H-pyrazin-1-yl}-N-(2-[1,2,4]triazol-1-yl-benzyl)-acetamide hydrochloride salt Prepared following a similar protocol as described in example 55, step B, (3-{5-chloro-3-oxo-4-[(2-[1,2,4]triazol-1-yl-benzylcarbamoyl)-methyl]-3,4-dihydro-pyrazin-2-yl-amino}-propyl)-cyclopropylmethyl-carbamic acid tert-butyl ester was converted to 2-{6-chloro-3-[3-(cyclopropylmethyl-amino)-propylamino]-2-oxo-2H-pyrazin-1-yl}-N-(2-[1,2,4]triazol-1-yl-benzyl)-acetamide hydrochloride salt; MS (ES+) M+1 471.8 for $C_{22}H_{27}ClN_8O_2$.

EXAMPLE 58

2-{6-Chloro-3-[3-(cyclopropylmethyl-amino)-propylamino]-2-oxo-2H-pyrazin-1-yl}-N-(5-chloro-2-[1,2,4]triazol-1-yl-benzyl)-acetamide hydrochloride salt

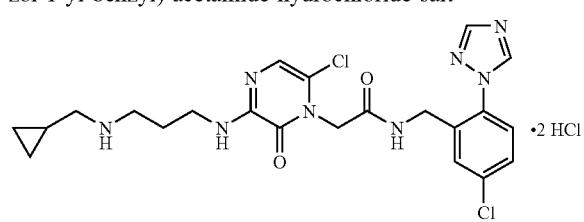

Step A (3-{5-Chloro-4-[(5-chloro-2-[1,2,4]triazol-1-yl-benzylcarbamoyl)-methyl]-3-oxo-3,4-dihydro-pyrazin-2-yl-amino}-propyl)-cyclopropylmethyl-carbamic acid tert-butyl ester Prepared following a similar protocol as described in example 24, {3-[3-(tert-Butoxycarbonyl-cyclopropylmethyl-amino)-propylamino]-6-chloro-2-oxo-2H-pyrazin-1-yl}-acetic acid (preparation described in example 22) and 5-chloro-2-[1,2,4]triazol-1-yl-benzylamine (preparation described in example 8) were converted to (3-{5-chloro-4-[(5-chloro-2-[1,2,4]triazol-1-yl-benzylcarbamoyl)-methyl]-3-oxo-3,4-dihydro-pyrazin-2-yl-amino}-propyl)-cyclopropylmethyl-carbamic acid tert-butyl ester; MS (ES+) M+1 605.5 for $C_{27}H_{34}Cl_2N_8O_4$.

Step B

2-{6-Chloro-3-[3-(cyclopropylmethyl-amino)-propylamino]-2-oxo-2H-pyrazin-1-yl}-N-(5-chloro-2-[1,2,4]triazol-1-yl-benzyl)-acetamide hydrochloride salt Prepared following a similar protocol as described in example 55, step B, (3-{5-chloro-4-[(5-chloro-2-[1,2,4]triazol-1-yl-benzylcarbamoyl)-methyl]-3-oxo-3,4-dihydro-pyrazin-2-yl-amino}-propyl)-cyclopropylmethyl-carbamic acid tert-butyl ester was converted to 2-{6-chloro-3-[3-(cyclopropylmethyl-amino)-propylamino]-2-oxo-2H-pyrazin-1-yl}-N-(5-chloro-2-[1,2,4]triazol-1-yl-benzyl)-acetamide hydrochloride salt; MS (ES+) M+1 505.8 for $C_{22}H_{26}Cl_2N_8O_2$.

EXAMPLE 59

2-(6-Methyl-2-oxo-3-phenylmethanesulfonylamino-2H-pyridin-1-yl)-N-(2-tetrazol-1-yl-benzyl)-acetamide

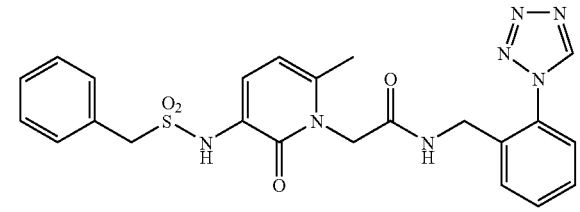

Prepared following a similar protocol as described in example 24, (6-methyl-2-oxo-3-phenylmethanesulfonylamino-2H-pyridin-1-yl)-acetic acid (preparation described in Sanderson et. al., *J. Med. Chem.* 1998, 41, 4466–4474) and 2-tetrazol-1-yl-benzylamine (preparation described in example 3) were converted to 2-(6-methyl-2-oxo-3-phenylmethanesulfonylamino-2H-pyridin-1-yl)-N-(2-tetrazol-1-yl-benzyl)acetamide; MS (ES+) M+1 494.5 for $C_{23}H_{23}N_7O_4S$.

EXAMPLE 60

N-(5-Chloro-2-tetrazol-1-yl-benzyl)-2-(6-methyl-2-oxo-3-phenylmethanesulfonylamino-2H-pyridin-1-yl)-acetamide

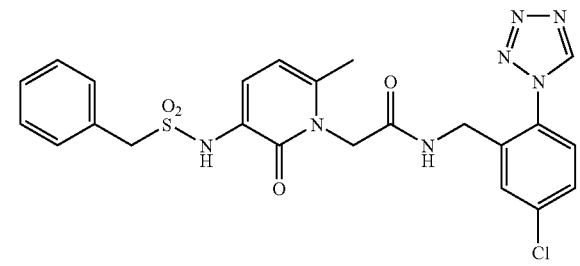

Prepared following a similar protocol as described in example 24, (6-methyl-2-oxo-3-phenylmethanesulfonylamino-2H-pyridin-1-yl)-acetic acid (preparation described in Sanderson et. al., *J. Med. Chem.* 1998, 41, 4466–4474) and 5-chloro-2-tetrazol-1-yl-benzylamine (preparation described in example 4) were converted to N-(5-chloro-2-tetrazol-1-yl-benzyl)-2-(6-methyl-2-oxo-3-phenylmethanesulfonylamino-2H-pyridin-1-yl)-acetamide;

MS (ES+) M+1 528.4 for $C_{23}H_{22}ClN_7O_4S$.

EXAMPLE 61

N-(5-Chloro-2-[1,2,4]triazol-1-yl-benzyl)-2-(6-methyl-2-oxo-3-phenylmethanesulfonylamino-2H-pyridin-1-yl)-acetamide

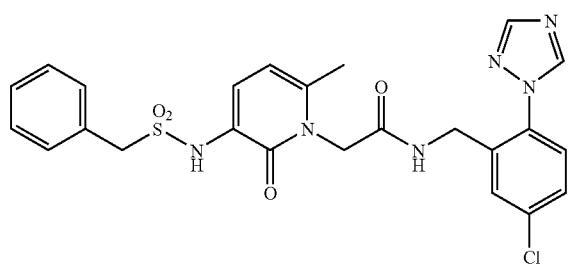

Prepared following a similar protocol as described in example 24, (6-methyl-2-oxo-3-phenylmethanesulfonylamino-2H-pyridin-1-yl)-acetic acid (preparation described in Sanderson et. al., *J. Med. Chem.* 1998, 41, 4466–4474) and 5-chloro-2-[1,2,4]triazol-1-yl-benzylamine (preparation described in example 8) were converted to N-(5-chloro-2-[1,2,4]triazol-1-yl-benzyl)-2-(6-methyl-2-oxo-3-phenylmethanesulfonylamino-2H-pyridin-1-yl)-acetamide; MS (ES+) M+1 527.4 for $C_{24}H_{23}ClN_6O_4S$.

EXAMPLE 62

2-(6-Methyl-2-oxo-3-phenylmethanesulfonylamino-2H-pyridin-1-yl)-N-(2-[1,2,4]triazol-1-yl-benzyl)-acetamide

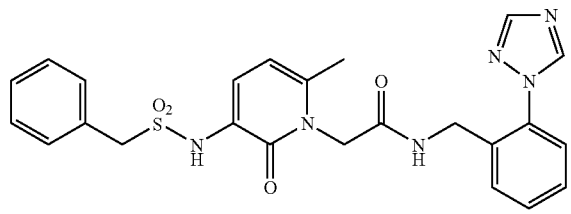

Prepared following a similar protocol as described in example 24, (6-methyl-2-oxo-3-phenylmethanesulfonylamino-2H-pyridin-1-yl)-acetic acid (preparation described in Sanderson et. al., *J. Med. Chem.* 1998, 41, 4466–4474) and 2-(1,2,4-triazol-1-yl)benzylamine (preparation described in example 9) were converted to 2-(6-methyl-2-oxo-3-phenylmethanesulfonylamino-2H-pyridin-1-yl)-N-(2-[1,2,4]triazol-1-yl-benzyl)-acetamide; MS (ES+) M+1 493.5 for $C_{24}H_{24}N_6O_4S$.

EXAMPLE 63

2-[6-Chloro-3-(1-dimethylaminomethyl-2-phenyl-ethylamino)-2-oxo-2H-pyrazin-1-yl]-N-(5-chloro-2-tetrazol-1-yl-benzyl)-acetamide hydrochloride salt

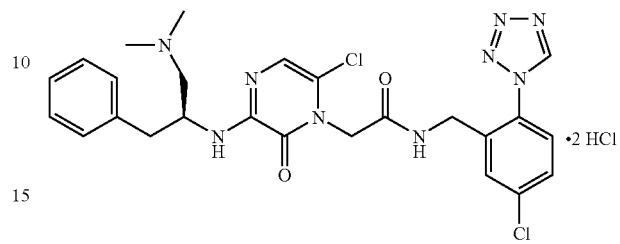

Prepared following a similar protocol as described in example 24, [6-chloro-3-(1-dimethylaminomethyl-2-phenyl-ethylamino)-2-oxo-2H-pyrazin-1-yl]-acetic acid (preparation described in example 23) and 5-chloro-2-tetrazol-1-yl-benzylamine (preparation described in example 4) were converted to 2-[6-chloro-3-(1-dimethylaminomethyl-2-phenyl-ethylamino)-2-oxo-2H-pyrazin-1-yl]-N-(5-chloro-2-tetrazol-1-yl-benzyl)-acetamide hydrochloride salt; MS (ES+) M+1 556.0 for $C_{25}H_{27}Cl_2N_9O_2$.

Typical tablet cores suitable for administration of thrombin inhibitors are comprised of, but not limited to, the following amounts of standard ingredients:

| Excipient | General Range (%) | Preferred Range (%) | Most Preferred Range (%) |
|---|---|---|---|
| mannitol | 10–90 | 25–75 | 30–60 |
| microcrystalline cellulose | 10–90 | 25–75 | 30–60 |
| magnesium stearate | 0.1–5.0 | 0.1–2.5 | 0.5–1.5 |

Mannitol, microcrystalline cellulose and magnesium stearate may be substituted with alternative pharmaceutically acceptable excipients.

In Vitro Assay for Determining Proteinase Inhibition

Assays of human α-thrombin and human trypsin were performed by the methods substantially as described in Thrombosis Research, Issue No. 70, page 173 (1993) by S. D. Lewis et al. In certain studies with potent inhibitors ($K_i$<10 nM) where the degree of inhibition of thrombin was high, a more sensitive activity assay was employed. In this assay the rate of thrombin catalyzed hydrolysis of the fluorogenic substrate Z-GPR-afc ($K_m$=27 μM) was determined from the increase in fluorescence at 500 nm (excitation at 400 nm) associated with production of 7-amino-4-trifluoromethyl coumarin. Concentrations of stock solutions of Z-GPR-afc were determined from measurements of absorbance at 380 nm of the 7-amino-4trifluoromethyl coumarin produced upon complete hydrolysis of an aliquot of the stock solution by thrombin. Activity assays were performed by diluting a stock solution of substrate at least tenfold to a final concentration ≦0.1 $K_m$ into a solution containing enzyme or enzyme equilibrated with inhibitor. Times required to achieve equilibration between enzyme and inhibitor were determined in control experiments. The activities shown by this assay indicate that the compounds of the invention are therapeutically useful for treating various conditions in patients suffering from unstable angina, refractory angina, myocardial infarction, transient ischemic attacks, atrial fibrillation, thrombotic stroke, embolic stroke, deep vein thrombosis, disseminated intravascular coagulation, and reocclusion or restenosis of recanalized vessels.

EXAMPLE 64

Tablet Preparation

Tablets containing 25.0, 50.0, and 100.0 mg., respectively, of the following active compounds are prepared as illustrated below (compositions A–C). Active I is compound 2-{6-Chloro-3-[2,2-difluoro-2-(1-oxy-pyridin-2-yl)-ethylamino]-2-oxo-2H-pyrazin-1-yl}-N-(2-tetrazol-1-yl-benzyl)-acetamide.

| Component | Amount-(mg) | | |
| --- | --- | --- | --- |
|  | A | B | C |
| Active I | 25 | 50 | 100 |
| Microcrystalline cellulose | 37.25 | 100 | 200 |
| Modified food corn starch | 37.25 | 4.25 | 8.5 |
| Magnesium stearate | 0.5 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 65

Tablet Preparation

Exemplary compositions of compound 2-{6-Chloro-3-[2,2-difluoro-2-(1-oxy-pyridin-2-yl)-ethylamino]-2-oxo-2H-pyrazin-1-yl}-N-(2-tetrazol-1-yl-benzyl)-acetamide (Active I) tablets are shown below:

| Component | 0.25 mg | 2 mg | 10 mg | 50 mg |
| --- | --- | --- | --- | --- |
| Active I | 0.500% | 1.000% | 5.000% | 14.29% |
| mannitol | 49.50% | 49.25% | 47.25% | 42.61% |
| microcrystalline cellulose | 49.50% | 49.25% | 47.25% | 42.61% |
| magnesium stearate | 0.500% | 0.500% | 0.500% | 0.500% |

2, 10 and 50 mg tablets were film-coated with an aqueous dispersion of hydroxypropyl cellulose, hydroxypropyl methylcellulose and titanium dioxide, providing a nominal weight gain of 2.4%.

Tablet Preparation via Direct Compression

Active I, mannitol and microcrystalline cellulose were sieved through mesh screens of specified size (generally 250 to 750 μm) and combined in a suitable blender. The mixture was subsequently blended (typically 15 to 30 min) until the drug was uniformly distributed in the resulting dry powder blend. Magnesium stearate was screened and added to the blender, after which a precompression tablet blend was achieved upon additional mixing (typically 2 to 10 min). The precompression tablet blend was then compacted under an applied force, typically ranging from 0.5 to 2.5 metric tons, sufficient to yield tablets of suitable physical strength with acceptable disintegration times (specifications will vary with the size and potency of the compressed tablet). In the case of the 2, 10 and 50 mg potencies, the tablets were dedusted and film-coated with an aqueous dispersion of water-soluble polymers and pigment.

Tablet Preparation via Dry Granulation

Alternatively, a dry powder blend is compacted under modest forces and remilled to afford granules of specified particle size. The granules are then mixed with magnesium stearate and tabletted as stated above.

EXAMPLE 66

Intravenous Formulations

Intravenous formulations of compound 2-{6-Chloro-3-[2,2-difluoro-2-(1-oxy-pyridin-2-yl)-ethylamino]-2-oxo-2H-pyrazin-1-yl}-N-(2-tetrazol-1-yl-benzyl)-acetamide (Active I) were prepared according to general intravenous formulation procedures.

| Component | Estimated range |
| --- | --- |
| Active I | 0.12–0.61 mg |
| D-glucuronic acid* | 0.5–5 mg |
| Mannitol NF | 50–53 mg |
| 1 N Sodium Hydroxide | q.s. pH 3.9–4.1 |
| Water for injection | q.s. 1.0 mL |

Exemplary compositions A–C are as follows:

| Component | A | B | C |
| --- | --- | --- | --- |
| Active I | 0.61 mg* | 0.30** | 0.15*** |
| D-glucuronic acid* | 1.94 mg | 1.94 mg | 1.94 mg |
| Mannitol NF | 51.2 mg | 51.2 mg | 51.2 mg |
| 1 N Sodium Hydroxide | q.s. pH 4.0 | q.s. pH 4.0 | q.s. pH 4.0 |
| Water for injection | q.s. 1.0 mL | q.s. 1.0 mL | q.s. 1.0 mL |

*0.50 mg free base
**0.25 mg free base
***0.12 mg free base

Various other buffer acids, such as L-lactic acid, acetic acid, citric acid or any pharmaceutically acceptable acid/conjugate base with reasonable buffering capacity in the pH range acceptable for intravenous administration may be substituted for glucuronic acid.

What is claimed is:

1. A compound of the general formula:

$$A-Z-HN\underset{O}{\overset{X}{\bigvee}}\underset{}{\overset{R^1}{\bigvee}}\underset{H}{\overset{O}{\bigvee}}R^2$$

and pharmaceutically acceptable salts thereof, wherein
A is
1) a 6-membered non-heterocyclic unsaturated ring system, unsubstituted, monosubstituted, disubstituted, or trisubstituted, same or different, with $C_{1-4}$ alkyl,
2) a 6-membered heterocyclic unsaturated or saturated ring system wherein 1 ring atom is selected from the group of heteroatoms consisting of N, O and S, wherein the ring carbons are unsubstituted, monosubstituted, disubstituted, or trisubstituted, same or different, with $C_{1-4}$ alkyl, 3) 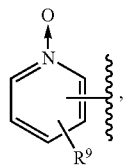

where R is hydrogen or $C_{1-8}$alkyl, or
4) —$C_{3-8}$ cycloalkyl;

Z is —$(CH_2)_{2-4}$—, —$CF_2(CH_2)_{1-3}$—, —$(CH_2)_{1-3}SO_2$—, —$(CH_2)_{1-2}NH(CH_2)_{1-4}$—, or —$CH_2CH(R^4)$—, where $R^4$ is —$(CH_2)_{1-2}N(R^5R^6)$, and $R^5$ and $R^6$, same or different, are selected from the group consisting of hydrogen and $C_{1-4}$alkyl;

X is CH or N;

$R^1$ is hydrogen, halogen, or $C_{1-4}$alkyl;

$R^2$ is

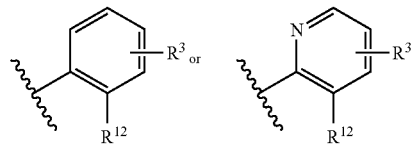

$R^3$ is selected from the group consisting of
1) hydrogen,
2) halogen,
3) $C_{1-4}$ alkyl,
4) $C_{3-7}$ cycloalkyl,
5) $CF_3$,
6) $OCF_3$,
7) $C_{1-4}$ alkoxy, and
8) cyano;

$R^{12}$ is a 5-membered heteroaryl ring having 2, 3, or 4 heteroatoms, provided that at least 1 heteroatom is N, and at most 1 of the heteroatoms is S, said ring being unsubstituted or substituted, at any one ring atom, with $CH_3$.

2. A compound of claim 1, or pharmaceutically acceptable salt thereof, wherein $R^1$ is hydrogen, Cl, or $CH_3$.

3. A compound of claim 2, or pharmaceutically acceptable salt thereof, wherein A is selected from the group consisting of

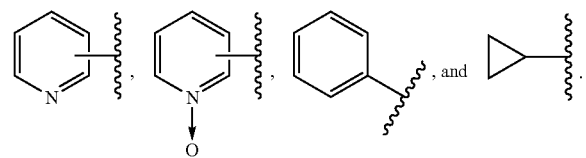

4. A compound of claim 3, or pharmaceutically acceptable salt thereof, wherein
A is selected from the group consisting of

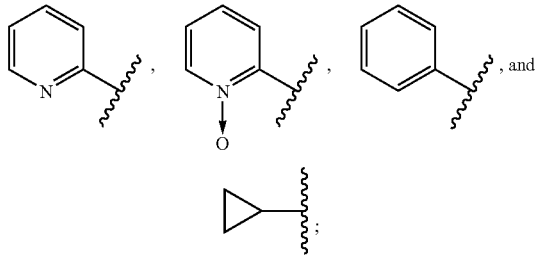

Z is selected from the group consisting of —$CF_2CH_2$—, —$CH_2CH(CH_2N(CH_3)_2)$—, —$CH_2SO_2$—, and —$CH_2NH(CH_2)_3$—;

X is N or CH;

$R^1$ is hydrogen, Cl, or $CH_3$; and $R^2$ is selected from the group consisting of

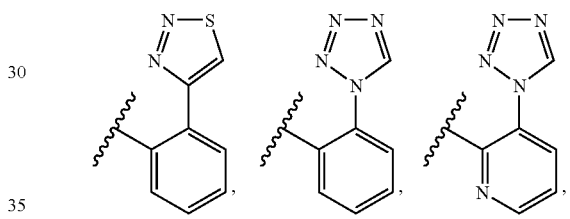

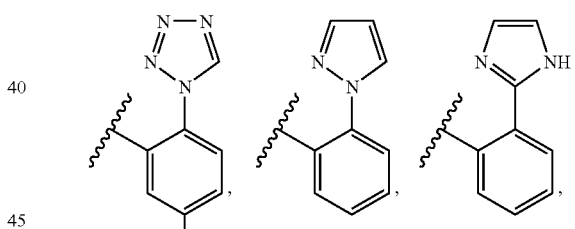

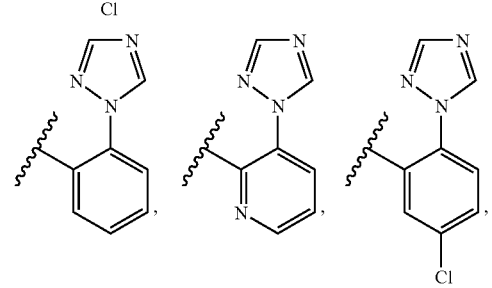

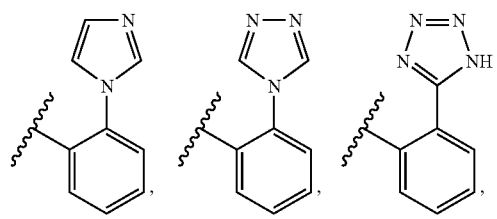

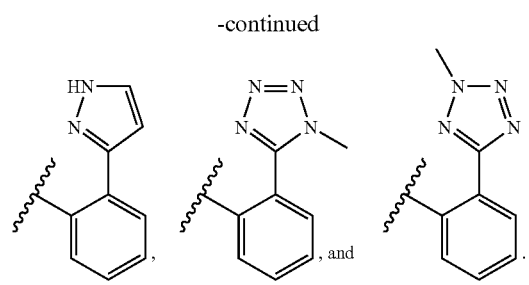, 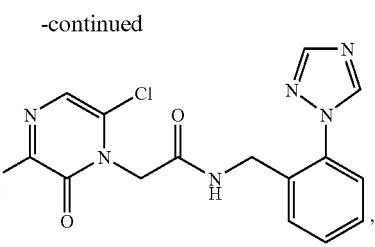
5. A compound of claim 4, or pharmaceutically acceptable salt thereof, selected from the group consisting of
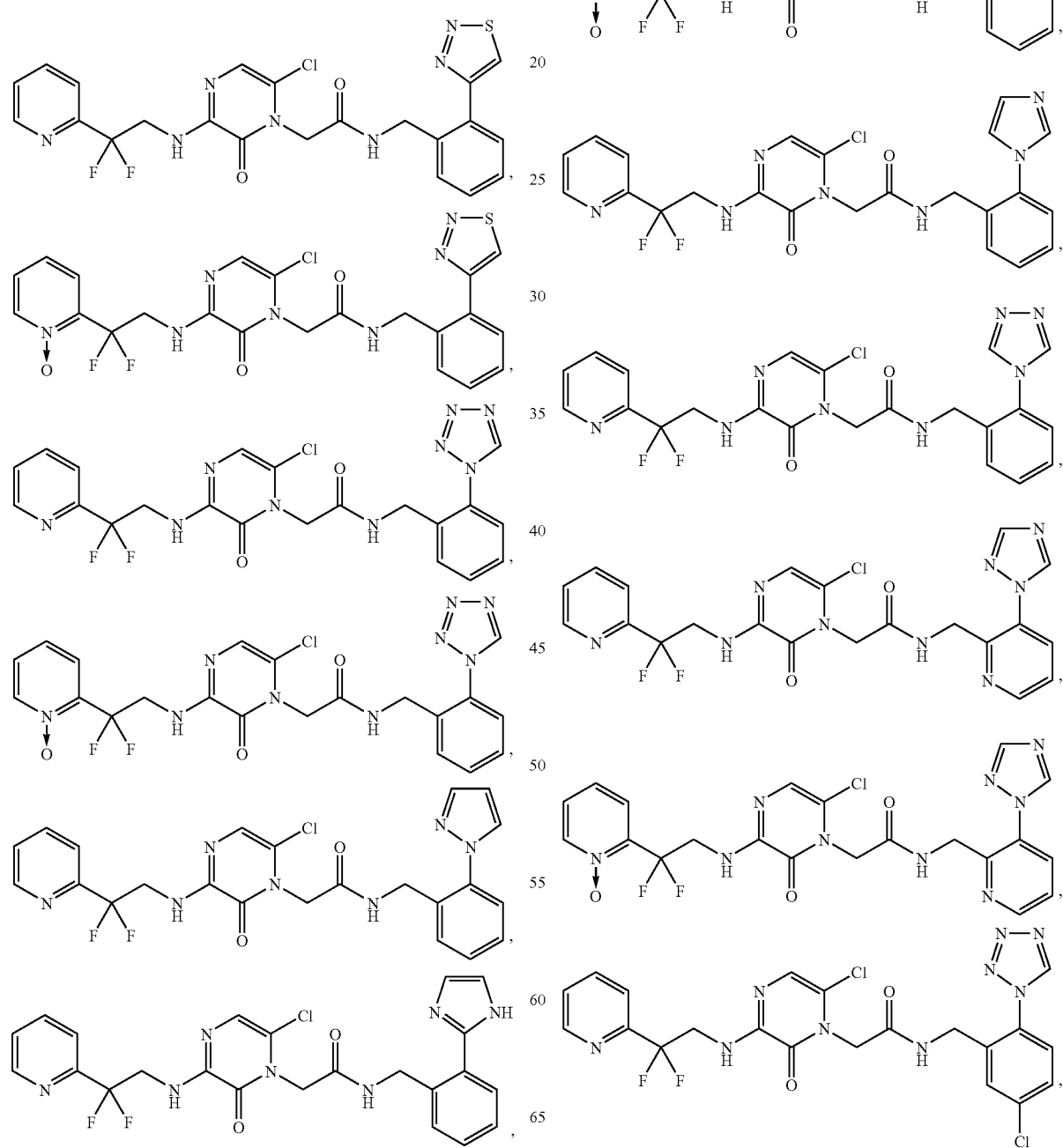

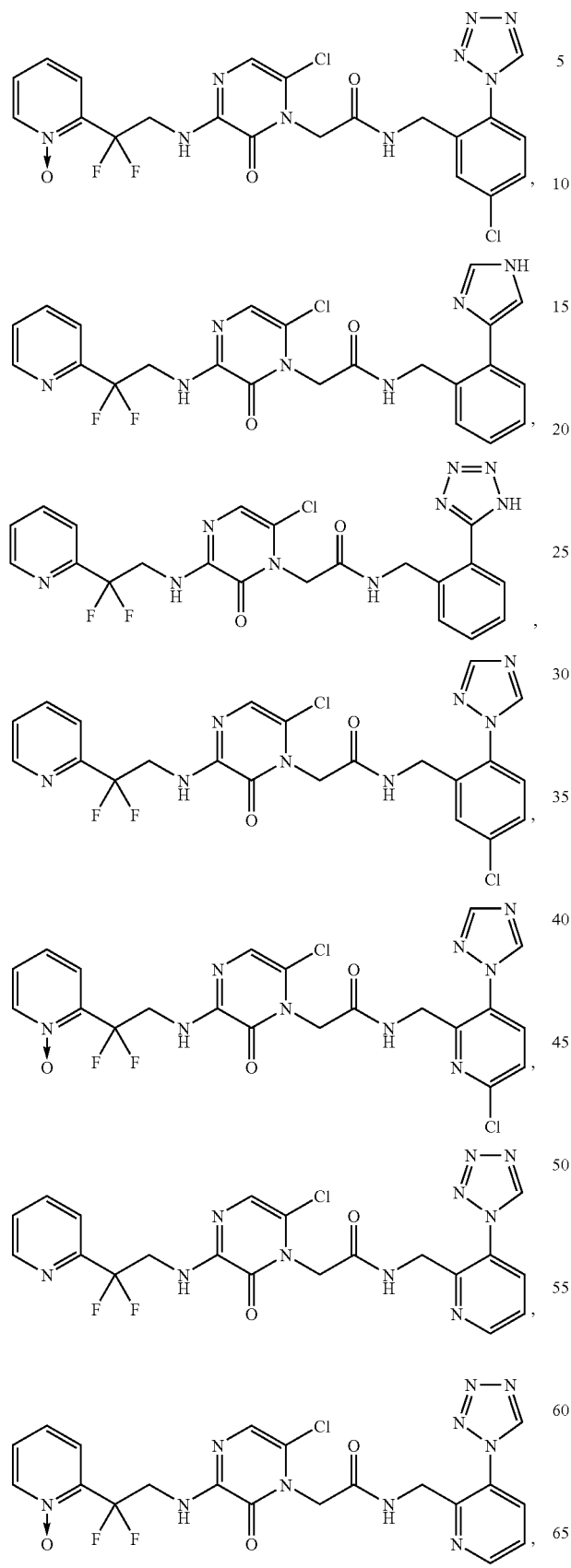
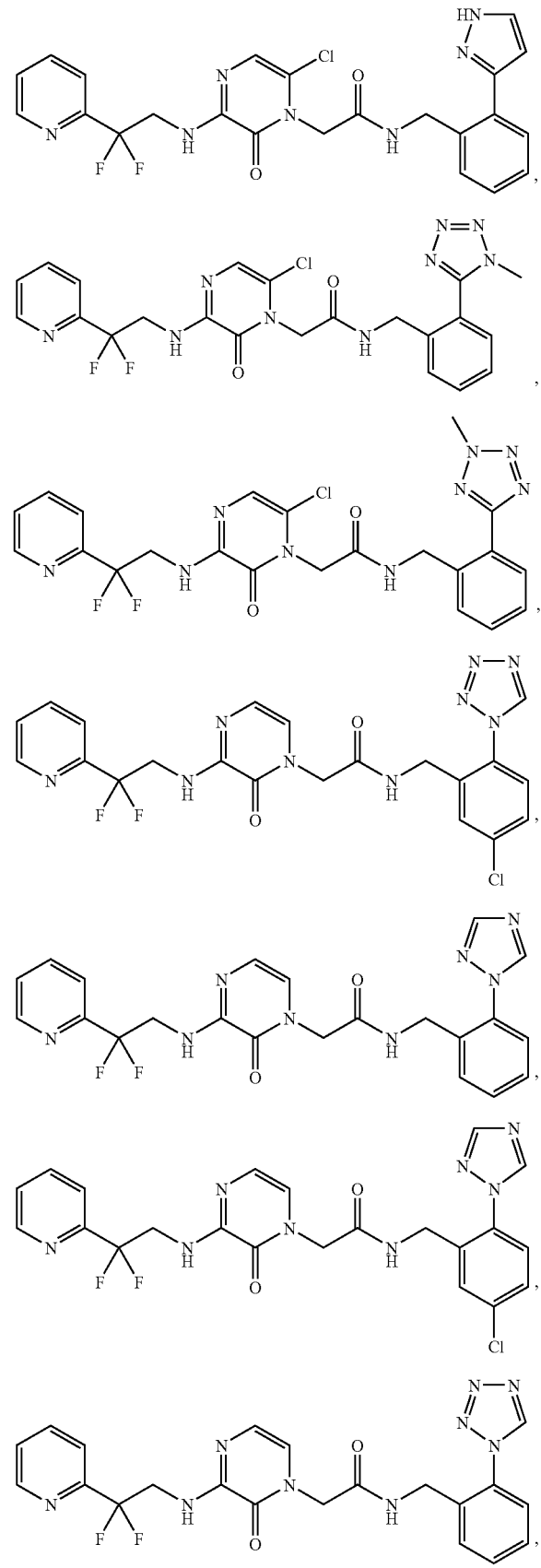

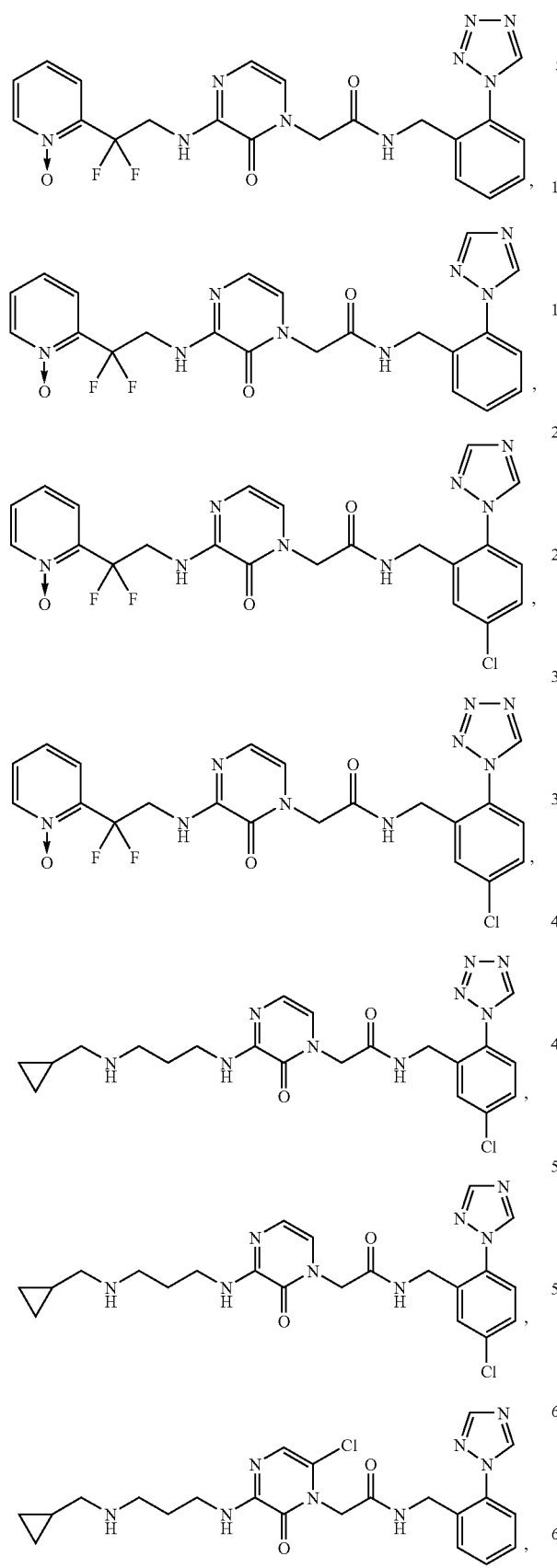
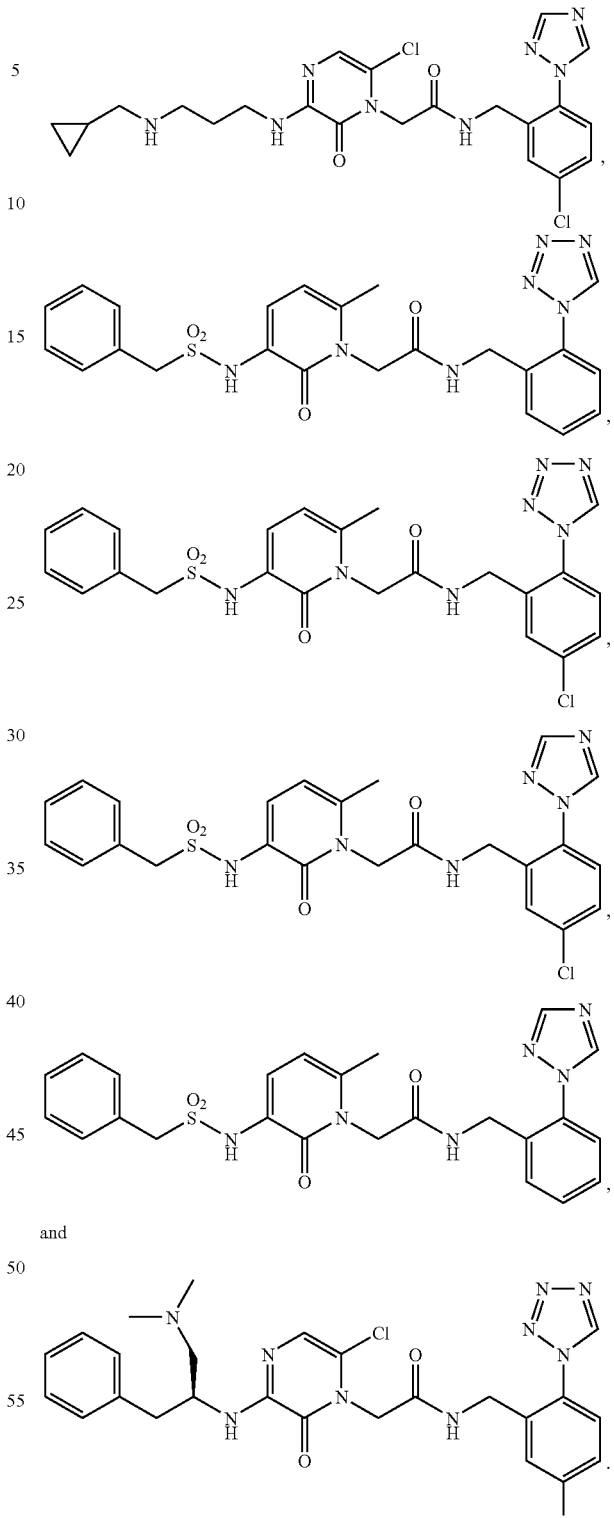
6. A composition for inhibiting thrombus formation in blood comprising a compound of claim 1 and a pharmaceutically acceptable carrier.
7. A method for inhibiting thrombin in blood comprising adding to the blood a composition of claim 6.

8. A method for inhibiting formation of blood platelet aggregates in blood comprising adding to the blood a composition of claim 6.

9. A method for inhibiting thrombus formation in blood comprising adding to the blood a composition of claim 6.

10. A method for treating venous thromboembolism and pulmonary embolism in a mammal comprising administering to the mammal a composition of claim 6.

11. A method for treating deep vein thrombosis in a mammal comprising administering to the mammal a composition of claim 6.

12. A method for treating thromboembolic stroke in humans and other mammals comprising administering to the mammal a composition of claim 6.

\* \* \* \* \*